United States Patent
Umemura et al.

(10) Patent No.: US 7,867,980 B2
(45) Date of Patent: Jan. 11, 2011

(54) LINCOSAMIDE DERIVATIVES AND ANTIMICROBIAL AGENTS COMPRISING THE SAME AS ACTIVE INGREDIENT

(75) Inventors: Eijirou Umemura, Chigasaki (JP); Kou Kumura, Yokohama (JP); Satomi Masaki, Saitama (JP); Kazutaka Ueda, Kitakami (JP); Yoshinari Wakiyama, Tokyo-To (JP); Yasuo Sato, Hachioji (JP); Mikio Yamamoto, Kawasaki (JP); Keiichi Ajito, Kawasaki (JP); Takashi Watanabe, Yokohama (JP); Chizuko Kaji, Kawasaki (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 12/451,752

(22) PCT Filed: May 30, 2008

(86) PCT No.: PCT/JP2008/060045

§ 371 (c)(1),
(2), (4) Date: Mar. 3, 2010

(87) PCT Pub. No.: WO2008/146919

PCT Pub. Date: Dec. 4, 2008

(65) Prior Publication Data

US 2010/0184746 A1 Jul. 22, 2010

(30) Foreign Application Priority Data

May 31, 2007 (JP) ............................. 2007-146200

(51) Int. Cl.
- *A01N 43/04* (2006.01)
- *A61K 31/70* (2006.01)
- *C07H 15/16* (2006.01)

(52) U.S. Cl. ...................... 514/24; 536/16.2; 536/16.3; 536/16.4; 536/16.5

(58) Field of Classification Search ........................ None
See application file for complete search history.

(56) References Cited

U.S. PATENT DOCUMENTS

| 3,544,551 A | 12/1970 | Kagan et al. | |
|---|---|---|---|
| 3,689,474 A | 9/1972 | Kagan et al. | |
| 3,767,649 A | 10/1973 | Bannister | |
| 3,870,699 A | 3/1975 | Bannister | |
| 3,915,954 A | 10/1975 | Bannister | |
| 7,164,011 B2 * | 1/2007 | Lewis et al. ................. | 536/16.5 |
| 7,199,105 B2 * | 4/2007 | Lewis et al. .................... | 514/24 |
| 7,199,106 B2 * | 4/2007 | Lewis et al. .................... | 514/24 |
| 7,256,177 B2 * | 8/2007 | Lewis et al. .................... | 514/24 |
| 7,361,743 B2 * | 4/2008 | Lewis et al. ................. | 536/16.3 |

FOREIGN PATENT DOCUMENTS

| DE | 2 229 950 | 12/1972 |
|---|---|---|
| JP | 2006-504673 | 2/2006 |
| WO | 2005/007665 | 1/2005 |
| WO | 2005/012320 | 2/2005 |
| WO | 2006/055070 | 5/2006 |
| WO | 2007/066805 | 6/2007 |

OTHER PUBLICATIONS

English translation of the International Preliminary Report on Patentability, 2008.
International Search Report issued Jul. 1, 2008 in International (PCT) Application No. PCT/JP2008/060045.
F. Sztaricskai et al., "Semisynthetic Modification of Antibiotic Lincomycin", The Journal of Antibiotics, vol. 49, No. 9, pp. 941-943, Sep. 1996.
R. D. Birkenmeyer et al., "Synthesis and Antimicrobial Activity of Clindamycin Analogues: Pirlimycin, a Potent Antibacterial Agent", J. Med. Chem., vol. 27, No. 2, pp. 216-223, 1984.
F. Sakamoto et al., "Studies on Prodrugs. II. Preparation and Characterization of (5-Substituted 2-Oxo-1,3-dioxolen-4-yl)methyl Esters of Ampicillin", Chem. Pharm. Bull., vol. 32, No. 6, pp. 2241-2248, 1984.
R. Zhang et al., "Pseudo-A(1,3) Strain as a Key Conformational Control Element in the Design of Poly-L-proline Type II Peptide Mimics", J. Am. Chem. Soc., vol. 120, No. 16, pp. 3894-3902, 1998.

(Continued)

*Primary Examiner*—Traviss C McIntosh, III
(74) *Attorney, Agent, or Firm*—Wenderoth, Lind & Ponack, L.L.P.

(57) ABSTRACT

An objective of the present invention is to provide compounds of formula (I) or their pharmacologically acceptable salts or solvates wherein A represents aryl while $R_1$ represents a five- or six-membered monocyclic heterocyclic group, or A represents a four- to six-membered monocyclic heterocyclic group while $R_1$ represents aryl or a five- or six-membered monocyclic heterocyclic group; $R_2$ represents a hydrogen atom or $C_{1-6}$ alkyl; $R_3$ represents $C_{1-6}$ alkyl or $C_{3-6}$ cycloalkyl-$C_{1-4}$ alkyl; $R_4$, $R_5$, and $R_6$ represent a hydrogen atom; $R_7$ represents $C_{1-6}$ alkyl; and m is 1 to 3. The compounds are novel lincosamide derivatives that have a potent activity against resistant *Streptococcus pneumoniae*. Further, the compounds are usable as antimicrobial agents and are useful for preventing or treating bacterial infectious diseases.

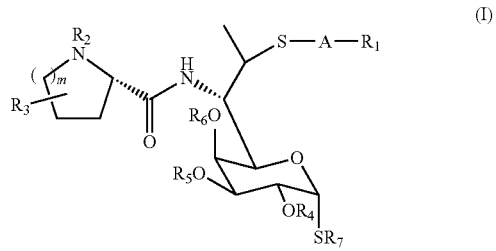

(I)

13 Claims, No Drawings

OTHER PUBLICATIONS

R. D. Birkenmeyer et al., "Lincomycin. XI. Synthesis and Structure of Clindamycin. a Potent Antibacterial Agent", Journal of Medicinal Chemisty, vol. 13; No. 4, pp. 616-619, 1970.

P. L. Ornstein et al., "Synthesis and Pharmacology of a Series of 3- and 4-(Phosphonoalkyl)pyridine- and -piperidine-2- carboxylic Acids. Potent *N*-Methyl-D-aspartate Receptor Antagonists", J. Med. Chem., vol. 32, No. 4, pp. 827-833, 1989.

J. Alexander et al., "Investigation of (Oxodioxolenyl)methyl Carbamates as Nonchiral Bioreversible Prodrug Moieties for Chiral Amines", J. Med. Chem., vol. 39, No. 2, pp. 480-486, 1996.

C. Pedregal et al., "Highly Chemoselective Reduction of N-Boc Protected Lactams", Tetrahedron Letters, vol. 35, No. 13, pp. 2053-2056, 1994.

* cited by examiner

LINCOSAMIDE DERIVATIVES AND ANTIMICROBIAL AGENTS COMPRISING THE SAME AS ACTIVE INGREDIENT

This application is a U.S. national stage of International Application No. PCT/JP2008/060045 filed May 30, 2008.

CROSS-REFERENCE TO RELATED APPLICATIONS

This application is based upon and claims the benefit of priority from the prior Japanese Patent Application No. 146200/2007, filed on May 31, 2007, the entire contents of which are incorporated herein by reference.

BACKGROUND OF THE INVENTION

1. Field of the Invention

The present invention relates to novel lincosamide derivatives having antimicrobial activity or their pharmacologically acceptable salts thereof. The present invention also relates to antimicrobial agents comprising the compounds as active ingredient.

2. Related Art

Various compounds have hitherto been reported as lincosamide derivatives having antimicrobial activity. It is also disclosed that compounds having a structure similar to the compounds according to the present invention have antimicrobial activity. See, for example, (1) U.S. Pat. No. 3,915,954, (2) U.S. Pat. No. 3,870,699, (3) U.S. Pat. No. 3,767,649, (4) German Patent Laid-Open No. 2229950, (5) U.S. Pat. No. 3,689,474, (6) U.S. Pat. No. 3,544,551, (7) International Publication WO 2005/012320, (8) J. Antibiotics, 49, (1996), 941, and (9) Structure-Activity Relationships among the semisynthetic antibiotics, 601-651.

The compounds described in these documents, however, are ineffective against macrolide resistant pneumococci which have recently posed a clinical problem. Accordingly, the development of antimicrobial agents which are also effective against resistant pneumococci has been desired.

SUMMARY OF THE INVENTION

The present inventors have now found that a group of lincosamide derivatives represented by formula (I) have potent antimicrobial activity against macrolide resistant pneumococci against which lincomycin and clindamycin are ineffective. The present invention has been made based on such finding.

Accordingly, an object of the present invention is to provide novel lincosamide derivatives having potent activity against resistant pneumococci in the treatment of infectious diseases as a recent issue.

The compounds according to the present invention, that is, novel lincosamide derivatives according to the present invention are compounds of formula (I) or their pharmacologically acceptable salts or solvates:

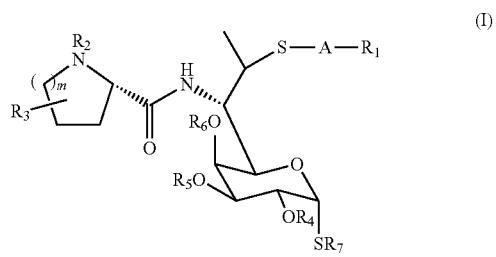

wherein

A represents benzyl in which methylene in the benzyl group is bonded to S;

aryl optionally substituted by one or more groups selected from the group consisting of $C_{1-6}$ alkyl, halides, cyano, and $C_{1-6}$ alkyloxy; or a monocyclic or dicyclic heterocyclic group, in which each ring has four to six members, optionally substituted by one or more groups selected from the group consisting of $C_{1-6}$ alkyl and $C_{1-6}$ alkyl halides
wherein the heterocyclic group contains 1 to 4 dissimilar atoms selected from the group consisting of nitrogen, oxygen, and sulfur atoms, $R_1$ represents pyridyl-$CHR_8$— wherein $R_8$ represents hydroxyl or $C_{1-6}$ alkyloxy;

morpholinocarbonyl;

arylthio optionally substituted by one or more groups selected from the group consisting of $C_{1-6}$ alkyl, halides, cyano, and nitro;

optionally substituted aryl
wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, $C_{1-6}$ alkyloxy halides, hydroxy-$C_{1-6}$ alkyl, hydroxy-$C_{1-6}$ alkylamino, $C_{1-6}$ alkylamino, alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;

an optionally substituted five- to seven-membered monocyclic heterocyclic group
wherein the five- to seven-membered heterocyclic group is optionally substituted by one or more groups selected from the group consisting of halides, nitro, cyano, $C_{1-6}$ alkylamino, alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or a dicyclic heterocyclic group in which each of the rings has four to six members $R_2$ represents a hydrogen atom;

optionally substituted $C_{1-6}$ alkyl;

optionally substituted $C_{2-6}$ alkenyl;

optionally substituted acyl;

$C_{1-6}$ alkylcarbonylaminomethyl;

$C_{1-6}$ alkylcarbonyloxymethylcarbonyl;

$C_{1-6}$ alkylcarbonyloxymethyloxycarbonyl;

(5-methyl-1,3-dioxol-2-oxo-4-yl)methyl;

(5-methyl-1,3-dioxol-2-oxo-4-yl)methyloxycarbonyl;

optionally substituted $C_{1-6}$ alkyloxycarbonyl
  wherein the $C_{1-6}$ alkyl, $C_{2-6}$ alkenyl, acyl, and $C_{1-6}$ alkyloxycarbonyl groups in $R_2$ are optionally substituted by one or more groups selected from the group consisting of heterocyclic rings optionally substituted by $C_{1-6}$ alkyl, amino, hydroxy, and cyano;
aryloxycarbonyl; or
$C_{3-6}$ cycloalkyl,
$R_3$ represents
optionally substituted $C_{1-6}$ alkyl
  wherein the $C_{1-6}$ alkyl group is optionally substituted by one or more groups that are selected from the group consisting of halides; nitro; hydroxy; amino; $C_{1-6}$ alkyloxycarbonyl; carbamoyl; cyano; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide or $C_{1-4}$ alkyl;
$C_{3-6}$ cycloalkyl-$C_{1-4}$ alkyl; or
$C_{2-6}$ alkenyl,
$R_4$, $R_5$, and $R_6$, which may be the same or different, represent
a hydrogen atom;
optionally substituted $C_{1-6}$ alkyl;
optionally substituted acyl
  wherein the $C_{1-6}$ alkyl group and hydrogen atoms on the acyl group in $R_4$, $R_5$, and $R_6$ are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy or $C_{1-4}$ alkyl; or
benzoyl,
$R_7$ represents
$C_{1-6}$ alkyl optionally substituted by one or more groups selected from the group consisting of halides and hydroxy, and
m is 1 to 3,
provided that
when $R_3$ represents optionally substituted $C_{1-6}$ alkyl or $C_{2-6}$ alkenyl, $R_1$-A- represents
  a group selected from the group consisting of 5-pyrimidinyl-phenyl-, 2-pyrimidinyl-phenyl-, 3-piperidinyl-phenyl-, 4-piperidinyl-phenyl-, 3-tetrahydropyridyl-phenyl-, 2-pyrazinyl-phenyl-, 6-tetrahydropyridazinyl-phenyl-, 1,2-oxazol-5-yl-phenyl-, 1,3-oxazolidin-3-yl-phenyl-, 1,2,3-thiadiazol-4-yl-phenyl, 1,3,4-thiadiazol-2-yl-phenyl, 2-(3-piperidinyl)-pyridin-3-yl, 1,3-oxazol-5-yl-phenyl-, phenylthio-phenyl-, $C_{1-6}$ alkyloxy (pyridyl)methyl-phenyl-, hydroxy(pyridyl)methyl-phenyl-, thiazol-4-yl-phenyl-, thiazol-2-yl-phenyl-, 1-piperazinyl-phenyl-, 1-pyrrolidinyl-phenyl-, 1-dihydroimidazolyl-phenyl-, 2-(1,3-oxazol-5-yl)-thiophen-4-yl-, 2-(pyrimidin-5-yl)-thiophen-4-yl, 3-(pyrimidin-5-yl)-pyridin-6-yl, 2-(pyrimidin-5-yl)-pyridin-5-yl, 2-(tetrahydropyridin-3-yl)-pyridin-5-yl, 2-(pyrrolidin-1-yl)-pyridin-5-yl, 5-(pyrimidin-5-yl)-pyrimidin-2-yl, and 2-(pyrimidin-5-yl)-pyrimidin-5-yl wherein $R_1$ and A in the $R_1$-A -group each are optionally substituted as defined above.

According to the present invention, there is provided a pharmaceutical composition comprising the compound of formula (I) or its pharmacologically acceptable salt or solvate and a pharmaceutically acceptable carrier. In a preferred embodiment of the present invention, there are provided pharmaceutical compositions comprising the above compound as an active ingredient together with an additive for a pharmaceutical preparation. These pharmaceutical compositions are useful for the prevention or treatment of microbisms (bacterial infectious diseases) (preferably microbisms in respiratory organs) and can be used as antimicrobial agents (that is, antimicrobial compositions).

According to another aspect of the present invention, there is provided an antimicrobial agent comprising the compound according to the present invention or its pharmacologically acceptable salt or solvate as active ingredient.

According to still another aspect of the present invention, there is provided a method for treating bacterial infectious diseases, comprising administering a therapeutically effective amount of the compound according to the present invention or its pharmacologically acceptable salt or solvate together with a pharmaceutically acceptable carrier to a mammal or a domestic fowl.

According to a further aspect of the present invention, there is provided use of the compound according to the present invention or its pharmacologically acceptable salt or solvate for the production of a pharmaceutical composition for preventing or treating bacterial infectious diseases. According to a still further aspect of the present invention, there is provided use of the compound according to the present invention or its pharmacologically acceptable salt or solvate as an active ingredient of an antimicrobial agent. In this case, the bacterial infectious diseases are preferably those in respiratory organs.

The lincosamine derivatives of formula (I) according to the present invention have potent antimicrobial activity against resistant pneumococci against which not only lincosamide-type antibiotics such as clindamycin but also other antibiotics such as macrolide antibiotics are ineffective. Accordingly, the compounds according to the present invention are expected to be excellent therapeutic agents for infectious diseases in respiratory organs.

DETAILED DESCRIPTION OF THE INVENTION

Compounds of Formula (I)

The term "$C_{1-6}$ alkyl" as used herein as a group or a part of a group means alkyl having 1 to 6 carbon atoms, which is of a straight chain or branched chain. $C_{1-6}$ alkyl is preferably $C_{1-4}$ alkyl, more preferably $C_{1-2}$ alkyl.

Examples of $C_{1-6}$ alkyl include methyl, ethyl, n-propyl, iso-propyl, n-butyl, iso-butyl, sec-butyl, tert-butyl, n-pentyl, and n-hexyl.

The alkenyl and the alkenyl moiety in the substituent containing the alkenyl group moiety may be, for example, vinyl, allyl, 1-propenyl, isopropenyl, 1-butenyl, 2-butenyl, propargyl, 1-butynyl, 1-pentynyl, or 2-butynyl which is of a straight chain, branched chain, or cyclic type or a combination thereof unless otherwise specified, preferably of a straight chain or branched chain type. The term "$C_{2-6}$ alkenyl" refers to alkenyl having 2 to 6 carbon atoms, preferably $C_{2-4}$ alkenyl. The number of double bonds contained in the alkenyl moiety is not particularly limited, and the double bond contained in the alkenyl moiety may be a Z configuration or an E configuration.

Acyl and the acyl moiety in the acyl moiety-containing substituent (for example, acyloxy such as acetoxy) as used herein refer to $C_2$ to $C_5$ straight-chain or branched-chain alkylcarbonyl or formyl, such as acetyl, propionyl, butyryl, isobutyryl, valeryl, or isovaleryl, unless otherwise specified.

The expression "alkyl optionally substituted by" as used herein refers to alkyl, wherein one or more hydrogen atoms on the alkyl group are substituted by one or more substituents which may be the same or different, and unsubstituted alkyl.

It will be apparent to a person having ordinary skill in the art that the maximum number of substituents may be determined depending upon the number of substitutable hydrogen atoms on the alkyl group. This is true of groups containing substituents other than alkyl, for example, alkenyl, acyl, and aryl such as phenyl, and heterocyclic rings such as 1,3,4-thiadiazolyl.

The term "halide" (halogen atom) as used herein refers to a fluorine, chlorine, bromine, or iodine atom.

The term "halide" used herein, for example, in "alkyl halide" as a group or a part of a group means that one or more hydrogen atoms on each group have been substituted by a halogen atom.

The term "aryl" as used herein refers to a heteroatom-free six- to fourteen-membered (monocyclic to tricyclic, preferably monocyclic to bicyclic) aromatic ring, for example, phenyl, 1-naphthyl, 2-naphthyl, 1-anthryl, or 2-anthryl, unless otherwise specified. The six- to fourteen-membered aryl contains six to fourteen carbon atoms in the ring system.

Unless otherwise specified, the term "heterocyclic group" or "heterocyclic ring" as used herein may be a saturated, partially saturated, or unsaturated monocyclic or bicyclic heterocyclic ring which contains one to four heteroatoms selected from nitrogen, oxygen, and sulfur atoms with the remaining ring atoms being carbon atoms and wherein each ring is a four- to seven-membered (preferably five- to seven-membered, more preferably five- or six-membered) ring. Examples of these heterocyclic groups include azetidino, pyrrolyl, pyrrolidinyl, pyrrolidino, furyl, thienyl, imidazolyl, isoxazolyl, oxazolyl, thiazolyl, isothiazolyl, triazolyl, thiadiazolyl, oxadiazolyl, tetrazolyl, pyridyl, pyrazolyl, pyrimidyl, pyrazinyl, piperazinyl, piperazino, piperidino, morpholinyl, morpholino, thiomorpholino, pyrazinyl, quinolyl, chromenyl, benzoxazolyl, benzothiazolyl, thiazolopyridyl, thiazolopyrimidinyl, and imidazothiazolyl wherein the binding position is not particularly limited.

The optionally substituted aryl represented by A is preferably optionally substituted phenyl, more preferably phenyl. The substituent by which the aryl group may be substituted is preferably selected from the group consisting of halides, cyano, and $C_{1-6}$ alkyloxy and is more preferably selected from the group consisting of halides, cyano, and $C_{1-2}$ alkyloxy.

The heterocyclic group represented by A is preferably a monocylic heterocyclic group and is more preferably a four- to six-membered heterocylic group containing one S or N atom as a heteroatom, a five- or six-membered unsaturated heterocyclic group containing two or three N atoms as a heteroatom, or a five-membered unsaturated heterocyclic group containing an O or S atom and two N atoms as a heteroatom. The heterocyclic group is more preferably azetidinyl, thienyl, imidazolyl, thiazolyl, 1,3,4-thiadiazolyl, 1,2,4-thiadiazolyl, 1,3,4-oxadiazolyl, 1,2,4-triazolyl, pyridyl, pyrimidinyl, benzoxazolyl, benzothiazolyl, or oxazolyl, still more preferably thienyl, oxazolyl, 1,3,4-thiadiazolyl, 1,3,4-oxadiazolyl, pyridyl, or pyrimidinyl, particularly preferably pyridyl.

More specifically, the heterocyclic group represented by A is typically 2-azetidinyl, 2-thienyl, 2-imidazolyl, (2- or 5-)thiazolyl, 2-oxazolyl, 1,3,4-thiadiazol-2-yl, 1,2,4-thiadiazol-5-yl, 1,3,4-oxadiazol-2-yl, 1,2,4-triazol-3-yl, 2-pyridyl, 3-pyridyl, 2-pyrimidinyl, 5-pyrimidinyl, 2-benzothiazolyl, or 2-benzoxazolyl, preferably 2-thienyl, 1,3,4-thiadiazol-2-yl, 1,3,4-oxadiazol-2-yl, 2-pyridyl, 3-pyridyl, 2-pyrimidinyl, 5-pyrimidinyl, or 2-oxazolyl.

In a preferred embodiment of the present invention, A represents aryl optionally substituted by one or more groups selected from the group consisting of halides, cyano, and $C_{1-6}$ alkyloxy, or a four- to six-membered monocyclic heterocyclic group, wherein the heterocyclic group is selected from the group consisting of thienyl, 1,3,4-thiadiazolyl, 1,3,4-oxadiazolyl, pyridyl, pyrimidinyl, and oxazolyl. More preferably, A represents phenyl.

In pyridyl-$CHR_8$— represented by $R_1$, preferably, $R_8$ represents hydroxyl or $C_{1-4}$ alkyloxy, more preferably hydroxyl, methyloxy, or ethyloxy, still more preferably methyloxy.

The optionally substituted arylthio represented by $R_1$ is preferably arylthio optionally substituted by nitro, more preferably phenyl optionally substituted by nitro.

The optionally substituted aryl represented by $R_1$ is preferably optionally substituted phenyl. The substituent in the aryl group is one or more groups, which may be the same or different, selected from a fluorine atom, a chlorine atom, nitro, amino, $C_{1-6}$ alkyl, and $C_{1-6}$ alkyloxy, and is more preferably selected from nitro, amino, $C_{1-6}$ alkyl, and $C_{1-6}$ alkyloxy.

The optionally substituted five- to seven-membered monocyclic heterocyclic group represented by $R_1$ is preferably a five- or six-membered heterocyclic group and is more preferably selected from the group consisting of pyridyl, furyl, pyrazolyl, imidazolyl, dihydroimidazolyl, pyrrolidinyl, dihydropyrrolyl, 1,3-oxazolidinyl, tetrazolyl, thiazolyl, 1,2,3-thiadiazolyl, 1,3,4-thiadiazolyl, 1,3,5-triazinyl, 1,3,4-triazolyl, pyrimidinyl, 1,2-oxazolyl, 1,3-oxazolyl, pyrazinyl, morpholinyl, piperidinyl, piperazinyl, tetrahydropyridazinyl, tetrahydropyridyl, 1,4-oxazepanyl, azepanyl, tetrahydroazepinyl, and 1,4-diazepanyl.

More specifically, the optionally substituted five- to seven-membered monocyclic heterocyclic group represented by $R_1$ is pyridyl, imidazolyl, dihydroimidazolyl, pyrrolidinyl, 1,3-oxazolidinyl, thiazolyl, 1,2,3-thiadiazolyl, 1,3,4-thiadiazolyl, 1,3,5-triazinyl, pyrimidinyl, 1,2-oxazolyl, 1,3-oxazolyl, pyrazinyl, morpholinyl, piperidinyl, piperazinyl, tetrahydropyridazinyl, or tetrahydropyridyl, more preferably (2-, 4- or 5-)thiazolyl, 1,2,3-thiadiazol-4-yl, 1,2,3-thiadiazol-5-yl, 1,3,4-thiadiazol-2-yl, 1-pyrrolidinyl, 1,3-oxazolidin-3-yl, (2-, 3- or 4-)pyridyl, 2-pyrazinyl, 1,2,3-triazol-1-yl, 1,2,3-triazol-2-yl, 1,2,4-triazol-1-yl, 1,2,4-triazol-2-yl, imidazol-1-yl, 3-dihydroimidazolyl, 2-pyrimidinyl, 5-pyrimidinyl, 1,3-oxazol-5-yl, 1,2-oxazol-5-yl, 1,3,5-triazin-2-yl, 2-morpholinyl, piperazino, 3-piperidinyl, 4-piperidinyl, 3-tetrahydropyridyl, or 6-tetrahydropyridazinyl, still more preferably 2-pyrazinyl, 5-pyrimidinyl, 1,3,5-triazin-2-yl, 1,2,3-thiadiazol-4-yl, 3-pyridyl, 2-morpholinyl, 3-piperidinyl, imidazol-1-yl, or 3-tetrahydropyridyl, particularly preferably 5-pyrimidinyl, 3-tetrahydropyridyl.

The five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide.

The substituent in the heterocyclic group is preferably a halide, nitro, cyano, $C_{1-6}$ alkylamino, di-$C_{1-6}$ alkylamino, acyl, $C_{1-6}$ alkyloxy, hydroxy-$C_{1-6}$ alkyl, hydroxy-$C_{1-6}$ alkyl, di-$C_{1-6}$ alkylamino-$C_{1-6}$ alkyl, acylamino-$C_{1-6}$ alkyl, amino, thioxo, carbamoyl, di-$C_{1-6}$ alkylaminocarbonyl, $C_{1-6}$ alkyloxy-$C_{1-6}$ alkyl, or N-oxide.

The bicyclic heterocyclic group represented by $R_1$ is preferably a group selected from the group consisting of quinoline, quinazoline, benzoxazole, and benzothiazole, more preferably 3-quinolinyl or 2-benzoxazolyl.

In a preferred embodiment of the present invention, $R_1$ represents pyridyl-$CHR_8$— wherein $R_8$ is as defined in formula (I); morpholinocarbonyl; arylthio optionally substituted by nitro; optionally substituted aryl in which the aryl group is optionally substituted by one or more groups, which may be the same or different, selected from the group consisting of nitro, amino, and $C_{1-6}$ alkyloxy; an optionally substituted five- to seven-membered monocyclic heterocyclic group in which the five- to seven-membered heterocyclic group is a group selected from the group consisting of pyridyl, imidazolyl, dihydroimidazolyl, pyrrolidinyl, thiazolyl, 1,2,3-thiadiazolyl, 1,3,4-thiadiazolyl, 1,3,5-triazinyl, pyrimidinyl, 1,2-oxazolyl, 1,3-oxazolyl, pyrazinyl, morpholinyl, piperidinyl, piperazinyl, tetrahydropyridazinyl, and tetrahydropyridyl, and the heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, amino, oxo, thioxo, carbamoyl, di-$C_{1-6}$ alkylaminocarbonyl, $C_{1-6}$ alkyloxy-$C_{1-6}$ alkyl, and N-oxide.

More preferably, $R_1$ represents optionally substituted aryl or an optionally substituted five- or six-membered monocyclic heterocyclic group.

Still more preferably, $R_1$ represents an optionally substituted a five- or six-membered monocyclic heterocyclic group.

In a preferred embodiment of the present invention, regarding a combination of A with $R_1$, when A represents optionally substituted aryl, $R_1$ represents an optionally substituted five- or six-membered monocyclic heterocyclic group; or when A represents an optionally substituted four- to six-membered monocyclic heterocyclic group, $R_1$ represents optionally substituted aryl or an optionally substituted five- or six-membered monocyclic heterocyclic group. In a more preferred embodiment of the present invention, regarding $R_1$-A-, $R_1$ and A each represent optionally substituted 5-pyrimidinyl-phenyl- or 3-tetrahydropyridyl-phenyl-.

In a preferred embodiment of the present invention, preferably, $R_2$ represents a hydrogen atom; $C_{1-6}$ alkyl optionally substituted by hydroxyl; acyl; $C_{1-6}$ alkylcarbonylaminomethyl; $C_{1-6}$ alkylcarbonyloxymethylcarbonyl; (5-methyl-1,3-dioxole-2-oxo-4-yl)methyl; (5-methyl-1,3-dioxole-2-oxo-4-yl)methyloxycarbonyl; $C_{1-6}$ alkyloxycarbonyl; or aryloxycarbonyl.

More preferably, $R_2$ represents a hydrogen atom or $C_{1-6}$ alkyl.

In a preferred embodiment of the present invention, $R_3$ represents optionally substituted $C_{1-6}$ alkyl or $C_{3-6}$ cycloalkyl-$C_{1-4}$ alkyl, more preferably $C_{1-6}$ alkyl or $C_{3-6}$ cycloalkyl-$C_{1-4}$ alkyl, still more preferably $C_{3-6}$ cycloalkyl-$C_{1-4}$ alkyl, particularly preferably cyclopropylmethyl.

In a preferred embodiment of the present invention, $R_4$, $R_5$, and $R_6$, which may be the same or different, represent a hydrogen atom or optionally substituted $C_{1-6}$ alkyl, more preferably a hydrogen atom, methyl, or ethyl, still more preferably each a hydrogen atom.

In a preferred embodiment of the present invention, $R_7$ represents $C_{1-6}$ alkyl, more preferably $C_{1-4}$ alkyl, still more preferably methyl or ethyl, particularly preferably methyl.

m is preferably 1 or 2.

In one preferred embodiment of the present invention,

A represents benzyl in which methylene in the benzyl group is bonded to S;

aryl optionally substituted by one or more groups selected from the group consisting of $C_{1-6}$ alkyl, halides, cyano, and $C_{1-6}$ alkyloxy; or a monocyclic or dicyclic heterocyclic group in which each of the rings has four to six members and which is optionally substituted by one or more groups selected from the group consisting of $C_{1-6}$ alkyl and $C_{1-6}$ alkyl halides wherein the heterocyclic group is selected from the group consisting of azetidinyl, thienyl, imidazolyl, thiazolyl, 1,3,4-thiadiazolyl, 1,2,4-thiadiazolyl, 1,3,4-oxadiazolyl, 1,2,4-triazolyl, pyridyl, pyrimidinyl, benzoxazolyl, benzothiazolyl, and oxazolyl, and $R_1$ represents pyridyl-$CHR_8$— wherein $R_8$ represents hydroxyl or $C_{1-6}$ alkyloxy;

morpholinocarbonyl;

arylthio optionally substituted by one or more groups selected from the group consisting of $C_{1-6}$ alkyl, halides, cyan, and nitro;

optionally substituted aryl wherein aryl is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, $C_{1-6}$ alkyloxy halide, hydroxy-$C_{1-6}$ alkyl, hydroxy-$C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;

an optionally substituted five- to seven-membered monocyclic heterocyclic group wherein the five- to seven-membered heterocyclic group is a group selected from the group consisting of pyridyl, furyl, pyrazolyl, imidazolyl, dihydroimidazolyl, pyrrolidinyl, dihydropyrrolyl, 1,3-oxazolidinyl, tetrazolyl, thiazolyl, 1,2,3-thiadiazolyl, 1,3,4-thiadiazolyl, 1,3,5-triazinyl, 1,3,4-triazolyl, pyrimidinyl, 1,2-oxazolyl, 1,3-oxazolyl, pyrazinyl, morpholinyl, piperidinyl, piperazinyl, tetrahydropyridazinyl, tetrahydropyridyl, 1,4-oxazepanyl, azepanyl, tetrahydroazepinyl, and 1,4-diazepanyl, and the five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or a dicyclic heterocyclic group in which each of the rings has four to six members wherein the dicyclic heterocyclic group is a group selected from the group consisting of quinoline, quinazoline, benzoxazole, and benzothiazole.

In one preferred embodiment of the present invention,

A represents optionally substituted aryl; or an optionally substituted monocyclic or dicyclic heterocyclic group in which each of the rings has four to six members, $R_1$ represents
pyridyl-$CHR_8$— wherein $R_8$ represents hydroxyl or $C_{1-6}$ alkyloxy;
morpholinocarbonyl
optionally substituted arylthio;
optionally substituted aryl; or
an optionally substituted five- to seven-membered monocyclic heterocyclic group, and
$R_3$ represents
optionally substituted $C_{1-6}$ alkyl; or
$C_{3-6}$ cycloalkyl-$C_{1-4}$ alkyl.

In one preferred embodiment of the present invention,
A represents
phenyl optionally substituted by one more groups selected from the group consisting of halides, cyano, and $C_{1-6}$ alkyloxy; or
a four- to six-membered monocyclic heterocyclic group in which the heterocyclic group is selected from the group consisting of thienyl, 1,3,4-thiadiazolyl, 1,3,4-oxadiazolyl, pyridyl, pyrimidinyl, and oxazolyl,
$R_1$ represents
pyridyl-$CHR_8$— wherein $R_8$ represents hydroxyl or $C_{1-6}$ alkyloxy;
morpholinocarbonyl;
phenylthio optionally substituted by nitro;
optionally substituted phenyl
wherein the phenyl group is optionally substituted by one or more groups, which may be the same or different, selected from the group consisting of nitro, amino, $C_{1-6}$ alkyl, and $C_{1-6}$ alkyloxy; or
an optionally substituted five- to seven-membered monocyclic heterocyclic group
wherein the five- to seven-membered heterocyclic group is a group selected from the group consisting of pyridyl, imidazolyl, dihydroimidazolyl, pyrrolidinyl, thiazolyl, 1,2,3-thiadiazolyl, 1,3,4-thiadiazolyl, 1,3,5-triazinyl, pyrimidinyl, 1,2-oxazolyl, 1,3-oxazolyl, pyrazinyl, morpholinyl, piperidinyl, piperazinyl, tetrahydropyridazinyl, and tetrahydropyridyl, and
the five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, amino, oxo, thioxo, carbamoyl, di-$C_{1-6}$ alkylaminocarbonyl, $C_{1-6}$ alkyloxy-$C_{1-6}$ alkyl, and N-oxide; and
$R_3$ represents
$C_{1-6}$ alkyl; or
$C_{3-6}$ cycloalkyl-$C_{1-4}$ alkyl.

In the above case, in one preferred embodiment of the present invention,
$R_2$ represents
a hydrogen atom;
$C_{1-6}$ alkyl optionally substituted by hydroxy;
acyl;
$C_{1-4}$ alkylcarbonylaminomethyl;
$C_{1-4}$ alkylcarbonyloxymethylcarbonyl;
(5-methyl-1,3-dioxole-2-oxo-4-yl)methyl;
(5-methyl-1,3-dioxole-2-oxo-4-yl)methyloxycarbonyl;
$C_{1-6}$ alkyloxycarbonyl; or
aryloxycarbonyl,
$R_4$, $R_5$, and $R_6$ each represent a hydrogen atom, and
$R_7$ represents $C_{1-4}$ alkyl.

Asymmetric carbon, to which —S-A-($R_1$)$_n$ is bonded, is present in the molecule of the compound of formula (I) according to the present invention, and the present invention includes any isolated substance in the stereoisomers and a mixture of the stereoisomers. The carbon preferably has an S configuration. In a preferred embodiment of the present invention, a group of compounds of formula (II) and pharmacologically acceptable salts or solvates thereof may be mentioned.

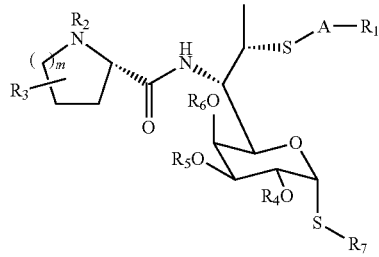

(II)

wherein A, $R_1$, $R_2$, $R_3$, $R_4$, $R_5$, $R_6$, $R_7$, and m are as defined in formula (I).

In another embodiment of the present invention, there are provided compounds of formula (I) or pharmacologically acceptable salts or solvates thereof, wherein A, $R_1$, $R_2$, $R_3$, $R_4$, $R_5$, $R_6$, $R_7$, and m are as defined below.

Specifically, in formula (I),
A represents benzyl in which methylene in the benzyl group is bonded to S;
aryl optionally substituted by one or more groups selected from the group consisting of $C_{1-6}$ alkyl, halides, cyano, and $C_{1-6}$ alkyloxy; or
a monocyclic or dicyclic heterocyclic group in which each of the rings has four to six rings and which is optionally substituted by a group selected from the group consisting of $C_{1-6}$ alkyl and $C_{1-6}$ alkyl halide
wherein the heterocyclic ring is selected from the group consisting of azetidinyl, thienyl, imidazolyl, thiazolyl, 1,3,4-thiadiazolyl, 1,2,4-thiadiazolyl, 1,3,4-oxadiazolyl, 1,2,4-triazolyl, pyridyl, pyrimidinyl, benzoxazolyl, benzothiazolyl, and oxazolyl.

$R_1$ represents pyridyl-$CHR_8$— wherein $R_8$ represents hydroxyl or $C_{1-6}$ alkyloxy;
morpholinocarbonyl;
arylthio optionally substituted by nitro;
optionally substituted aryl
wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, $C_{1-6}$ alkyloxy halide, hydroxy-$C_{1-6}$ alkyl, hydroxy-$C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;
optionally substituted five- to seven-membered monocyclic heterocyclic group
wherein the five- to seven-membered heterocyclic group is selected from the group consisting of pyridyl, furyl (for example, 2-furyl), pyrazolyl (for example, 4-pyrazolyl), imidazolyl, dihydroimidazolyl, pyrrolidinyl, dihydropyrrolyl, 1,3-oxazolidinyl, tetrazolyl (for example, tetrazol-1-yl, tetrazol-2-yl), thiazolyl, 1,2,3-thiadiazolyl, 1,3,4-thiadiazolyl, 1,3,5-triazinyl, 1,3,4-triazolyl, pyrimidinyl, 1,2-oxazolyl, 1,3-oxazolyl, pyrazinyl, morpholinyl, piperidinyl, piperazinyl, tetrahydropyridazinyl, tetrahydropyridyl, 1,4-oxazepanyl, azepanyl, tetrahydroazepinyl, and 1,4-diazepanyl, and the heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or a dicyclic heterocyclic group in which each of the groups has four to six members wherein the dicyclic heterocyclic group is selected from the group consisting of quinoline, quinazoline, benzoxazole, and benzothiazole, $R_2$ represents a hydrogen atom;
optionally substituted $C_{1-6}$ alkyl;
optionally substituted $C_{2-6}$ alkenyl;
optionally substituted acyl;
$C_{1-6}$ alkylcarbonylaminomethyl;
$C_{1-6}$ alkylcarbonyloxymethylcarbonyl;
(5-methyl-1,3-dioxol-2-oxo-4-yl)methyl;
(5-methyl-1,3-dioxol-2-oxo-4-yl)methyloxycarbonyl;
optionally substituted $C_{1-6}$ alkyloxycarbonyl wherein the $C_{1-6}$ alkyl, $C_{2-6}$ alkenyl, acyl, and $C_{1-6}$ alkyloxycarbonyl are optionally substituted by one or more groups selected from the group consisting of heterocyclic rings optionally substituted by $C_{1-6}$ alkyl; amino; hydroxy; and cyano, or aryloxycarbonyl $R_3$ represents optionally substituted $C_{1-6}$ alkyl wherein the $C_{1-6}$ alkyl group is optionally substituted by one or more groups selected from the group consisting of halides, nitro, hydroxy, amino, $C_{1-6}$ alkyloxycarbonyl, carbamoyl, cyano, $C_{1-6}$ alkyloxy, oxo, heterocyclic rings, azide, $C_{1-6}$ alkylaminocarbonyl, and di-$C_{1-6}$ alkylaminocarbonyl, and optionally substituted aryl;

$C_{3-6}$ cycloalkyl-$C_{1-4}$ alkyl; or
$C_{2-6}$ alkenyl, $R_4$, $R_5$, and $R_6$, which may be the same or different, represent a hydrogen atom;
optionally substituted $C_{1-6}$ alkyl;
optionally substituted acyl wherein hydrogen atoms on the $C_{1-6}$ alkyl and acyl groups are optionally substituted by one or more groups that are selected from the group consisting of halides; nitro; hydroxy; amino; $C_{1-6}$ alkyloxycarbonyl; carbamoyl; cyano; nitrohalide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy, or $C_{1-4}$ alkyl; or benzoyl, $R_7$ represents $C_{1-6}$ alkyl optionally substituted by one or more groups selected from the group consisting of halides and hydroxy, m is 1 to 3, provided that when $R_3$ represents optionally substituted $C_{1-6}$ alkyl or $C_{2-6}$ alkenyl, in $R_1$-A-, $R_1$ and A each represent a group selected from the group consisting of optionally substituted 5-pyrimidinyl-phenyl-, 2-pyrimidinyl-phenyl-, 3-piperidinyl-phenyl-, 4-piperidinyl-phenyl-, 3-tetrahydropyridyl-phenyl-, 2-pyrazinyl-phenyl-, 6-tetrahydropyridazinyl-phenyl-, 1,2-oxazol-5-yl-phenyl-, 1,3-oxazolidin-3-yl-phenyl-, 1,2,3-thiadiazol-4-yl-phenyl, 1,3,4-thiadiazol-2-yl-phenyl, 2-(3-piperidinyl)-pyridin-3-yl, 1,3-oxazol-5-yl-phenyl-, phenylthio-phenyl-, $C_{1-6}$ alkyloxy(pyridyl)methyl-phenyl-, hydroxy(pyridyl)methyl-phenyl-, thiazol-4-yl-phenyl-, thiazol-2-yl-phenyl-, 1-piperazinyl-phenyl-, 1-pyrrolidinyl-phenyl-, 1-dihydroimidazolyl-phenyl-, 2-(1,3-oxazol-5-yl)-thiophen-4-yl-, 2-(pyrimidin-5-yl)-thiophen-4-yl, 3-(pyrimidin-5-yl)-pyridin-6-yl, 2-(pyrimidin-5-yl)-pyridin-5-yl, 2-(tetrahydropyridin-3-yl)-pyridin-5-yl, 2-(pyrrolidin-1-yl)-pyridin-5-yl, 5-(pyrimidin-5-yl)-pyrimidin-2-yl, and 2-(pyrimidin-5-yl)-pyrimidin-5-yl.

The compounds according to the present invention may form pharmacologically acceptable salts thereof. Preferred examples of such salts include: alkali metal or alkaline earth metal salts such as sodium salts, potassium salts, or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherates.

Use of Compounds/pharmaceutical Composition

The compounds according to the present invention can inhibit the growth of bacteria, particularly resistant pneumococci, in vitro and actually exhibit antimicrobial activity (see Test Example 1).

The compounds according to the present invention are lincosamide derivatives having a very high level of antimicrobial activity against various bacteria, for example, resistant bacteria-containing pneumococci (S. pneumoniae). The compounds according to the present invention are lincosamide derivatives and thus have antimicrobial activity against various bacteria, which have hitherto been reported, and, at the same time, have potent antimicrobial activity against resistant pneumococci which pose a clinical problem. Accordingly, the compounds according to the present invention can be said to be very useful for the prevention or treatment of various microbisms including infectious diseases in respiratory organs.

Accordingly, the compounds according to the present invention can be used for the prevention or treatment of microbisms. Such microbisms include, for example, pneumonia, chronic bronchitis, acute otitis media, and acute sinusitis.

According to the present invention, there is provided a pharmaceutical composition comprising the compound according to the present invention or its pharmacologically acceptable salt or solvate and a pharmaceuticially acceptable carrier. In a preferred embodiment of the present invention, there are provided pharmaceutical compositions comprising the above compound as an active ingredient together with an additive for a pharmaceutical preparation. These pharmaceutical compositions are useful for the prevention or treatment of microbisms (preferably microbisms in respiratory organs) and can be used as antimicrobial agents (that is, antimicrobial compositions).

According to another aspect of the present invention, there is provided an antimicrobial agent comprising the compound according to the present invention or its pharmacologically acceptable salt or solvate as active ingredient.

According to still another aspect of the present invention, there is provided a method for treating bacterial infectious diseases, comprising administering a therapeutically effective amount of the compound according to the present invention or its pharmacologically acceptable salt or solvate together with a pharmaceutically acceptable carrier to a mammal.

According to a further aspect of the present invention, there is provided use of the compound according to the present invention or its pharmacologically acceptable salt or solvate for the production of a pharmaceutical composition for treating bacterial infectious diseases. According to a still further aspect of the present invention, there is provided use of the compound according to the present invention or its pharmacologically acceptable salt or solvate as an active ingredient of an antimicrobial agent.

In this case, the bacterial infectious diseases are preferably those in respiratory organs.

The term "treatment" as used herein generally means the attainment of desired pharmacological effect and/or physiological effect. The effect is prophylactical in that a disease and/or a symptom is completely or partly prevented, and is therapeutical in that a disease and/or an adverse effect caused by a disease is partly or completely cured. The term "treatment" as used herein includes any treatment of diseases of mammals, particularly humans and, for example, includes the following treatments (a) to (c):

(a) preventing the onset of a disease or a symptom in a patient who may have a predisposition for a disease or a symptom but not diagnosed as having the disease or symptom;

(b) inhibiting a symptom of a disease, that is, inhibiting or delaying the progress of the symptom; and (c) alleviating a symptom of a disease, that is, causing the regression of a disease or a symptom or the reversal of the progress of a symptom.

The compounds according to the present invention can be administered to human and non-human animals orally or parenterally by administration routes, for example, intravenous administration, intramuscular administration, subcutaneous administration, rectal administration, or percutaneous administration.

Therefore, the pharmaceutical composition comprising a compound according to the present invention may be formulated into suitable dosage forms according to the administration routes. Specifically, oral preparations include tablets, capsules, powders, granules, pills, subtilized granules, troches, and syrups. Parenteral preparations include injections such as intravenous injections or intramuscular injections, suppositories, tapes, and ointments.

These various preparations may be prepared by conventional methods, for example, with pharmaceutically acceptable additives (carriers), that is, commonly used excipients, extenders, disintegrants, binders, lubricants, colorants, diluents, wetting agents, surfactants, dispersants, buffer agents, preservatives, solubilizers, antiseptics, flavoring agents, soothing agents, and stabilizers.

Excipients include, for example, lactose, fructose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose or its salts, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils. Other nontoxic additives usable herein include, for example, syrup, vaseline, lanoline, glycerin, ethanol, propylene glycol, citric acid, sodium chloride, sodium sulfite, sodium phosphate, β-cyclodextrin, hydroxypropyl-β-cyclodextrin, and Tween 80.

In preparing the above injections, if necessary, for example, buffering agents, pH adjustors, stabilizers, tonicity adjusting agents, and preservatives may be added.

The content of a compound according to the present invention in the pharmaceutical composition according to the present invention may vary according to the dosage form. The content, however, is generally 10 to 95% by weight, preferably 30 to 80% by weight, based on the whole composition.

The dose may be appropriately determined in consideration of particular conditions, for example, the age, weight, sex, type of disease, and severity of condition of patients. For example, for the treatment of infectious diseases induced by pneumococci, the pharmaceutical composition can be generally administered, for example, through an oral route at a dose of about 1 to 2000 mg, preferably 10 to 1000 mg per adult per day, in terms of the weight of the compound according to the present invention. This dose may be administered at a time daily or divided doses of two to six times daily depending upon the symptom.

Compounds according to the present invention may be administered in combination with other medicaments, for example, other antimicrobial agents, for example, penicillin, carbapenem, and quinolone. The administration can be carried out simultaneously or sequentially. The kind, administration interval and the like of other medicaments can be determined by taking into consideration the kind of symptoms and the conditions of the patient.

Production of Compounds of Formula (I)

The compounds of formula (I) according to the present invention may be produced according to production processes which will be described later. The production process of the compound according to the present invention is not limited to these production processes. The compounds of the present invention are not limited to the compounds produced by the following production processes. Specific examples of the production process of compounds according to the present invention are described in the working examples of the present specification. Accordingly, all the compounds of formula (I) can easily be produced by a person having ordinary skill in the art by properly selecting starting compounds, reaction conditions, reagents and the like while referring to the following general description of production process and detailed description of the working examples and, if necessary, by conducting proper modification or improvement. The production process of the present invention includes all of processes for producing compounds based on the properties of the compounds clarified by the present invention by conventional means.

In the following description, characters of A, $R_1$ to $R_7$, and m in structural formulae are as defined in formula (I). It should be noted that B and $R_9$ to $R_{11}$ mean a partial structure in $R_1$ and thus are not beyond the range defined in formula (I). Regarding additional characters, other than those in formula (I), which appear as needed, the meaning will be defined in each case, and, when the defined character appears after that, the definition is applied. Further, it should be noted that, in all the following reaction steps, the reaction step identified with the same number is carried out under the same reaction conditions.

At the outset, a group of compounds of formula (I), wherein $R_2$ represents methyl (hereinafter abbreviated to "Me"), $R_3$ represents propyl (hereinafter abbreviated to "Pr"), $R_4$, $R_5$, and $R_6$ represent a hydrogen atom (hereinafter abbreviated to "H"), and m is 1, can be produced, for example, by the following general process.

cess (ii) depending upon whether the reaction reagent used is thiol (HS-A-$R_1$) or disulfide ($R_1$-A-S—S-A-$R_1$). (i) The compound of formula (5) can be produced by conducting a reaction using 1 to 10 equivalents of either the above thiol or the above disulfide in the presence of the compound of formula (3), triphenylphosphine, and diethyl azodicarboxylate in a

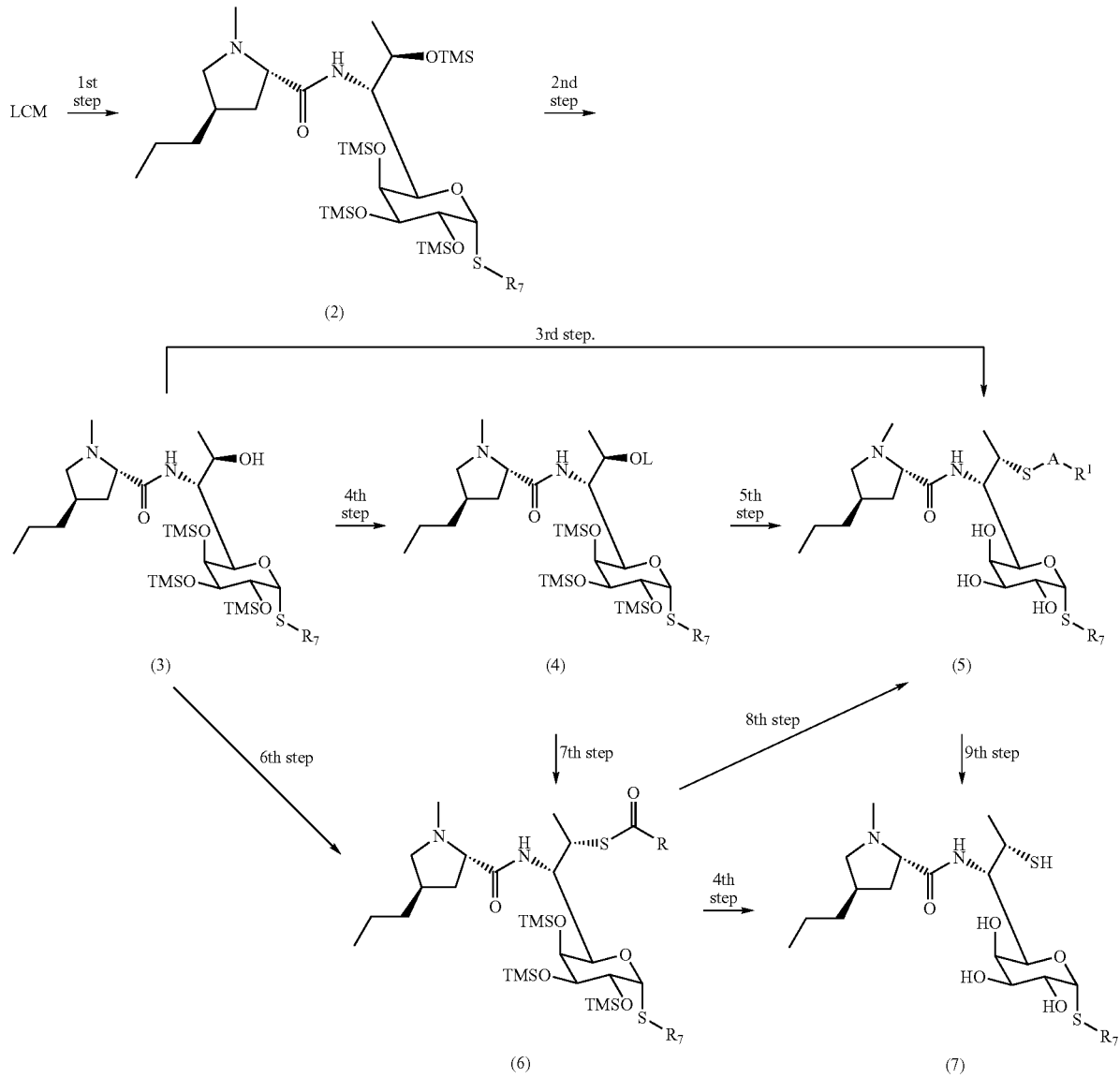

Scheme 1

In formula (4), L represents a leaving group such as $C_{1-6}$ alkylsulfonyl or arylsulfonyl. In formula (6), R represents $C_{1-6}$ alkyl or aryl, and TMS represents trimethylsilyl.

In the first and second steps, the conversion of lincomycin (hereinafter abbreviated to "LCM") to a compound of formula (2) and the conversion of the compound of formula (2) to a compound of formula (3) can be carried out by a process described, for example, in U.S. Pat. No. 3,418,414.

In the third step, the conversion of the compound of formula (3) to the compound of formula (5) can be carried out, for example, by properly selecting either process (i) or process (ii) depending upon whether the reaction reagent used is tetrahydrofuran solution and then removing the trimethylsilyl group, for example, using a diluted hydrochloric acid-methanol solution. Regarding the reaction solvent in this reaction, in addition to tetrahydrofuran, conventional reaction solvents may be used, and preferred examples thereof include benzene, toluene, trifluoromethyl benzene, and acetonitrile. The phosphine reagent may be any phospine reagent commonly known in literatures and the like in addition to triphenylphosphine, preferably tolylphosphine, tri-n-butylphosphine, tri-tert-butylphosphine and the like, and the amount of the phosphine reagent is preferably 1 to 5 equivalents.

The azo reagent may be any azo reagent commonly known in literatures and the like in addition to diethyl azodicarboxylate, preferably diisopropyl azodicarboxylate, 1,1'-(azodicarbonyl)dipiperidine and the like, and the amount of the azo reagent is preferably 1 to 5 equivalents. The reaction temperature is 0 to 50° C., and the reaction time is 0.5 to 24 hr. (ii) The compound of formula (5) can be produced by reacting the above thiol in the presence of the compound of formula (3) and cyanomethylene tri-n-butylphosphorane in a benzene solution and then removing the trimethylsilyl group, for example, using a diluted hydrochloric acid-methanol solution. Regarding the reaction solvent in this reaction, in addition to benzene, conventional reaction solvents may be used, and preferred examples thereof include tetrahydrofuran, toluene, trifluoromethyl benzene, and acetonitrile. The reaction accelerator may be, for example, phosphinylide commonly known in literatures and the like in addition to cyanomethylene tri-n-butylphosphorane, and preferred examples thereof include cyanomethylenetrimethylphosphorane. The amount of the reaction accelerator is preferably 1 to 5 equivalents. The reaction temperature is 0 to 150° C., and the reaction time is 0.5 to 24 hr.

In the fourth step, the conversion of the compound of formula (3) to the compound of formula (4) can be carried out, for example, by the following process. Specifically, the compound of formula (4) can be produced by reacting the compound of formula (3) with a sulfonylating agent in a chloroform solvent in the presence of a base. The reaction solvent in this reaction may be a conventional reaction solvent in addition to chloroform, and preferred examples thereof include halogenic solvents such as methylene chloride and carbon tetrachloride, and polar solvents such as dimethylsulfoxide, pyridine, and 1-methylpyrrolidone. The base is a commonly known inorganic base or organic base, and preferred examples thereof include potassium carbonate, sodium hydrogencarbonate, triethylamine, diisopropylethylamine, and pyridine. The amount of the base is preferably 1 to 10 equivalents. The sulfonylating agent refers to conventional sulfonylating agents, that is, alkylsulfonyl chloride, arylsulfonyl chloride, or sulfonic anhydride, and preferred examples thereof include methanesulfonyl chloride, toluenesulfonyl chloride, and trifluoromethanesulfonic anhydride. The amount of the sulfonylating agent is preferably 1 to 10 equivalents. The reaction temperature is −10 to 50° C., and the reaction time is 0.5 to 24 hr.

In the fifth step, the conversion of the compound of formula (4) to the compound of formula (5) can be carried out, for example, by the following process. Specifically, the compound of formula (5) can be produced by reacting the compound of formula (4) with 1 to 10 equivalents of the above thiol in an N,N-dimethylformamide solvent in the presence of a base and then removing the trimethylsilyl group, for example, using a diluted hydrochloric acid-methanol solution. The reaction solvent in this reaction may be a conventional reaction solvent in addition to N,N-dimethylformamide, and preferred examples thereof include polar solvents such as dimethylsulfoxide, pyridine, and 1-methylpyrrolidone. The base is a commonly known inorganic base or organic base, and preferred examples thereof include potassium carbonate, sodium hydrogencarbonate, triethylamine, diisopropylamine, and pyridine. The amount of the base is preferably 1 to 10 equivalents. The reaction temperature is −10 to 120° C., and the reaction time is 0.5 to 24 hr.

In the sixth step, the conversion of the compound of formula (3) to the compound of formula (6) can be carried out, for example, in the same manner as in the third step except that the thiol is changed to 1 to 10 equivalents of a commonly known alkylthio carboxylic acid or a commonly known arylthio carboxylic acid, preferably, for example, thioacetic acid, thiopropionic acid, or thiobenzoic acid.

In the seventh step, for example, the conversion of the compound of formula (4) to the compound of formula (6) can be carried out, for example, in the same manner as in the fifth step except that the thiol is changed to 1 to 10 equivalents of a commonly known alkylthio carboxylic acid or its salt or a commonly known arylthio carboxylic acid or its salt, preferably thioacetic acid, thiopropionic acid or its potassium salt, sodium salt or the like, or thiobenzoic acid or its potassium salt, sodium salt or the like.

In the eighth step, the conversion of the compound of formula (6) to the compound of formula (5) can be carried out, for example, by the following process. Specifically, the compound of formula (5) can be produced by removing the acyl group in the system in a methanol solvent in the presence of a base, reacting this compound, for example, with 1 to 10 equivalents of an alkyl halide, aryl halide, or a heterocyclic halide, and then removing the trimethylsilyl group, for example, using a diluted hydrochloric acid-methanol solution. The reaction solvent in this reaction may be a conventional polar solvent in addition to methanol, and preferred reaction solvents include ethanol, propanol, butanol, N,N-dimethylformamide, dimethylsulfoxide, and 1-methylpyrrolidone. The base may be a commonly known inorganic base, an alkali metal methoxide, or an alkali metal ethoxide, and preferred examples thereof include sodium hydrogencarbonate, potassium carbonate, calcium carbonate, sodium methoxide, and sodium ethoxide. The amount of the base is preferably 1 to 10 equivalents. The reaction temperature is 0 to 120° C., and the reaction time is 0.5 to 24 hr.

In the ninth step, the compound of formula (6) can be converted to the compound of formula (7), for example, by the following process. Specifically, the compound of formula (7) can be produced by removing the trimethylsilyl group in the compound of formula (6), for example, with a diluted hydrochloric acid-methanol solution in a methanol solvent and then deprotecting the acyl group in the compound of formula (6) with a base. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The base may be a commonly known inorganic base, an alkali metal methoxide, or an alkali metal ethoxide, and preferred examples thereof include sodium hydroxide, potassium hydroxide, sodium methoxide, and sodium ethoxide. The amount of the base is preferably 1 to 10 equivalents. The reaction temperature is 0 to 40° C., and the reaction time is 0.5 to 24 hr.

In the tenth step, the conversion of the compound of formula (7) to the compound of formula (5) can be carried out, for example, by properly selecting either process (i) or process (ii). (i) The compound of formula (5) can be produced by reacting the compound of formula (7) with 1 to 10 equivalents of a reactant represented by $X_1$-A-$R_1$, wherein $X_1$ represents an $RSO_2$ group or a halide, in an N,N-dimethylformamide solvent in the presence of a base.

The reaction solvent in this reaction may be a conventional reaction solvent in addition to N,N-dimethylformamide, and preferred examples thereof include dimethylsulfoxide, tetrahydrofuran, diethyl ether, and 1-methylpyrrolidone. The base may be a commonly known inorganic base or organic base, and preferred examples thereof include sodium hydrogencarbonate, sodium carbonate, potassium phosphate, sodium tert-butoxide, potassium tert-butoxide, diisopropylethylamine, or triethylamine. The amount of the base is preferably 1 to 10 equivalents. The reaction temperature may be room temperature to 150° C., and the reaction time is 1 to 24 hr. (ii) The compound of formula (5) can be produced by allowing the compound of formula (7) to react in a dioxane solvent in the presence of a base, a reactant represented by $X_2$-A-$R_1$, wherein $X_2$ represents I, Br, Cl, OTf, or OTs wherein Tf represents trifluoromethanesulfonyl and Ts represents tosyl, an additive, and a conventional palladium catalyst. The reaction solvent in this reaction may be a conventional reaction solvent in addition to dioxane, and preferred examples thereof include N,N-dimethylformamide, benzene, toluene, cyclopentyl methyl ether, tetrahydrofuran, butanol, and dimethylsulfoxide. The base may be a commonly known inorganic base or organic base, and preferred examples thereof include sodium carbonate, potassium phosphate, potassium fluoride, cesium fluoride, sodium tert-butoxide, potassium tert-butoxide, diisopropylethylamine, and triethylamine. The amount of the base is preferably 1 to 10 equivalents. The additive may be a commonly known phosphine ligand, and preferred examples thereof include 4,5-bis(diphenylphosphino)-9,9-dimethylsantene, 2,2'-bis(diphenylphosphino)-1,1'-binaphthyl, triphenylphosphine, and tri-tert-butylphosphine. The amount of the additive is preferably 0.01 to 0.5 equivalent. Preferred examples of palladium catalysts which are generally usable herein include tris(dibenzylideneacetone)dipalladium, palladium acetate, and dichlorobis(diphenylphosphino)ferrocene palladium. In addition to the palladium catalyst, metallic catalysts such as copper catalysts may be used, and the amount of the catalyst is preferably 0.01 to 0.5 equivalent. The reaction temperature is room temperature to 150° C., and the reaction time is 1 to 48 hr.

Secondly, among the compounds of formula (5), a group of compounds wherein $R_1$ represents a five- to seven-membered saturated cyclic amine, where $R_9$ represents a hydrogen atom or $C_{1-6}$ alkyl (formula (8)), cannot be efficiently produced without difficulties by the process shown in scheme 1, for example, for production or purification reasons. The group of compounds (formula (8)) can also be produced by an alternative process, for example, by the following process using a compound of formula (5), wherein $R_1$ represents pyridyl or a five- to seven-membered unsaturated cyclic amine having N—$R_9$ in its ring, produced by the process shown in scheme 1.

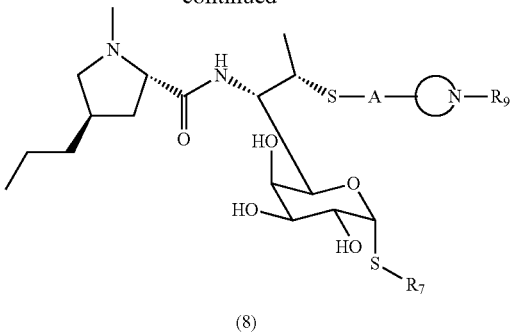

(8)

In the tenth step, the compound of formula (5) can be converted to the compound of formula (8), for example, by properly selecting either processes (i) or (ii). For example, in process (i), the compound of formula (8) can be produced by adding a platinum black catalyst to the compound of formula (5) in the presence of an acid in a methanol solvent and allowing a reaction to proceed in a hydrogen atmosphere. The reaction solvent in this reaction may be a conventional solvent in addition to methanol and preferred examples thereof include ethanol, propanol, and butanol. The acid is preferably acetic acid, hydrochloric acid, sulfuric acid or the like. The reaction temperature is 0 to 120° C., and the reaction time is 6 to 36 hr. In process (ii), the compound of formula (8) can be produced by reacting the compound of formula (5) with 1 to 10 equivalents of 4-methylbenzenesulfohydrazide in a toluene solvent. The reaction solvent in this reaction may be a conventional solvent in addition to toluene, and preferred examples thereof include benzene and tetrahydrofuran solvents. The reaction temperature is 90 to 120° C., and the reaction time is 0.5 to 24 hr.

Thirdly, among the compounds of formula (5), a group of compounds wherein $R_1$ represents —B—$NR_{10}R_{11}$ where B represents optionally substituted aryl or a heterocyclic ring and $R_{10}$ represents a hydrogen atom or $C_{1-6}$ alkyl, or B and $R_{10}$ together form a four- to seven-membered heterocyclic ring, and $R_{11}$ represents $C_{1-6}$ alkyl or acyl (formula (10)) cannot be efficiently produced without difficulties by the process shown in scheme 1, for example, for production or purification reasons. The group of these compounds (formula (10)) can also be produced by an alternative method, for example, by producing the compound of formula (9) as a precursor of the compound of formula (10) by the process shown in scheme 1 or scheme 2 and then subjecting the compound of formula (9) to the following process.

Scheme 2

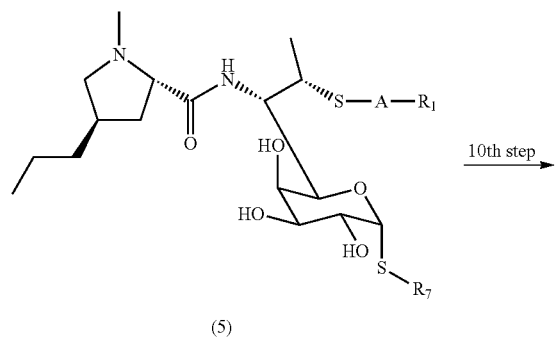

(5)

10th step

Scheme 3

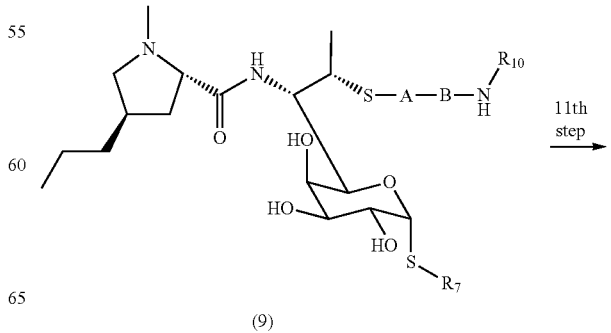

(9)

11th step

-continued

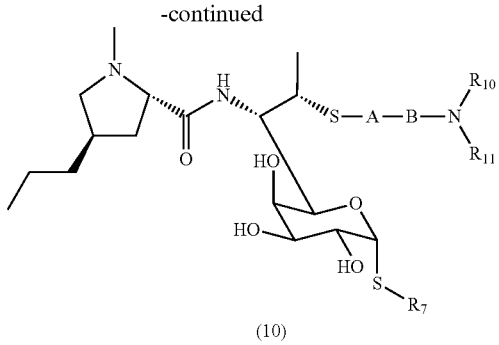

(10)

In the eleventh step, the conversion of the compound of formula (9) to the compound of formula (10) can be carried out, for example, by properly selecting any one of processes (i), (ii), and (iii). For example, in process (i), the compound of formula (10) can be produced by reacting the compound of formula (9) with 1 to 10 equivalents of a ketone or an aldehyde in a 1,2-dichloroethane solvent in the presence of an acid and a reducing agent. The reaction solvent in this reaction may be a conventional solvent in addition to 1,2-dichloroethane, and preferred examples thereof include solvents such as methylene chloride, chloroform, tetrahydrofuran, diethyl ether, methanol, ethanol, and butanol. The acid is preferably acetic acid, hydrochloric acid, sulfuric acid or the like. The reducing agent may be a commonly known reducing agent, and preferred examples thereof include sodium triacetoxyboron. The amount of the reducing agent is preferably 1 to 10 equivalents. The reaction temperature is 0 to 120° C., and the reaction time is 0.5 to 4 hr. In process (ii), the compound of formula (10) can be produced by reacting the compound of formula (9) with 1 to 10 equivalents of an alkyl halide in an acetonitrile solvent in the presence of a base. The reaction solvent in this reaction may be a conventional solvent in addition to acetonitrile, and preferred examples thereof include polar solvents such as N,N-dimethylformamide, dimethylsulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr. In process (iii), the compound of formula (10) can be produced, for example, by reacting the compound of formula (9) with 1 to 10 equivalents of acetic anhydride in a methanol solvent. The reaction solvent in this reaction may be a conventional solvent in addition to methanol, and preferred examples thereof include polar solvents such as ethanol and propanol. The reaction temperature is 0 to 60° C., and the reaction time is 0.5 to 6 hr.

Fourthly, a group of compounds of formula (I), wherein $R_4$, $R_5$, and $R_6$ represent H and m is 1 or 2 can be produced, for example, by the following general process.

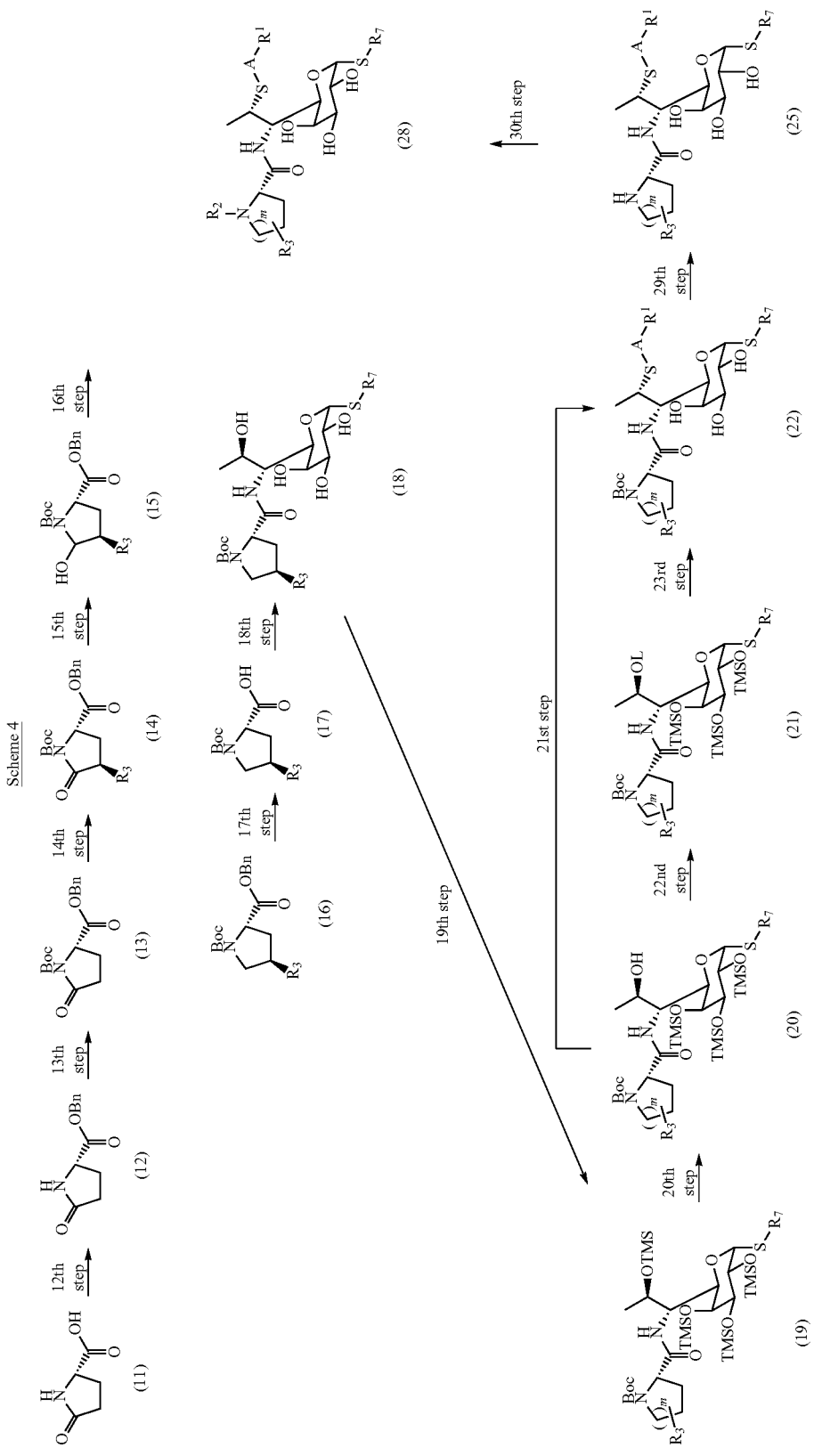

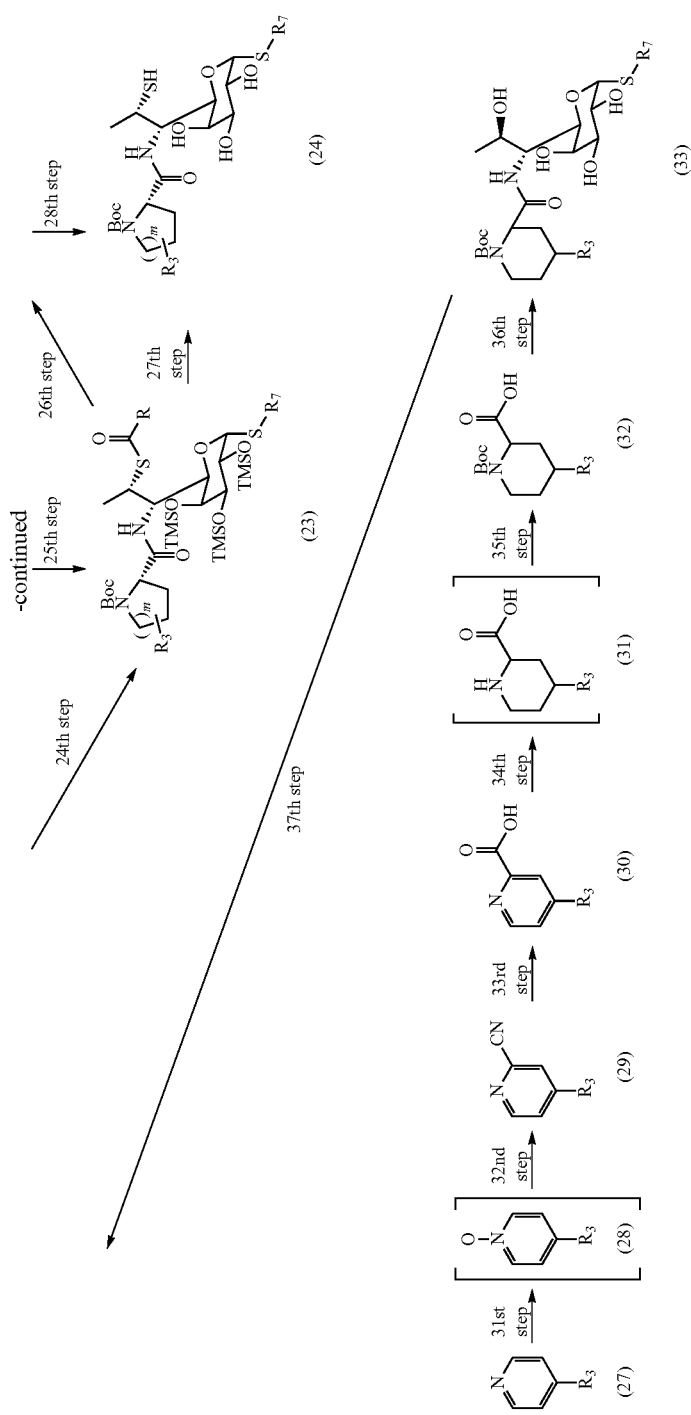

In the twelfth and thirteenth steps, the conversion of the compound of formula (11) to the compound of formula (12) and the conversion of the compound of formula (12) to the compound of formula (13) can be carried out, for example, by the process described in Tetrahedron Lett., 43, (2002), 3499.

In the fourteenth to sixteenth steps, the conversion of the compound of formula (13) to the compound of formula (14), the conversion of the compound of formula (14) to the compound of formula (15), and the conversion of the compound of formula (15) to the compound of formula (16) can be carried out, for example, according to the processes described in Tetrahedron Lett., 35, (1994), 2053 and J. Am. Chem. Soc., 110, (1998), 3894.

In the seventeenth step, the conversion of the compound of formula (16) to the compound of formula (17) can be carried out by properly selecting whether, in $R_3$ in formula (17), the double bond (i) is allowed to remain unremoved or (ii) is removed and subjecting the compound of formula (16) to the following process. For example, in process (i), the compound of formula (17) can be produced by hydrolyzing the compound of formula (16) in a methanol solvent in the presence of a base. The reaction solvent in this reaction may be a conventional alcohol solvent in addition to methanol, and preferred examples thereof include ethanol, propanol, and butanol. The reaction temperature is 0 to 120° C., and the reaction time is 0.5 to 24 hr. In process (ii), the compound of formula (17) can be produced by the process described in J. Am. Chem. Soc., 110, (1998), 3894.

In the eighteenth step, the conversion of the compound of formula (17) to the compound of formula (18) can be carried out, for example, by reacting the compound of formula (17) with 1 to 10 equivalents of methyl 1-thio-α-lincosamide (abbreviated to "MTL") in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as tetrahydrofuran, diethyl ether, dimethylsulfoxide, and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, 1 to 10 equivalents of, for example, a combination of dicyclohexylcarbodiimide with 4-dimethylaminopyridine is used. The reaction temperature is 0 to 120° C., and the reaction time is 0.5 to 24 hr.

In the nineteenth step, the compound of formula (18) can be converted to the compound of formula (19), for example, according to the process described in the first step.

In the twentieth step, the compound of formula (19) can be converted to the compound of formula (20), for example, according to the process described in the second step.

In the twenty-first step, the compound of formula (20) can be converted to the compound of formula (22), for example, according to the process described in the third step.

In the twenty-second step, the compound of formula (20) can be converted to the compound of formula (21), for example, according to the process described in the fourth step.

In the twenty-third step, the compound of formula (21) can be converted to the compound of formula (22), for example, according to the process described in the fifth step.

In the twenty-fourth step, the compound of formula (20) can be converted to the compound of formula (23), for example, according to the process described in the sixth step.

In the twenty-fifth step, the compound of formula (21) can be converted to the compound of formula (23), for example, according to the process described in the seventh step.

In the twenty-sixth step, the compound of formula (23) can be converted to the compound of formula (22), for example, according to the process described in the eighth step.

In the twenty-seventh step, the compound of formula (23) can be converted to the compound of formula (24), for example, according to the process described in the ninth step.

In the twenty-eighth step, the compound of formula (22) can be converted to the compound of formula (24), for example, according to the process described in the tenth step.

In the twenty-ninth step, the compound of formula (22) can be converted to the compound of formula (25), for example, by reacting the compound of formula (22) with either a 95% aqueous trifluoroacetic acid solution or 1 N hydrogen chloride-methanol solution. The reaction temperature is 0 to 50° C., and the reaction time is 0.5 to 24 hr.

In the thirtieth step, the conversion of the compound of formula (25) to the compound of formula (26) can be carried out by properly selecting any one of processes (i), (ii), and (iii). For example, in process (i), the compound of formula (26) can be produced by reacting the compound of formula (25) with 1 to 10 equivalents of a ketone or an aldehyde in a 1,2-dichloroethane solvent in the presence of an acid and a reducing agent. The reaction solvent in this reaction may be a conventional solvent in addition to 1,2-dichloroethane, and preferred examples thereof include solvents such as methylene chloride, chloroform, tetrahydrofuran, diethyl ether, methanol, ethanol, and butanol. The acid is preferably acetic acid, hydrochloric acid, sulfuric acid or the like. The reducing agent may be a commonly known reducing agent, and preferred examples thereof include sodium triacetoxyboron. The amount of the reducing agent is preferably 1 to 10 equivalents. The reaction temperature is 0 to 120° C., and the reaction time is 0.5 to 4 hr. In process (ii), the compound of formula (26) can be produced by reacting the compound of formula (53) with 1 to 10 equivalents of an alkyl halide in an acetonitrile solvent in the presence of a base. The reaction solvent in this reaction may be a conventional solvent in addition to acetonitrile, and preferred examples thereof include polar solvents such as N,N-dimethylformamide, dimethylsulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr. In process (iii), the compound of formula (26) can be produced by reacting the compound of formula (25) with 1 to 10 equivalents of an alkylcarboxylic acid or an arylcarboxylic acid in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as dimethylsulfoxide and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, for example, 1 to 10 equivalents of a combination of dicyclohexylcarbodiimide with 4-dimethylaminopyridine or the like is used. The reaction temperature is 0 to 120° C., and the reaction time is 0.5 to 24 hr.

In the thirty-first to thirty-third steps, the conversion of the compound of formula (27) to the compound of formula (28), the conversion of the compound of formula (28) to the compound of formula (29), and the conversion of the compound of formula (29) to the compound of formula (30) can be carried out, for example, according to the process described in J. Med. Chem., 32, (1989), 829.

In the thirty-fourth step, the conversion of the compound of formula (30) to the compound of formula (31) can be carried out, for example, by adding the compound of formula (30) and platinum oxide to an acetic acid solvent and allowing a reaction to proceed under a hydrogen atmosphere (ordinary pressure). The reaction temperature is 0 to 50° C., and the reaction time is 0.5 to 24 hr.

In the thirty-fifth step, the conversion of the compound of formula (31) to the compound of formula (32) can be carried out according to the process in the sixty-fourth step.

In the thirty-sixth step, the conversion of the compound of formula (32) to the compound of formula (33) can be carried out, for example, according to the process in the eighteenth step.

In the thirty-seventh step, the conversion of the compound of formula (33) to the compound of formula (19) can be carried out, for example, according to the process in the first step.

Fifthly, among a group of compounds of formulae (22) and (26), compounds wherein $R_1$ represents a five- to seven-membered saturated cyclic amine where $R_9$ represents a hydrogen atom or $C_{1-6}$ alkyl (formulae (35) and (36)) cannot be efficiently produced without difficulties by the process shown in scheme 4, for example, for production or purification reasons. The group of compounds (formulae (35) and (36)) can also be produced by an alternative process, for example, by the following process from the compound of formula (22) or formula (26), wherein $R_1$ represents pyridyl or a five- to seven-membered unsaturated cyclic amine containing N—$R_9$ in its ring, produced by the process shown in scheme 4.

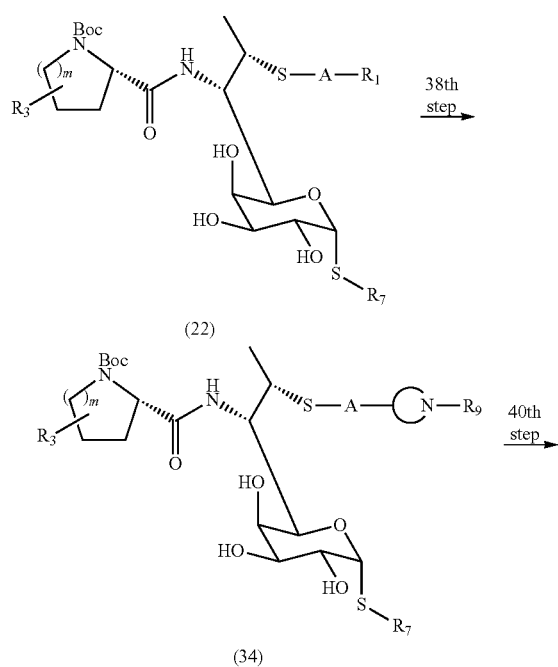

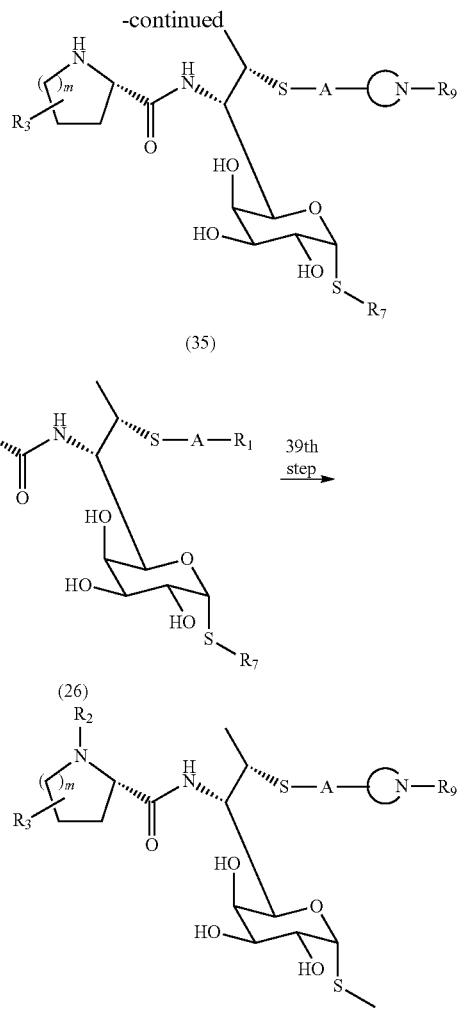

In the thirty-eighth step, thirty-ninth step, the conversion of the compound of formula (22) to the compound of formula (34) and the conversion of the compound of formula (26) to the compound of formula (36) can be carried out, for example, according to the process described in the tenth step.

In the fortieth step, the compound of formula (34) can be converted to the compound of formula (35), for example, according to the process described in the twenty-ninth step.

Sixthly, among a group of compounds produced in scheme 6 wherein $R_1$ represents —B—$NR_{10}R_{11}$ wherein B represents optionally substituted aryl or a heterocyclic ring and $R_{10}$ represents a hydrogen atom or $C_{1-6}$ alkyl, or B and $R_{10}$ together form a four- to seven-membered heterocyclic ring, and $R_{11}$ represents $C_{1-6}$ alkyl or acyl, a group of compounds of formula (39) or (41) cannot be efficiently produced without difficulties by the process shown in scheme 4, for example, for production or purification reasons. The group of compounds of formula (39) or (41) can also be produced by an alternative process, for example, by producing the compound of formula (37) or (40) as a precursor of the compound of formula (39) or (41) by the process shown in scheme 4 or scheme 5 and then subjecting the precursor to the following process.

Scheme 6

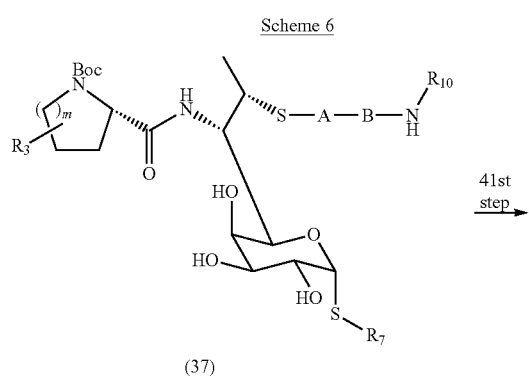

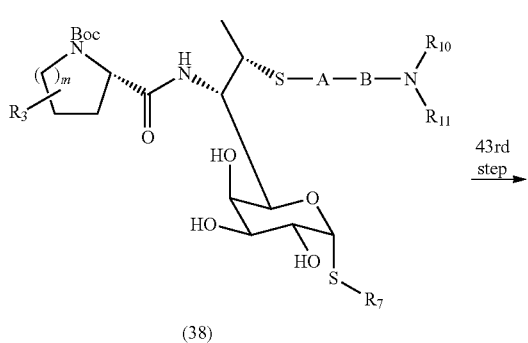

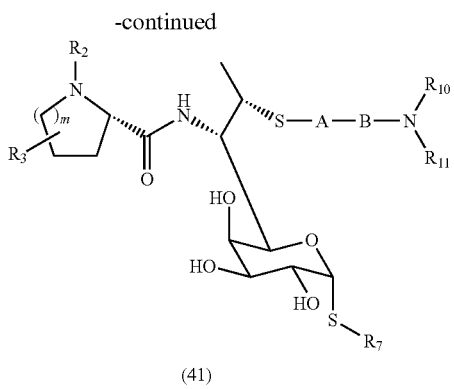

In the forty-first step and forty-second step, the conversion of the compound of formula (37) to the compound of formula (38) and the conversion of the compound of formula (40) to the compound of formula (41) can be carried out, for example, according to the process described in the eleventh step.

In forty-third step, the compound of formula (38) can be converted to the compound of formula (39), for example, according to the process described in the twenty-ninth step.

Seventhly, a group of compounds of formula (I) wherein $R_4$ and $R_5$ represent acyl and $R_6$ represents a hydrogen atom or acyl can be produced from the compound of formula (22) or (26) by the following process.

Scheme 7

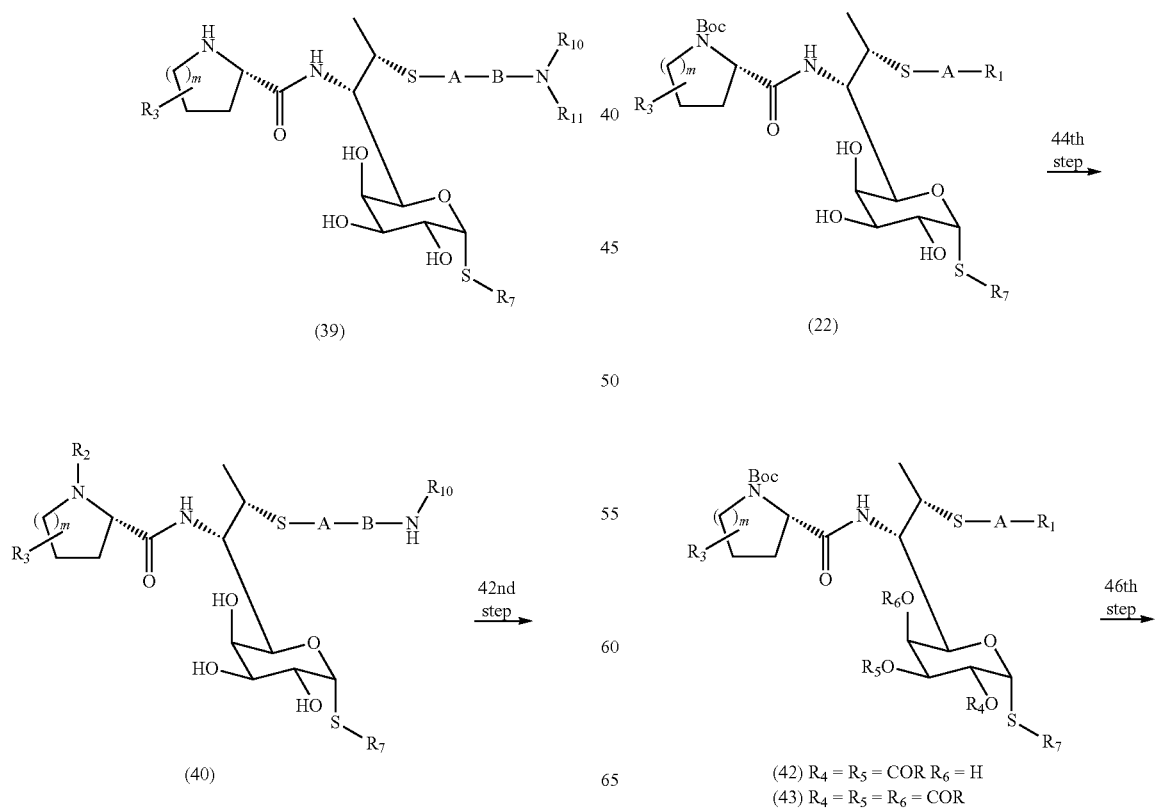

(42) $R_4 = R_5 = COR$ $R_6 = H$
(43) $R_4 = R_5 = R_6 = COR$

-continued

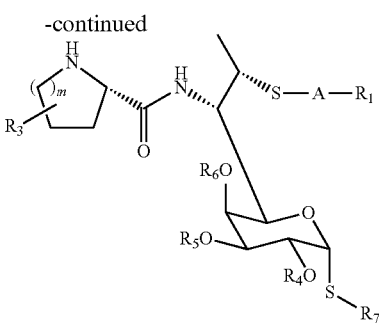

(44) $R_4 = R_5 = COR$ $R_6 = H$
(45) $R_4 = R_5 = R_6 = COR$

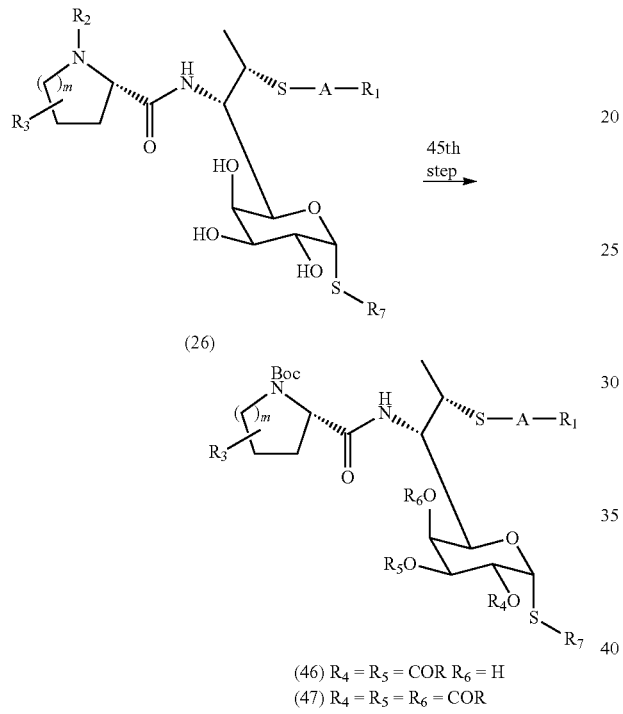

(46) $R_4 = R_5 = COR$ $R_6 = H$
(47) $R_4 = R_5 = R_6 = COR$

In the forty-fourth step and forty-fifth step, the conversion of the compound of formula (22) to the compound of formula (42) and the conversion of the compound of formula (26) to the compound of formula (46) can be carried out, for example, by reacting the compound of formula (22) or formula (26) with 3 to 10 equivalents of an optionally substituted acid anhydride or an acyl halide in a pyridine solvent in the presence of a base. The reaction temperature is −10 to 50° C., and the reaction time is 1 to 3 hr. The reaction solvent in this reaction may be a conventional solvent in addition to pyridine, and preferred examples thereof include solvents such as tetrahydrofuran, dimethylsulfoxide, 1-methylpyrrolidone, dimethylformamide. The base may be a conventional organic base or inorganic base, and preferred examples thereof include dimethylaminopyridine and triethylamine. The base is preferably used in an excessive amount.

The conversion of the compound of formula (22) to the compound of formula (43) and the conversion of the compound of formula (26) to the compound of formula (47) can be carried out, for example, by reacting the compound of formula (22) or the compound of formula (26) with 5 to 10 equivalents of an acid anhydride or an acyl halide in the solvent and in the presence of the base as described in the production of compounds of formulae (42) and (46) in the presence of a base. The reaction temperature is 0 to 100° C., and the reaction time is 0.5 to 24 hr.

In the forty-sixth step, the conversion of the compound of formula (42) to the compound of formula (44) and the conversion of the compound of formula (43) to the compound of formula (45) can be carried out, for example, according to the process described in the twenty-ninth step.

Eighthly, a group of compounds of formula (I) wherein $R_4$ represents acyl and $R_5$ and $R_6$ represent a hydrogen atom can be produced from the compound of formula (22) or (26) by the following process.

Scheme 8

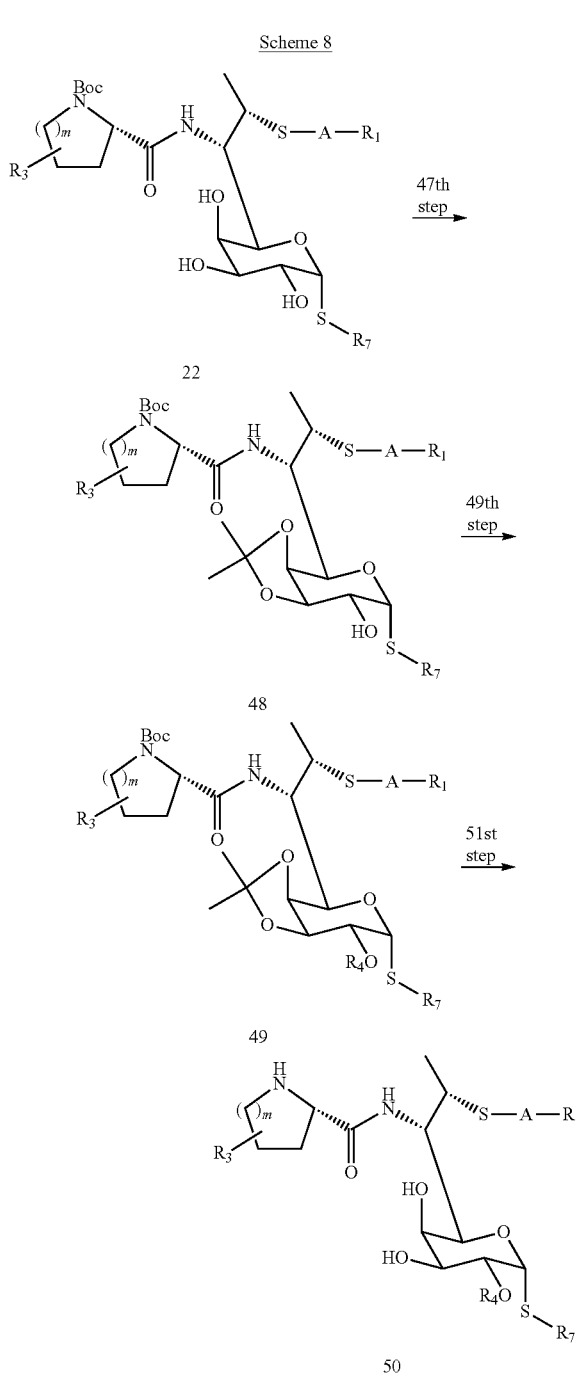

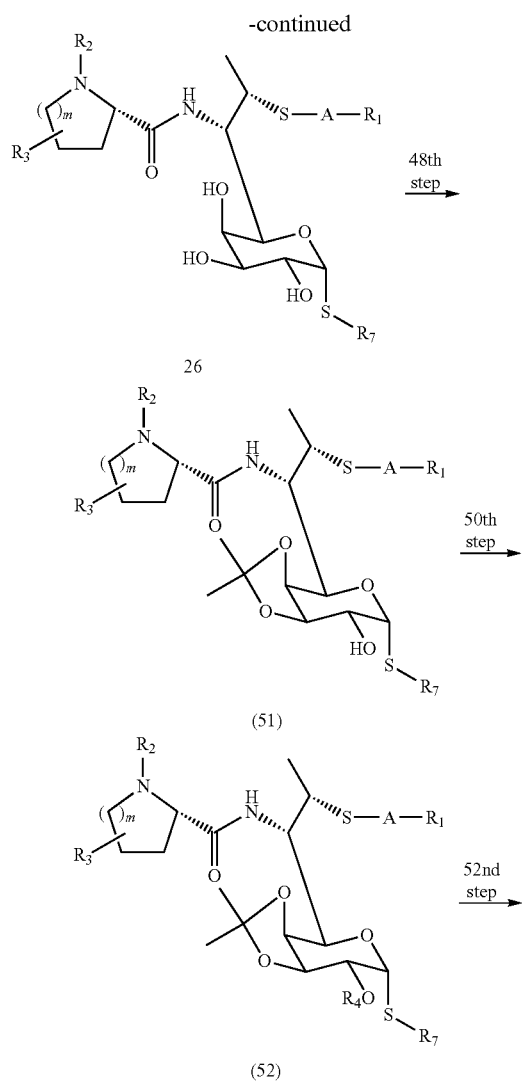

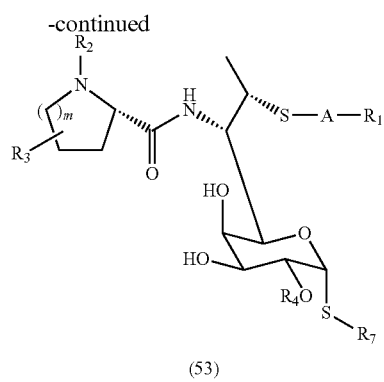

In the forty-seventh step and forty-eighth step, the conversion of the compound of formula (22) to the compound of formula (48) and the conversion of the compound of formula (26) to the compound of formula (51) can be carried out, for example, by the process described in J. Med. Chem., 13 (1970), 616.

In the forty-ninth step and fifty step, the conversion of the compound of formula (48) to the compound of formula (49) and the conversion of the compound of formula (51) to the compound of formula (52) can be carried out, for example, according to the process described in the forty-fourth step and the forty-fifth step.

In the fifty-first step and fifty-second step, the conversion of the compound of formula (49) to the compound of formula (50) and the conversion of the compound of formula (52) to the compound of formula (53) can be carried out, for example, according to the process described in the twenty-ninth step.

Ninthly, a group of compounds of formula (I), wherein $R_4$, $R_5$, and $R_6$ represent hydrogen atom and m is 3, can be produced, for example, by the following general process.

Scheme 9

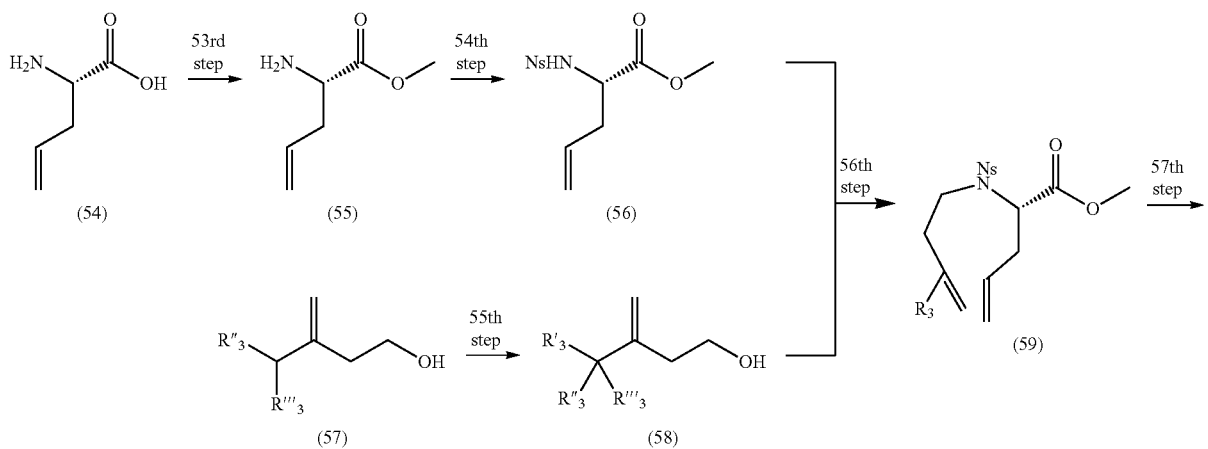

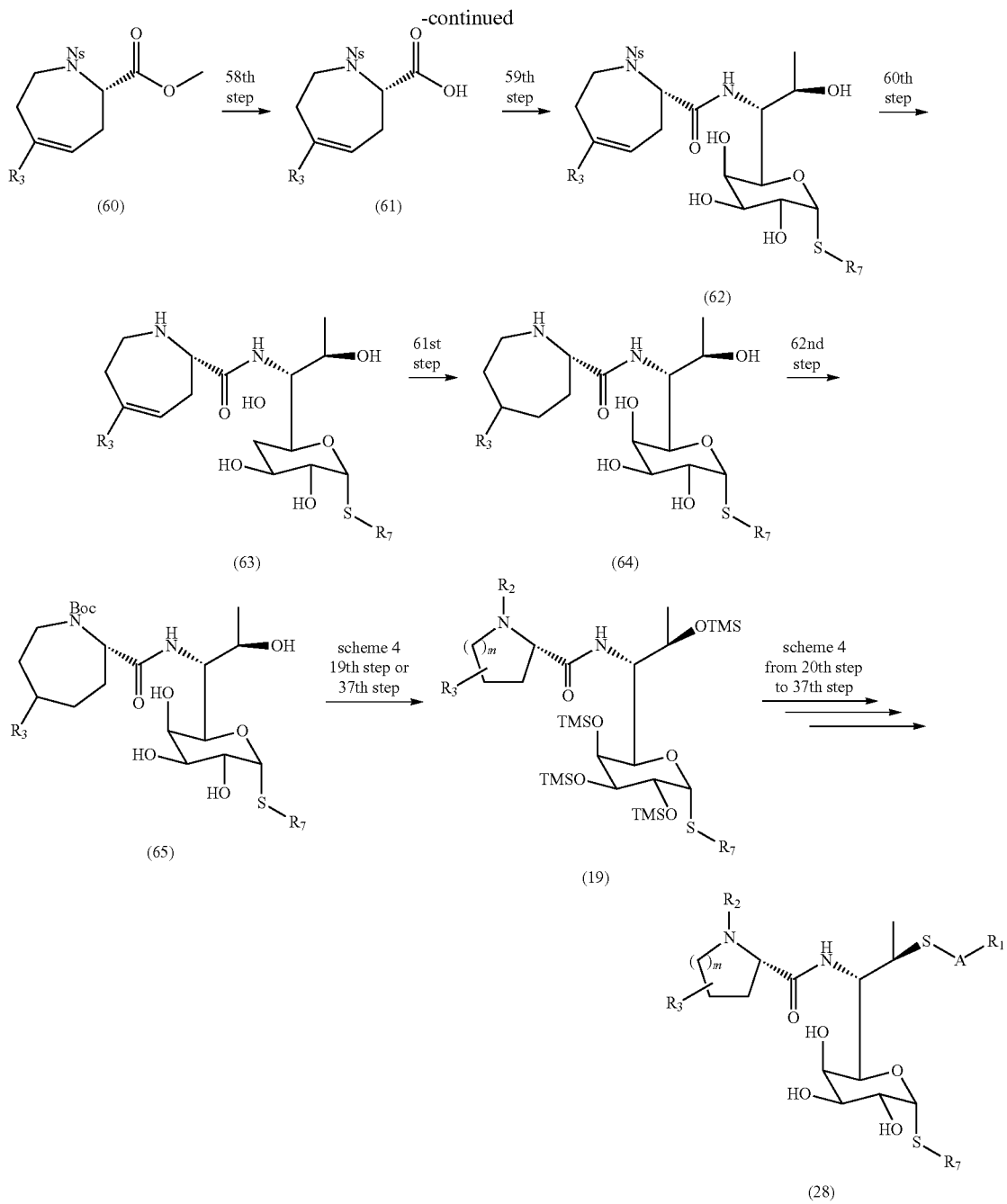

In scheme 9, $R_3$ represents $R'_3(CR''_3)(R'''3)$ wherein Ns represents o-nitrobenzenesulfonyl.

In the fifty-third step, the compound of formula (54) can be converted to the compound of formula (55) by either process (i) or process (ii). In process (i), the compound of formula (55) can be produced, for example, by reacting the compound of formula (54) in a methanol solvent in the presence of 1 to 10 equivalents of 4 N hydrochloric acid-dioxane. The acid in this reaction may be a commonly known strong acid in addition to hydrochloric acid. For example, sulfuric acid is preferred. The amount of the acid is preferably 1 to 10 equivalents. The reaction temperature is 0 to 50° C., and the reaction time is 0.5 to 120 hr. In process (ii), the compound of formula (55) can be produced by reacting the compound of formula (54) in a methanol solvent in the presence of 1 to 10 equivalents of thionyl chloride. The reaction reagent in this reaction may be a commonly known carboxylic acid activating agent in addition to thionyl chloride, and preferred examples thereof include thionyl bromide, oxalyl chloride, and dicyclohexylcarbodiimide-4-dimethylaminopyridine combined condensing agents. The amount of the reaction reagent is preferably 1 to 10 equivalents. The reaction temperature is 0 to 50° C., and the reaction time is 0.5 to 24 hr.

In the fifty-fourth step, the compound of formula (55) can be converted to the compound of formula (56), for example, by reacting the compound of formula (55) with 1 to 10 equivalents of o-nitrobenzenesulfonyl chloride in a diethyl ether solvent in the presence of a base. The reaction solvent in this reaction may be a conventional solvent in addition to diethyl ether. Preferred examples thereof include tetrahydrofuran, dimethylsulfoxide, 1-methylpyrrolidone, N,N-dimethylformamide, and methylene chloride. The base may be a conventional known inorganic base or organic base, and preferred examples thereof include sodium hydrogencarbonate, potassium carbonate, potassium phosphate, lithium hydroxide, sodium hydroxide, triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

In the fifty-fifth step, the compound of formula (57) can be converted to the compound of formula (58), for example, by reacting the compound of formula (57) with 3-methyl-3-buten-1-ol at 0° C. in a diethyl ether solvent in the presence of N,N,N',N'-tetramethylethylenediamine and n-butyllithium, then adding 1 to 5 equivalents of an alkyl bromide represented by $R'_3Br$ at −78° C., and raising the temperature of the reaction system to room temperature. The reaction solvent in this reaction may be a conventional ether solvent in addition to diethyl ether, and preferred examples thereof include tetrahydrofuran. The reaction temperature is −78° C. to room temperature, and the reaction time is 15 to 36 hr.

In the fifty-sixth step, the compound of formula (56) and the compound of formula (58) can be converted to the compound of formula (59), for example, by reacting 1 to 10 equivalents of the compound of formula (56) in a tetrahydrofuran solution in the presence of the compound of formula (58), triphenylphosphine, and diisopropyl azodicarboxylate. The reaction solvent in this reaction may be a conventional reaction solvent in addition to tetrahydrofuran, and preferred examples thereof include benzene, toluene, trifluoromethylbenzene, and acetonitrile. The phosphine reagent may be a phosphine reagent commonly known in literatures in addition to triphenylphosphine, and preferred examples thereof include o-tolylphosphine and tri-n-butylphosphine. The amount of the phosphine reagent is preferably 1 to 5 equivalents. The azo reagent may be a azo reagent commonly known in literatures in addition to diisopropyl azodicarboxylate, and preferred examples thereof include diethyl azodicarboxylate and 1,1'-(azodicarbonyl)dipiperidine. The amount of the azo reagent is preferably 1 to 5 equivalents. The reaction temperature is 0 to 50° C., and the reaction time is 0.5 to 24 hr.

In the fifty-seventh step, the compound of formula (59) can be converted to the compound of formula (60), for example, by ring-closing the compound of formula (59) in a methylene chloride solvent in the presence of 0.01 to 0.1 equivalent of benzylidene[1,3-bis(2,4,6-trimethylphenyl)-2-imidazolidinylidene]dichloro(tricyclohexylphosphine)-ruthenium. The reaction solvent in this reaction may be a conventional halogenic solvent in addition to the methylene chloride solvent, and preferred examples thereof include chloroform, carbon tetrachloride, and 1,2-dichloroethane. The reaction temperature is room temperature to 100° C., and the reaction time is 0.5 to 24 hr In the fifty-eighth step, the compound of formula (60) can be converted to the compound of formula (61), for example, by hydrolyzing the compound of formula (60) in a dioxane-water mixed solvent in the presence of a base.

The reaction solvent in this reaction may be a conventional alcohol-water mixed solvent in addition to the dioxane-water mixed solvent, and a mixed solvent composed of methanol, ethanol, propanol, or butanol with water is preferred. The base may be a commonly known inorganic base, and preferred examples thereof include lithium hydroxide, sodium hydroxide, potassium hydroxide, and barium hydroxide. The amount of the base is preferably 1 to 10 equivalents. The reaction temperature is 0 to 120° C., and the reaction time is 0.5 to 24 hr.

In the fifty-ninth step, the compound of formula (61) can be converted to the compound of formula (62), for example, according to the process described in the eighteen step in scheme 4 above.

In the sixty step, the compound of formula (62) can be converted to the compound of formula (63), for example, by reacting the compound of formula (62) with 1 to 10 equivalents of benzenethiol in an N,N-dimethylformamide solvent in the presence of a base. The reaction solvent in this reaction may be a conventional solvent in addition to N,N-dimethylformamide, and preferred examples thereof include tetrahydrofuran, dimethylsulfoxide, 1-methylpyrrolidone, and diethyl ether. The base may be a commonly known inorganic base or organic base, and preferred examples thereof include potassium carbonate, sodium hydroxide, triethylamine, diisopropylethylamine, 1,8-diazabicyclo[5.4.0]-7-undecene, and 7-methyl-1,5,7-triazabicyclo-[4,4,0]dec-5-ene. The amount of the base is preferably 1 to 10 equivalents. The thiol may be a commonly known alkylthiol or arylthiol in addition to benzenethiol, and preferred examples thereof include 4-bromobenzenethiol and 4-t-butylbenzenethiol. The amount of the thiol is preferably 1 to 10 equivalents. The reaction temperature is 0 to 50° C., and the reaction time is 0.5 to 24 hr.

In the sixty-first step, the conversion of the compound of formula (63) to the compound of formula (64) can be carried out, for example, by allowing a reaction to proceed in a methanol solvent in the presence of a metallic catalyst under a hydrogen atmosphere. The metallic catalyst in this reaction may be a metallic catalyst commonly used in hydrogen reduction, and preferred examples thereof include Raney nickel, palladium/carbon, and palladium hydroxide/carbon. The reaction temperature is 0 to 50° C., and the reaction time is 0.5 to 24 hr.

In the sixty-second step, the compound of formula (64) can be converted to the compound of formula (65), for example, according to the process described in the thirty-fifth step in scheme 4 above.

The compound of formula (65) can be converted to the compound of formula (19), for example, according to the process described in the nineteenth step or thirty-seventh step in scheme 4 above.

In scheme 9, the compound of formula (19) wherein m=3 can be converted to the compound of formula (26), for example, according to the process described in scheme 4 above.

EXAMPLES

The present invention is further illustrated by the following Examples that are not intended as a limitation of the invention. Reference Examples and Examples for producing the compounds of the present invention and the physicochemical properties of the compounds of the present invention will be described.

Reference Example 1

5-(4-Bromophenyl)pyrimidine

5-Bromopyrimidine (954 mg, 6 mmol) and 1.0 g (5.0 mmol) of 4-bromophenylboronic acid were dissolved in 20 ml of N,N-dimethylformamide and 5 ml of water. Tetrakistriphenylphosphine palladium (590 mg, 0.5 mmol) and 830 mg (7.5 mmol) of sodium carbonate were added to the solution, and the mixture was stirred at 80° C. for 2.5 hr. Ethyl acetate (60 ml) and 8.5 ml of water were added to the reaction solution. The mixture was filtered through Celite. The filtrate as an organic layer was washed five times with 30 ml of water. The organic layer was dried over anhydrous sodium sulfate and was filtered. The solvent was then removed by distillation, and the residue was purified by column chromatography on silica gel (n-hexane:ethyl acetate=5:1) to give 960 mg (yield 82%) of the title compound.

$^1$H-NMR (300 MHz, CDCl$_3$) δ: 7.52 (2H, d, J=7.5 Hz), 7.56 (2H, d, J=7.5 Hz), 9.00 (2H, s), 9.22 (1H, ddd, J=s).

MS (FAB) m/z: 234 (M$^+$+1).

The following compounds were synthesized in the same manner as in Reference Example 1. The compounds thus obtained were used in the Examples.

5-(4-Bromo-2,6-difluorophenyl)pyrimidine, 5-(4-bromo-2-fluorophenyl)pyrimidine, 5-(4-bromo-3-fluorophenyl)pyrimidine, 2-bromo-5-(pyrimidin-5-yl)benzonitrile, 5-bromo-2-(pyrimidin-5-yl)benzonitrile, 5-(4-bromo-2,5-dimethoxyphenyl)pyrimidine, 2-(4-bromophenyl)pyrimidine, 2-(4-bromophenyl)pyrazine, 5-(4-bromophenyl)-2-methoxypyrimidine, 5-(4-bromophenyl)thiazole, 5-(4-bromophenyl)-N,N-dimethylthiazole-4-carbixamide, 5-(5-bromothiophen-2-yl)pyrimidine, 5-(4-bromophenyl)pyrazin-2-amine, 5-(6-bromopyridin-3-yl)pyrimidine, 5-(5-bromopyridin-2-yl)pyrimidine, 2-bromo-2,5'-bipyrimidine, 5-bromo-2,5'-bipyrimidine, 3-(4-bromophenyl)pyridine, 5-(4-bromophenyl)nicotinonitrile, 3-(4-bromophenyl)-5-fluoropyridine, 3-(4-bromophenyl)-5-methoxypyridine, 3-(4-bromophenyl)-4-nitropyridine-1-oxide, 5-(4-bromophenyl)-2-fluoropyridine, 5-bromo-2,3'-bipyridine, and 6-bromo-3,3'-bipyridine.

Reference Example 2

5-(4-Bromophenyl)-1-methyl)-1,2,3,6-tetrahydropyridine

Iodomethane (0.5 ml, 8.0 mmol) was added to a solution of 199 mg (0.85 mmol) of 3-(4-bromophenyl)pyridine in acetonitrile (11 ml), and the mixture was heated under reflux with stirring for 14 hr. The solvent was removed by distillation. The residue was dissolved in 2.7 ml of methanol and 2.7 ml of water. Sodium borohydride (292 mg) was added to the solution under ice cooling, and the mixture was stirred under ice cooling for one hr and at room temperature for 20 hr. The reaction solution was adjusted to pH 1 by the addition of 5 N hydrochloric acid and was then concentrated. The residue was adjusted to pH 9 by the addition of aqueous ammonia. The aqueous solution was extracted thrice with 10 ml of ethyl acetate. The organic layers were combined and were dried over anhydrous sodium sulfate followed by fitration. The filtrate was concentrated under the reduced pressure, and the residue was purified by column chromatography on silica gel (n-hexane:ethyl acetate=1:1 to chloroform:methanol=20:1) to give 126 mg (yield 59%) of the title compound.

$^1$H-NMR (300 MHz, CDCl$_3$) δ: 2.31-2.39 (2H, m), 2.44 (3H, s), 2.55 (2H, t, J=6.0 Hz), 3.22-3.24 (2H, m), 6.08-6.12 (1H, m), 7.19 (2H, d, J=8.4 Hz), 7.41 (2H, d, J=8.4 Hz).

MS (API) m/z: 252 (M$^+$+1).

The following compounds were synthesized in the same manner as in Reference Example 2. The compounds thus obtained were used in the Examples.

5-(4-Bromophenyl)-1-ethyl)-1,2,3,6-tetrahydropyridine, 5-(4-bromophenyl)-1-(2-methoxyethyl)-1,2,3,6-tetrahydropyridine, 5-(4-bromophenyl)-1-(2-hydroxyethyl)-1,2,3,6-tetrahydropyridine, 2-(3-(4-bromophenyl)-5,6-dihydropyridin-1(2H)-yl)-N,N-dimethylethanamine, and 5-bromo-2-(1-methyl-1,2,3,6-tetrahydropyridin-3-yl)pyridine.

Step (i) of Reference Example 3

(4-Bromophenyl)(pyridin-3-yl)methanol

3-Bromopyridine (0.4 ml, 4.0 mmol) was dissolved in 15 ml of tetrahydrofuran in an argon atmosphere. n-Butyllithium (1.58 M n-hexane solution, 2.4 ml, 3.8 mmol) was added to the solution at −78° C., and the mixture was stirred for 25 min. Subsequently, a solution of 502 mg (2.7 mmol) of 4-bromobenzaldehyde in tetrahydrofuran (2 ml) was added dropwise thereto at −78° C., and the mixture was stirred at −78° C. for one hr, was stirred under ice cooling for one hr, and was then stirred at room temperature for one hr. The reaction solution was diluted with 30 ml of ethyl acetate, and the diluted solution was washed with a saturated aqueous ammonium chloride solution. The aqueous layer was extracted twice with 5 ml of ethyl acetate. The organic layers were combined and were washed with 25% brine. The organic layer was dried over anhydrous sodium sulfate and was then filtered. The filtrate was concentrated under the reduced pressure, and the residue was purified by column chromatography on silica gel (n-hexane:ethyl acetate=1:1) to give 282 mg (yield 40%) of the title compound.

$^1$H-NMR (300 MHz, CDCl$_3$) δ: 5.80 (1H, s), 7.23 (2H, d, J=8.4 Hz), 7.47 (2H, d, J=8.4 Hz), 7.66 (1H, ddd, J=1.5, 1.8, 7.8 Hz), 8.40 (1H, dd, J=1.8, 4.8 Hz), 8.48 (1H, s).

MS (API) m/z: 264 (M$^+$+1).

Step (ii) of Reference Example 3

3-((4-Bromophenyl)(methoxymethyl)methyl)pyridine

Sodium hydride (24.8 mg, 0.62 mmol) and 35 μl (0.56 mmol) of iodomethane were added to a solution of 97.9 mg (0.37 mmol) of the title compound produced in step (i) of Reference Example 3 in N,N-dimethylformamide (2 ml), and the mixture was stirred at room temperature for 2 hr. The reaction solution was diluted with 10 ml of ethyl acetate, and the diluted solution was washed with a saturated aqueous ammonium chloride solution. The aqueous layer was extracted twice with 3 ml of ethyl acetate. The organic layers were combined and were washed with 25% brine, were dried over anhydrous sodium sulfate, and were then filtered. The filtrate was concentrated under the reduced pressure, and the residue was purified by column chromatography on silica gel (n-hexane:ethyl acetate=3:1) to give 56.2 mg (yield 55%) of the title compound.

$^1$H-NMR (300 MHz, CDCl$_3$) δ: 3.38 (3H, s), 5.23 (1H, s), 7.22 (2H, d, J=8.7 Hz), 7.25-7.28 (1H, m), 7.48 (2H, d, J=8.4 Hz), 7.61 (1H, dt, J=1.8, 7.8 Hz), 8.52 (1H, dd, J=1.8, 4.8 Hz), 8.58 (1H, d, J=2.1 Hz).

MS (API) m/z: 278 (M$^+$+1).

The following compounds were synthesized in the same manner as in Reference Example 2, and the compounds thus obtained were used in the Examples.

2-((4-Bromophenyl)(methoxymethyl)methyl)pyridine and 5-((4-bromophenyl)(methoxymethyl)methyl)pyridine.

Step (i) of Reference Example 4

Ethyl 2-(4-bromophenyl)thiazole-4-carboxylate

Ethyl 2-bromopyruvate (0.18 ml) was added to a solution of 529 mg (1.0 mmol) of 4-bromobenzothioamide in ethanol (3 ml), and the mixture was stirred at room temperature for 6 hr. The precipitated crystal was collected by filtration, was dried, and was then added dropwise to 5 ml of concentrated sulfuric acid. The mixture was stirred at room temperature for 3 hr. The solvent was removed by distillation, and the residue was diluted with ethyl acetate. The diluted solution was washed with a saturated aqueous sodium bicarbonate solution and water, and the organic layer was dried over anhydrous magnesium sulfate. After filtration, the filtrate was concentrated, and the resultant crystal was collected by filtration and was dried to give 285 mg (yield 91%) of the title compound.

$^1$H-NMR (300 MHz, CDCl$_3$) δ: 1.30 (3H, t, J=7.5 Hz), 4.30 (1H, q, J=7.5 Hz), 7.65 (2H, d, J=7.8 Hz), 7.85 (2H, d, J=7.8 Hz), 8.15 (1H, s)

MS (FAB) m/z: 313 (M$^+$+1).

Step (ii) of Reference Example 4

2-(4-Bromophenyl)thiazole-4-carboxamide

The title compound (100 mg, 0.32 mmol) produced in step (i) of Reference Example 4 was dissolved in a 7 N ammonia-methanol solution. The solution was stirred in a sealed tube at 100° C. for 16 hr. The solvent was removed by distillation, and the resultant crystal was collected by filtration and was dried to give 85 mg (yield 93%) of the title compound.

$^1$H-NMR (300 MHz, CDCl$_3$) δ: 7.68 (2H, d, J=7.8 Hz), 7.88 (2H, d, J=7.8 Hz), 8.21 (1H, s)

MS (FAB) m/z: 284 (M$^+$+1).

The following compounds were synthesized in the same manner as in Reference Example 4, and the compounds thus obtained were used in the Examples.

2-(4-Bromophenyl)-N,N-dimethylthiazole-4-carboxamide, 2-(4-bromophenyl)-N,N-dimethylthiazole-5-carboxamide, 2-(4-bromophenyl)thiazole-5-carboxamide, and (4-bromophenyl)(morpholino)methanone.

Reference Example 5

Tert-Butyl 1-(5-bromopyridin-2-yl)pyrrolidin-3-ylcarbamate

5-Bromo-2-fluoropyridine (1.76 mg, 10 mmol) and 3.62 g (10 mmol) of tert-butyl pyrrolidin-3-ylcarbamate were dissolved in 20 ml of N,N-dimethylformamide. Potassium carbonate (1.38 g, 10 mmol) was added to the solution, and the mixture was stirred at 100° C. for 6 hr. Ethyl acetate (60 ml) and 8.5 ml of water were added to the reaction solution, and the organic layer was washed five times with 30 ml of water. The organic layer was dried over anhydrous sodium sulfate and was filtered. The solvent was then removed by distillation, and the residue was purified by column chromatography on silica gel (n-hexane:ethyl acetate=4:1) to give 1.23 g (yield 36%) of the title compound.

$^1$H-NMR (300 MHz, CDCl$_3$) δ: 1.39 (9H, s), 1.5-2.0 (2H, m), 2.6-3.2 (4H, m), 7.05 (1H, d, J=7.8 Hz), 7.88 (1H, d, J=7.8 Hz), 8.21 (1H, s)

MS (FAB) m/z: 343 (M$^+$+1).

Step (i) of Reference Example 6

4-(1-Hydroxy-2-(2-nitrophenylsulfonamide)ethyl) phenyl 2-nitrobenzenesulfonate

A 1 N aqueous sodium hydroxide solution (79.1 ml, 79.1 mmol) was added to a solution of 5 g (26.4 mmol) of 4-(2-amino-1-hydroxyethyl)phenol in dioxane (50 ml), and the mixture was stirred at room temperature for 5 min. 2-Nitrobenzenesulfonyl chloride (14.6 g, 65.9 mmol) was added to the solution, and the mixture was stirred at room temperature for 17 hr. The dioxane solvent was then removed under the reduced pressure, and the residue was extracted with methylene chloride. The extract was dried over anhydrous sodium sulfate and was then filtered. The filtrate was concentrated under the reduced pressure, and the residue was purified by column chromatography on silica gel (n-hexane:ethyl acetate=2:1) to give 13.3 g (yield 97%) of the title compound.

Step (ii) of Reference Example 6

4-(1-Hydroxy-2-(N-(2-hydroxyethyl)-2-nitrophenylsulfonamide) ethyl)phenyl 2-nitrobenzenesulfonate Sodium hydride (0.31 g, 7.0 mmol) was added to a solution of 3.0 g (5.82 mmol) of the title compound produced in step (i) of Reference Example 6 in N,N-dimethylformamide (19.1 ml), and the mixture was stirred at room temperature for 30 min. Thereafter, 1.65 g (5.82 mmol) of tert-butyl(2-iodoethoxy)dimethylsilane was added thereto, and the mixture was stirred at 100° C. for 21 hr. Sodium hydrogencarbonate was added to the reaction solution to stop the reaction, followed by extraction with ethyl acetate. The organic layer was washed with water and saturated brine in that order, was dried over anhydrous sodium sulfate, and was then filtered. The filtrate was concentrated under the reduced pressure.

Methanol (48 ml) was added to the residue. 1 N hydrochloric acid (11.6 ml, 11.6 mmol) was then added thereto, and the mixture was stirred at room temperature for 30 min. Sodium hydrogencarbonate was added thereto to stop the reaction. The methanol solvent was then removed under the reduced pressure, and the residue was then extracted with ethyl acetate. The organic layer was washed with water and saturated brine in that order, was dried over anhydrous sodium sulfate, and was then filtered. The filtrate was concentrated under the reduced pressure, and the residue was purified by column chromatography on silica gel (chloroform:methanol=100:1) to give 2.22 g (yield 68%) of the title compound.

Step (iii) of Reference Example 6

4-(4-(2-Nitrobenzenesulfonyl)morpholin-2-yl)phenyl 2-nitrobenzenesulfonate

A 1 M solution (5.87 ml) of (cyanomethylene)tributylphosphorane (5.87 mmol) in toluene was added to a solution of 2.22 g (3.91 mmol) of the title compound produced in step (ii) of Reference Example 6 in toluene (55.0 ml), and the mixture was heated under reflux with stirring for 1 hr 20 min. Thereafter, the reaction solution was cooled to room temperature, and the solvent was removed under the reduced pressure. The residue was purified by column chromatography on silica gel (n-hexane:ethyl acetate=2:1) to give 1.16 g (yield 54%) of the title compound.

Step (iv) of Reference Example 6

4-(Morpholin-2-yl)phenol

Potassium carbonate (0.88 g, 6.33 mmol) was added to a solution of 1.16 g (2.11 mmol) of the title compound produced in step (iii) of Reference Example 6 in N,N-dimethylformamide (8.5 ml), and the mixture was stirred at room temperature for 5 min. 4-Bromobenzenethiol (1.20 g, 6.33 mmol) was added to the reaction solution, and the mixture was stirred at room temperature for 3.5 hr. 1 N hydrochloric acid was added thereto to stop the reaction and to adjust the pH value of the solution to 3. The aqueous layer was washed with ethyl acetate, and the aqueous layer was concentrated to dryness under the reduced pressure. Methanol was added to the residue, and the mixture was filtered. The filtrate was concentrated under the reduced pressure, and the residue was purified by column chromatography on silica gel (chloroform:methanol=20:1, chloroform:methanol:28% aqueous ammonia=9:2:0.2) to give 240 mg (yield 63%) of the title compound.

Step (v) of Reference Example 6

4-(4-Methylmorpholin-2-yl)phenol

A 36% aqueous formaldehyde solution (20.1 mg, 2.51 mmol), 0.029 ml (0.502 mmol) of acetic acid, and 53.2 mg (0.251 mmol) of sodium triacetoxy borohydride were added in that order to a solution of 15 mg (0.084 mmol) of the title compound produced in step (iv) of Reference Example 6 in methanol (0.7 ml), and the mixture was stirred at room temperature for 15 min. Thereafter, the reaction solution was purified by preparative thin-layer chromatography (chloroform:methanol:28% aqueous ammonia=9:2:0.2) to give 15 mg (yield 93%) of the title compound.

$^1$H-NMR (400 MHz, CD$_3$OD:CDCl$_3$=1:1) δ: 2.15 (1H, dd, J=10.7, 11.7 Hz), 2.30 (1H, dt, J=3.4, 11.7 Hz), 2.79 (1H, d, J=11.7 Hz), 2.86 (1H, d, J=11.9 Hz), 3.82 (1H, dt, J=2.2, 11.7 Hz), 7.02 (1H, dd, J=2.2, 11.7 Hz), 4.46 (1H, dd, J=3.2, 10.4 Hz), 6.80 (2H, ddd, J=2.0, 2.7, 8.5 Hz), 7.20 (2H, ddd, J=2.0, 2.7, 8.8 Hz).

MS (ESI$^+$) m/z: 194 (M$^+$+1).

Reference Example 7

5-(5-Methyl-2-nitrophenyl)-1,3,4-thiadiazole-2-thiol

Carbon bisulfide (4 ml) was added to a solution of 1.95 g (10 mmol) of 5-methyl-2-nitrobenzohydrazide in methanol (8 ml). A solution of 616 mg (11 mmol) of potassium hydroxide in methanol (10 ml) was then added thereto, and the mixture was stirred at room temperature for 6 hr. The precipitated crystal was collected by filtration and was dried. The dried crystal was then added dropwise to concentrated sulfuric acid (5 ml), and the mixture was stirred at room temperature for 3 hr. The reaction solution was added dropwise to 100 ml of iced water. The resultant precipitate was collected by filtration and was dried to give 1.28 g (yield 51%) of the title compound.

$^1$H-NMR (300 MHz, CDCl$_3$) δ: 2.35 (3H, s), 7.28 (1H, d, J=7.8 Hz), 7.54 (1H, s), 8.13 (1H, d, J=7.8 Hz)

MS (FAB) m/z: 254 (M$^+$+1).

The following compound was synthesized in the same manner as in Reference Example 7. The compound thus obtained was used in the Examples.

5-(5-(Methylamino)thiazol-4-yl)-1,3,4-thiadiazole-2-thiol

Step (i) of Reference Example 8

5-(4,5-Dimethoxy)-2-nitrobenzohydrazide

Hydrazine monohydrate (3.2 ml, 10 mmol) was added to a solution of 5.00 g (21 mmol) of methyl 4,5-methoxy-2-nitrobenzoate in ethanol (20 ml), and the mixture was heated under reflux with stirring overnight. Further, 16.2 ml (52 mmol) of hydrazine monohydrate was added thereto, and the mixture was stirred overnight. The reaction solution was cooled to room temperature, and the precipitated crystal was filtered to give 1.24 g (yield 25%) of the title compound.

$^1$H-NMR (400 MHz, DMSO$_{d-6}$) δ: 3.32 (1H, s), 4.43 (2H, br), 7.04 (1H, s), 7.59 (1H, s), 9.60 (1H, s).

MS (FAB) m/z 242 (M+1)$^+$.

Step (ii) of Reference Example 8

5-(4,5-Dimethoxy-2-nitrophenyl)-1,3,4-oxadiazole-2-thiol

A 20% sodium ethoxide-ethanol solution (847 μl) was added to a solution of 600 mg (2.49 mmol) of the title compound in step (i) of Reference Example 8 in ethanol (10 ml), and the mixture was heated under reflux with stirring for 17 hr 30 min. The reaction solution was cooled to room temperature and was then concentrated. The residue was dissolved in water. The solution was adjusted to pH 2 by the addition of 1 N hydrochloric acid. The precipitated crystal was collected by filtration, was washed with water, and was then dried to give 500 mg (yield 71%) of the title compound.

$^1$H-NMR (400 MHz, DMSO$_{d-6}$) δ: 3.93 (3H, s), 3.95 (3H, s), 7.47 (1H, s), 7.80 (1H, s).

MS (FAB) m/z 284 (M+1)$^+$.

The following compound was synthesized in the same manner as in Reference Example 8. The compound thus obtained was used in the Examples.

5-(5-(Methylamino)thiazol-4-yl)-1,3,4-oxadiazole-2-thiol

Reference Example 9

5-(4,5-Dimethoxy-2-nitrophenyl)oxazole-2-thiol 4,5-Dimethoxy-2-nitrobenzaldehyde (1.52 g, 7.19 mmol), 353.0 mg (6.07 mmol) of potassium fluoride, and 134.8 mg (0.59 mmol) of benzyltriethylammonium chloride were added to a solution of 1.51 g (5.97 mmol) of phenylthio (trimethylsilyl)methyl isothiocyanate, synthesized according to a document (J. Chem. Soc., Perkin Trans 1 1984, 435.), in acetonitrile (36 ml), and the mixture was stirred at room temperature overnight. The solvent was removed from the reaction solution by distillation, and the water and chloroform were then added to the residue. The aqueous layer was extracted with chloroform. The organic layer was washed with saturated brine and was then dried over anhydrous sodium sulfate. The solvent was removed by distillation. The residue was purified by column chromatography on silica gel (n-hexane:ethyl acetate=5:1→1:1) to give 302.4 mg (yield 18%) of the title compound.

Reference Example 10

3-(4-Bromophenyl)piperidine

N-Bromosuccinimide (912 mg, 5.12 mmol) was added to a solution of 1.18 g (7.32 mmol) of 3-phenylpiperidine in 50% sulfuric acid (12 ml), and the mixture was stirred at 70° C. for 30 min. A saturated aqueous potassium carbonate solution was added to the reaction solution under ice cooling, and the mixture was extracted twice with diethyl ether. The organic layer was dried over anhydrous sodium sulfate, was filtered, and was then concentrated under the reduced pressure. The residue was purified by column chromatography on silica gel (chloroform:methanol:concentrated aqueous ammonia=9: 0.6:0.06) to give 352 mg (yield 20%) of the title compound.

MS (GC) m/z 239 M$^+$, $^1$H-NMR (400 MHz, CDCl$_3$) δ: 1.53-1.66 (3H, m), 1.74-1.83 (1H, m), 1.94-2.00 (1H, m), 2.56-2.69 (3H, m), 3.06-3.16 (2H, m), 7.09 (2H, d, J=8.5 Hz), 7.42 (2H, d, J=8.5 Hz).

Reference Example 11

3-(4-Bromophenyl)-1-methylpyrrolidine

Formalin (0.0452 ml, 0.557 mmol), 0.0319 ml (0.557 mmol) of acetic acid, and 118 mg (0.557 mmol) of triacetoxy borohydride hydride were added to a solution of 42 mg (0.186 mmol) of 3-(4-bromophenyl)pyrrolidine, synthesized in the same manner as in Reference Example 1, in chloroform-ethanol 3:1 (2 ml), and the mixture was stirred at room temperature for 40 min. The reaction solution was diluted with ethyl acetate, and the diluted solution was washed with a 10% aqueous sodium hydrogencarbonate solution. The organic layer was dried over anhydrous sodium sulfate, was filtered, and was then concentrated under the reduced pressure to give 43 mg (yield 97%) of the title compound.

MS (GC) m/z 239 M$^+$, $^1$H-NMR (400 MHz, CDCl$_3$) δ: 1.71-1.88 (1H, m), 2.29-2.50 (5H, m), 2.61-2.69 (1H, m), 2.72-2.80 (1H, m), 2.94-3.00 (1H, m), 3.28-3.38 (1H, m), 7.15 (2H, d, J=8.3 Hz), 7.40 (2H, d, J=8.3 Hz).

Step (i) of Example 1

2,3,4-Tri-o-trimethylsilyl lincomycin

Trimethylsilyl chloride (90 ml, 71 mmol) and 65 ml (60 mmol) of hexamethyldisilazane were added to a solution of 50 g (122 mmol) of lincomycin in pyridine (200 ml) under ice cooling, and the mixture was stirred at room temperature for 2 hr. The solvent was removed by distillation, and the residue was diluted with hexane, followed by washing twice with water. The solvent was removed by distillation. An 80% aqueous acetic acid solution (22.5 ml) was added to a solution of the residue in methanol (150 ml), and the mixture was stirred at room temperature for 16 hr. A saturated aqueous sodium hydrogencarbonate solution (30 ml) was added to the reaction solution. The solvent was removed by distillation, and the residue was then diluted with hexane, followed by washing twice with water. The solvent was removed by distillation to give 69.5 g (yield 91%) of the title compound.

$^1$H-NMR (300 MHz, CDCl$_3$) δ: 0.25-0.45 (27H, m).

Step (ii) of Example 1

7-o-Methylsulfonyl-2,3,4-tri-o-trimethylsilyl lincomycin

Triethylamine (2.45 ml, 16.1 mmol) and 0.99 ml (12.8 mmol) of methylsulfonyl chloride were added to a solution of 4.0 g (6.42 mmol) of the title compound in step (i) of Example 1 in chloroform (20 ml) under ice cooling, and the mixture was stirred at room temperature for 3 hr. The reaction solution was diluted with 150 ml of chloroform. A 10% aqueous sodium hydrogencarbonate solution (150 ml) was then added to the diluted solution for washing. The organic layer was dried over anhydrous sodium sulfate. After filtration, the filtrate was concentrated, and the residue was purified by column chromatography on silica gel (n-hexane:ethyl acetate=100:0 to 75:25) to give 4.2 g (yield 93%) of the title compound.

Step (iii) of Example 1

7-Acetylthio-7-deoxy-7-epi-2,3,4-tri-o-trimethylsilyl lincomycin

Potassium thioacetate (163 mg, 1.43 mmol) was added to a solution of 200 mg (0.285 mmol) of the title compound in step (ii) of Example 1 in N,N-dimethylformamide (0.65 ml), and the mixture was stirred at 60° C. for 4 hr. The reaction solution was diluted with 50 ml of ethyl acetate, and 50 ml of a 10% aqueous sodium hydrogencarbonate solution was then added to the diluted solution for washing. The organic layer was dried over anhydrous sodium sulfate. After filtration, the filtrate was concentrated, and the residue was purified by column chromatography on silica gel (hexane:ethyl acetate=100:0 to 75:25) to give 170 mg (yield 88%) of the title compound.

$^1$H-NMR (400 MHz, CDCl$_3$) δ: 0.12-0.17 (27H, m), 2.31 (3H, s), 2.40 (3H, s), 5.18 (1H, d, J=5.6 Hz).

MS (API) m/z: 422 (M$^+$+1).

Step (iv) of Example 1

7-Acetylthio-7-deoxy-7-epilincomycin

To a solution of 10.6 g (15.6 mmol) of the title compound in step (iii) of Example 1 in methanol (50 ml) was added 38.9 ml of 2 N hydrochloric acid. The mixture was stirred at room temperature for 10 min. A 10% aqueous sodium hydrogencarbonate solution (30 ml) was added to the reaction solution, and methanol was removed by distillation under the reduced pressure. Ethyl acetate (250 ml) and 250 ml of 10% brine were added to the residue to perform extraction. The organic layer was dried over anhydrous sodium sulfate. After filtration, the filtrate was concentrated, and the residue was purified by column chromatography on silica gel (ethyl acetate:methanol=100:0 to 95:5) to give 7.05 g (yield 97%) of the title compound.

$^1$H-NMR (400 MHz, CDCl$_3$) δ: 2.38 (3H, s), 2.41 (3H, s), 5.31 (1H, d, J=5.6 Hz).

Step (v) of Example 1

7-Deoxy-7-epi-7-mercaptolinco mycin

Sodium methoxide (2.46 g, 45.5 mmol) was added to a solution of 7.05 g (15.2 mmol) of the title compound in step (iv) of Example 1 in methanol (50 ml), and the mixture was stirred at room temperature for 20 min. The reaction solution was neutralized by the addition of a saturated aqueous ammonium chloride solution, and methanol was then removed by distillation under the reduced pressure. A 10% aqueous sodium hydrogencarbonate solution (300 ml) was added to the residue, and the mixture was extracted with 300 ml of ethyl acetate. The organic layer was dried over anhydrous sodium sulfate. After filtration, the filtrate was concentrated, and the residue was purified by column chromatography on silica gel (chloroform:methanol:28% aqueous ammonia=95:5:0.1) to give 6.06 g (yield 94%) of the title compound.

$^1$H-NMR (400 MHz, CDCl$_3$) δ: 2.23 (3H, s), 2.42 (3H, s), 5.34 (1H, d, J=5.6 Hz).

MS (EI) m/z: 422 (M$^+$).

Step (vi) of Example 1

7-Deoxy-7-epi-7-(4-(pyrimidin-5-yl)phenylthio) lincomycin (compound I)

5-(4-Bromophenyl)pyrimidine (77.0 mg, 0.33 mmol) and 0.058 ml (0.33 mmol) of diisopropylethylamine were added to a solution of 70 mg (0.17 mmol) of the title compound produced in step (v) of Example 1, 9.7 mg (0.017 mmol) of 4,5-bis(diphenylphosphino)-9,9-dimethylsantene, and 7.6 mg (0.0084 mmol) of tris(dibenzylideneacetone)dipalladium in dioxane (1 ml), and the mixture was heated under reflux for 6 hr. A saturated aqueous sodium hydrogencarbonate solution (15 ml) was added to stop the reaction, and the insolubles were removed by filtration through Celite, followed by extraction with ethyl acetate (30 ml). The organic layer was washed with water and saturated brine and was then dried over anhydrous sodium sulfate. After filtration, the filtrate was concentrated, and the residue was purified by preparative thin-layer chromatography (chloroform:methanol:28% aqueous ammonia=9:2:0.2) to give 77.2 mg (yield 79%) of the title compound.

For the title compound (1) produced in step (vi) of Example 1 and compounds (2 to 48) produced in the same manner as in step (vi) of Example 1, $^1$H-NMR data and MS data are shown in Tables 2 to 4.

Example 2

7-(6-(3-Aminopyrrolidin-1-yl)pyridin-3-ylthio)-7-deoxy-7-epilincomycin (compound 49)

The procedure of step (vi) of Example 1 was repeated, except that 100 mg (0.24 mmol) of the title compound in step (v) of Example 1 and 100 mg (0.29 mmol) of tert-butyl 1-(5-bromopyridin-2-yl)pyrrolidin-3-ylcarbamate were used. Trifluoroacetic acid (0.5 ml) was added to the residue, and the mixture was stirred at room temperature for 30 min.

Diisopropyl ether (10 ml) was added to the reaction solution, and the resultant precipitate was purified by preparative thin-layer chromatography (chloroform:methanol:28% aqueous ammonia=9:2:0.2) to give 87.2 mg (yield 62%) of the title compound.

For the title compound (49) produced in Example 2 and compounds (47 and 48) produced in the same manner as in Example 2, $^1$H-NMR data and MS data are shown in Table 4.

Step (i) of Example 3

7-Deoxy-7-epi-7-(4-(pyridin-3-yl)phenylthio)lincomycin

The title compound (136 mg, yield 88%) was produced in the same manner as in step (vi) of Example 1, except that 113 mg (0.268 mmol) of the title compound produced in step (v) of Example 1 and 118 mg (0.502 mmol) of 3-(4-bromophenyl)pyridine were used.

MS (FAB) m/z: 576 (M$^+$+1). $^1$H-NMR (300 MHz, CD$_3$OD) δ: 1.96 (3H, s), 2.39 (3H, s), 3.93 (1H, dq, J=2.7, 6.6 Hz), 5.27 (1H, d, J=5.7 Hz), 7.47-7.51 (1H, m), 7.52 (2H, d, J=8.4 Hz), 7.63 (2H, d, J=8.4 Hz), 8.07 (1H, ddd, J=1.5, 2.4, 8.1 Hz), 8.49 (1H, dd, J=1.5, 4.8 Hz), 8.78 (1H, dd, J=0.9, 2.7 Hz)

MS (FAB) m/z: 576 (M$^+$+1). .

Step (ii) of Example 3

7-Deoxy-7-epi-7-(4-(piperidin-3-yl)phenylthio)lincomycin (compound 50)

1 N Hydrochloric acid (0.5 ml) and 81.8 mg of platinum (black) were added to a solution of 80.2 mg (0.139 mmol) of the title compound, produced in step (i) of Example 3 in methanol (5 ml), and the mixture was stirred in a hydrogen atmosphere at room temperature for 27 hr. Platinum (black) (81.8 mg) was added thereto, and the mixture was stirred in a hydrogen atmosphere at room temperature for additional 6 days. Platinum (black) (80.8 mg) was added thereto, and the mixture was stirred in a hydrogen atmosphere at room temperature for additional 5 days. Platinum (black) (79.9 mg) was added thereto, and the mixture was stirred in a hydrogen atmosphere at room temperature for additional 2 days. The reaction solution was filtered through Celite and was washed with methanol. The filtrate was concentrated under the reduced pressure, and the residue was purified by preparative thin-layer chromatography (chloroform:methanol:aqueous ammonia=4:1:0.1) to give 47.9 mg (yield 59%) of the title compound.

For the title compound (50) produced in step (ii) of Example 3, $^1$H-NMR data and MS data are shown in Table 4.

Example 4

7-Deoxy-7-epi-7-(4-(1-methylpiperidin-3-yl)phenylthio)lincomycin (compound 51)

Acetic acid (17.5 µl, 0.306 mmol), 23 µl (0.309 mmol) of a 37% aqueous formaldehyde solution, and 68.2 mg (0.306 mmol) of sodium triacetoxy boron were added to a solution of 17.9 mg (0.0308 mmol) of the title compound, produced in step (ii) of Example 3, in methanol (1 ml), and the mixture was stirred at room temperature for 44 min. The solvent was removed by distillation, and the residue was purified by preparative thin-layer chromatography (chloroform:methanol:aqueous ammonia=5:1:0.1) to give 13.9 mg (yield 76%) of the title compound.

For the title compound (51) produced in Example 4 and compounds (52 to 54) produced in the same manner as in Example 4, $^1$H-NMR data and MS data are shown in Table 4.

Example 5

7-(4-(1-Acetylpiperidin-3-yl)phenylthio)-7-deoxy-7-epilincomycin (compound 55)

Triethylamine (66 µl, 0.468 mmol) and 17 µl (0.234 mmol) of acetyl chloride were added under ice cooling to a solution of 22.8 mg (0.0392 mmol) of the title compound, produced in step (ii) of Example 3, in chloroform (1 ml), and the mixture was stirred for 2 hr. The reaction solution was diluted with 10 ml of ethyl acetate, and the diluted solution was washed with a saturated aqueous ammonium chloride solution. The aqueous layer was extracted twice with 3 ml of ethyl acetate. The organic layers were combined and were washed with 25% brine, were dried over anhydrous sodium sulfate, and were then filtered. The filtrate was concentrated under the reduced pressure, and the residue was purified by preparative thin-layer chromatography (chloroform:methanol:aqueous ammonia=10:1:0.1) to give 14.9 mg (yield 61%) of the title compound.

For the title compound (55) of Example 5, $^1$H-NMR data and MS data are shown in Table 4.

Example 6

7-Deoxy-7-epi-7-(4-(1-ethylpiperidin-3-yl)phenylthio)lincomycin (compound 56)

P-Toluenesulfonehydrazide (294 mg, 1.53 mmol) was added to a solution of 46.5 mg (0.0765 mmol) of 7-deoxy-7-epi-7-(4-(1-ethyl-1,2,3,6-tetrahydropyridin-3-yl)phenylthio)lincomycin (compound 34), produced in the same manner as in step (vi) of Example 1, in toluene (2.5 ml), and the mixture was heated under reflux with stirring for 3 hr. p-Toluenesulfonehydrazide (295 mg, 1.53 mmol) was added to the reaction solution, and the mixture was heated under reflux with stirring for additional 3 hr. The reaction solution was diluted with 10 ml of ethyl acetate, and the diluted water was washed with a 1 N aqueous sodium hydroxide solution. The aqueous layer was extracted twice with 5 ml of ethyl acetate. The organic layers were combined and were washed with 25% brine, were dried over anhydrous sodium sulfate, and were then filtered. The filtrate was concentrated under the reduced pressure, and the residue was purified by preparative thin-layer chromatography (chloroform:methanol:aqueous ammonia=10:1:0.1) to give 5.5 mg (yield 12%) of the title compound.

For the title compound (56) produced in Example 6 and the compound (57) produced in the same manner as in Example 6, $^1$H-NMR data and MS data are shown in Table 4.

Step (i) of Example 7

Benzyl(S)-1-tert-butoxycarbonyl-5-oxopyrrolidine-2-carboxylate

The title compound (two steps, 200 g, yield 94%) was produced from (S)-5-oxopyrrolidine-2-carboxylic acid in the same manner as described in Tetrahedron Lett., 43, (2002), 3499.

Step (ii) of Example 7

Benzyl(2S,4R)-4-aryl-1-tert-butoxycarbonylpyrrolidine-2-carboxylate

The title compound (three steps, 95.1 g, yield 51%) was produced from the title compound produced in step (i) of Example 7 in the same manner as described in Tetrahedron Lett., 35, (1994), 2053 and J. Am. Chem. Soc., 110, (1998), 3894.

Step (iii) of Example 7

1'-Tert-butoxycarbonyl-1'-demethyl-2,3,4-tri-o-trimethylsilyl lincomycin

Pd—C (5 g) was added to a solution of 30.2 g (87.4 mmol) of the title compound, produced in step (ii) of Example 7, in methanol (350 ml) in an argon atmosphere. The mixture was then stirred in a hydrogen atmosphere at room temperature for 7.5 hr. The insolubles were removed by filtration through Celite. The filtrate was concentrated under the reduced pressure. 1-Hydroxybenzotriazole (17.7 g, 131.1 mmol), 27.1 g (131.1 mmol) of dicyclohexylcarbodiimide, and 33.2 g (131.1 mmol) of methyl 1-thio-α-lincosamide were added in that order to a solution of the residue in pyridine (207 ml), and the mixture was stirred at room temperature for 16 hr.

Water was added to the reaction solution, and the resultant precipitate was removed by filtration. The filtrate was concentrated to dryness. The title compound (four steps, 18.2 g) was produced using the half amount of the residue in the same manner as in step (i) of Example 1.

$^1$H-NMR (400 MHz, CDCl$_3$) δ: 0.12 (9H, s), 0.12 (9H, s), 0.15 (9H, s), 1.34 (9H, s), 1.92 (3H, s), 5.05 (1H, brd, J=5.4 Hz).

Step (iv) of Example 7

1'-Tert-butoxycarbonyl-1'-demethyl-7-o-methylsulfonyl-2,3,4-tri-o-trimethylsilyl lincomycin The procedure of step (ii) of Example 1 was repeated, except that 5 g (7.1 mmol) of the title compound produced in step (iii) of Example 7, chloroform (22 ml), 2.5 ml (17.6 mmol) of triethylamine, and 1.1 ml (14.1 mmol) of methylsulfonyl chloride were used. Thus, the title compound was produced as a crude product.

Step (v) of Example 7

7-Acetylthio-1'-tert-butoxycarbonyl-1'-demethyl-7-deoxy-7-epi-2,3,4-tri-o-trimethylsilyl lincomycin The title compound (218 mg, yield 40%) was produced in the same manner as in step (iii) of Example 1, except that 555 mg (0.705 mmol) of the title compound produced in step (iv) of Example 7 was used.

$^1$H-NMR (300 MHz, CDCl$_3$) δ: 0.13-0.16 (27H, m), 1.51 (9H, s), 1.99 (3H, s), 2.29 (3H, s), 4.02 (1H, dq, J=2.4, 6.9 Hz), 5.16 (1H, d, J=5.4 Hz).

MS (API) m/z: 767 (M$^+$+1).

Step (vi) of Example 7

7-Acetylthio-1'-tert-butoxycarbonyl-1'-demethyl-7-deoxy-7-epilincomycin

The title compound (137 mg, yield 88%) was produced in the same manner as in step (iv) of Example 1, except that 218 mg (0.284 mmol) of the title compound produced in step (v) of Example 7 was used.

$^1$H-NMR (300 MHz, CD$_3$OD) δ: 1.47 (9H, s), 2.01 (3H, s), 2.32 (3H, s), 3.96 (1H, dq, J=2.4, 6.9 Hz), 5.21 (1H, d, J=5.7 Hz).

MS (API) m/z: 551 (M$^+$+1).

Step (vii) of Example 7

1'-Tert-butoxycarbonyl-1'-demethyl-7-deoxy-7-epi-7-mercaptolincomycin

The title compound (120 mg, yield 95%) was produced in the same manner as in step (v) of Example 1, except that 137 mg (0.249 mmol) of the title compound produced in step (vi) of Example 7 was used.

$^1$H-NMR (300 MHz, CD$_3$OD) δ: 1.47 (9H, s), 2.15 (3H, s), 3.40-3.52 (1H, m), 5.25 (1H, d, J=5.7 Hz).

MS (FAB$^+$) m/z: 509 (M$^+$+1).

Step (viii) of Example 7

1'-Tert-butoxycarbonyl-1'-demethyl-7-deoxy-7-epi-7-(4-(pyrimidin-5-yl)phenylthio)lincomycin The title compound (118 mg, yield 78%) was produced in the same manner as in step (vi) of Example 1, except that 116 mg (0.229 mmol) of the title compound produced in step (vii) of Example 7 and 107 mg (456 mmol) of 5-(4-bromophenyl)pyrimidine were used.

$^1$H-NMR (300 MHz, CD$_3$OD) δ: 1.48 (9H, s), 1.92 (3H, s), 5.28 (1H, d, J=5.4 Hz), 7.54 (2H, d, J=8.4 Hz), 7.69 (2H, d, J=8.1 Hz), 9.07 (2H, s), 9.13 (1H, s).

MS (FAB) m/z: 663 (M$^+$+1).

Step (ix) of Example 7

1'-Demethyl-7-deoxy-7-epi-7-(4-(pyrimidin-5-yl)phenylthio)lincomycin (compound 58)

A solution of 118 mg (0.178 mmol) of the title compound, produced in step (ix) of Example 7, in dichloromethane (2.5 ml) was cooled to −20° C. Trifluoroacetic acid (0.265 ml, 3.53 mmol) was added to the cooled solution, and the mixture was stirred under ice cooling for 10 min and was stirred at room temperature for 5.5 hr. Methanol (1 ml) was added to the reaction solution. The mixture was concentrated under the reduced pressure, and the residue was purified by preparative thin-layer chromatography (chloroform:methanol:aqueous ammonia=5:1:0.1) to give 82.2 mg (yield 82%) of the title compound.

For the title compound (58) produced in step (ix) of Example 7, $^1$H-NMR data and MS data are shown in Table 4.

Step (i) of Example 8

Methyl 6-N-((2S,4R)-1-tert-butoxycarbonyl-4-propyl)pipecoloyl-2,3,4-tri-o-trimethylsilyl-1-thio-α-lincosamide Platinum (IV) oxide (79.8 mg, 0.35 mmol) was added to a solution of 1.05 g (5.22 mmol) of 4-propylpyridine-2-carboxylic acid hydrochloride, produced in the same manner as described in J. Med. Chem., 27, (1984), 216, in acetic acid (8 ml). The mixture was stirred in a hydrogen atmosphere (ordinary pressure) for 24 hr. The reaction solution was filtered through Celite. The solvent was then removed by distillation to give 9.9 g of a crude crystal of 4-propylpiperidine-2-carboxylic acid acetate. Di-tert-butyl dicarbonate (11.9 ml, 52 mmol) and 43 ml of a 2 N aqueous sodium hydroxide solution were added in that order to a solution of the crude crystal in tert-butylalcohol (40 ml), and the mixture was stirred at room temperature for 24 hr. The solvent was removed by distillation. Water and diethyl ether were then added to the residue. Ethyl acetate and 2 N hydrochloric acid were added to the aqueous layer, and the mixture was extracted with ethyl acetate. The organic layer was washed with saturated brine and was then dried over anhydrous sodium sulfate. After filtration, the solvent was removed from the filtrate by ditillation to give 7.9 g (yield 68%) of 1-(tert-butoxycarbonyl)-4-propylpipecolic acid.

Methyl 6-N-((2S,4R)-1-(tert-butoxycarbonyl)-4-propyl)pipecoloyl-1-thio-α-lincosamide (14.5 g, yield 99%) was produced in the same manner as in step (iii) of Example 7, except that 7.9 g of 1-(tert-butoxycarbonyl)-4-propylpipecolic acid, 10.96 g (43.5 mmol) of methyl 1-thio-α-lincosamide, 8.95 g (43.4 mmol) of dicyclohexylcarbodiimide, 5.86 g (43.4 mmol) of 1-hydroxybenzotriazole, and 85 ml of N,N-dimethylformamide were used.

The title compound (0.80 g, yield 41%) was produced in the same manner as in step (i) of Example 1, except that 1.35 g (2.68 mmol) of methyl 6-N-((2S,4R)-1-(tert-butoxycarbonyl)-4-propyl)pipecoloyl-1-thio-α-lincosamide was used.

$^1$H-NMR (400 MHz, CDCl$_3$) δ: 0.11 (18H, s), 0.16 (9H, s), 1.33 (9H, s), 5.14 (1H, d, J=5.4 Hz), 6.32 (1H, brd, J=8.7 Hz).

MS (FAB$^+$) m/z: 724 (M$^+$+1).

Step (ii) of Example 8

Methyl 7-acetylthio-6-N-((2S,4R)-1-tert-butoxycarbonyl-4-propyl)pipecoloyl-7-deoxy-7-epi-1-thio-2,3,4-tri-o-trimethylsilyl-α-lincosamide The title compound (357 mg, yield 69%) was produced in the same manner as in steps (ii) and (iii) of Example 1, except that 530 mg (0.662 mmol) of the title compound produced in step (i) of Example 8 was used.

$^1$H-NMR (400 MHz, CDCl$_3$) δ: 0.13 (18H, m), 0.18 (9H, s), 0.88 (3H, t, J=6.6 Hz), 1.35 (3H, d, J=6.2 Hz), 1.49 (9H, s), 1.99 (3H, s), 2.29 (3H, s), 5.15 (1H, d, J=5.6 Hz).

MS (FAB$^+$) m/z: 781 (M$^+$+1).

Step (iii) of Example 8

Methyl 7-acetylthio-6-N-((2S,4R)-1-tert-butoxycarbonyl-4-propyl)pipecoloyl-7-deoxy-7-epi-1-thio-α-lincosamide The title compound (250 mg) was produced in the same manner as in step (iv) of Example 1, except that 341 mg (0.436 mmol) of the title compound produced in step (ii) of Example 8 was used.

$^1$H-NMR (400 MHz, CDCl$_3$) δ: 0.90 (3H, t, J=7.3 Hz), 1.43 (3H, d, J=7.3 Hz), 1.46 (9H, s), 2.15 (3H, s), 2.36 (3H, s), 5.29 (1H, d, J=5.6 Hz).

MS (FAB$^+$) m/z: 565 (M$^+$+1).

Step (iv) of Example 8

Methyl 6-N-((2S,4R)-1-tert-butoxycarbonyl-4-propyl)pipecoloyl-7-deoxy-7-epi-7-mercapto-1-thio-α-lincosamide The title compound (234 mg, yield 96%) was produced in the same manner as in step (v) of Example 1, except that 244 mg (0.432 mmol) of the title compound produced in step (iii) of Example 8 was used.

$^1$H-NMR (400 MHz, CDCl$_3$) δ: 0.90 (3H, t, J=7.1 Hz), 1.47 (9H, s), 2.22 (3H, s), 5.33 (1H, d, J=5.6 Hz).

MS (FAB$^+$) m/z: 523 (M$^+$+1).

Step (v) of Example 8

Methyl 6-N-((2S,4R)-1-tert-butoxycarbonyl-4-propyl)pipecoloyl-7-deoxy-7-epi-7-(4-(pyrimidin-5-yl)phenylthio)-1-thio-α-lincosamide The title compound (163 mg, yield 83%) was produced in the same manner as in step (vi) of Example 1, except that 152 mg (0.291 mmol) of the title compound produced in step (iv) of Example 8 and 103 mg (0.440 mmol) of 5-(4-bromophenyl)pyrimidine were used.

¹H-NMR (300 MHz, CD₃OD) δ: 1.46 (9H, s), 1.92 (3H, s), 5.30 (1H, d, J=5.7 Hz), 7.54 (2H, d, J=8.1 Hz), 7.69 (2H, d, J=8.7 Hz), 9.07 (2H, s), 9.13 (1H, s).
MS (FAB) m/z: 677 (M⁺+1).

Step (vi) of Example 8

Methyl 7-deoxy-7-epi-6-N-((2S,4R)-4-propyl)pipecolyl-7-(4-(pyrimidin-5-yl)phenylthio)-1-thio-α-lincosamide (compound 59)

The title compound (123 mg, yield 88%) was produced in the same manner as in step (ix) of Example 7, except that 163 mg (0.241 mmol) of the title compound produced in step (v) of Example 8 was used.

For the title compound (59) produced in step (vi) of Example 8 and compounds (60 to 64) produced in the same manner as in step (vi) of Example 8, ¹H-NMR data and MS data for these compounds are shown in Table 4.

Example 9

Methyl-7-deoxy-7-epi-6-N-(2S,4R)-1-methyl-4-propyl)pipecolyl-7-(4-(pyrimidin-5-yl)phenylthio)-1-thio-α-lincosamide (compound 65)

The title compound (58.6 mg, yield 94%) was produced in the same manner as in Example 4, except that 60.8 mg (0.105 mmol) of the title compound produced in step (vii) of Example 8 was used.

For the title compound (65) produced in Example 9, ¹H-NMR data and MS data are shown in Table 4.

Step (i) of Example 10

Methyl 6-N-((2S,4R)-1-tert-butoxycarbonyl-4-butyl)pipecoloyl-2,3,4-tri-o-trimethylsilyl-1-thio-α-lincosamide The title compound (five steps, 11.4 g, yield 31%) was produced in the same manner as in steps (i) and (ii) of Example 8, except that 10.8 g (50 mmol) of 4-butylpyridine-2-carboxylic acid hydrochloride was used.

¹H-NMR (400 MHz, CDCl₃) δ: 0.14 (18H, m), 0.19 (9H, s), 0.88 (3H, m), 1.15 (3H, d, J=6.6 Hz), 5.17 (1H, d, J=5.4 Hz).
MS (FAB⁺) m/z: 737 (M⁺+1).

Step (ii) of Example 10

Methyl 7-acetylthio-6-N-((2S,4R)-1-tert-butoxycarbonyl-4-butyl)pipecolyl-7-deoxy-7-epi-1-thio-2,3,4-tri-o-trimethylsilyl-α-lincosamide A crude product (1.17 g) of methyl 6-N-((2S,4R)-1-tert-butoxycarbonyl-4-butyl)pipecolyl-7-o-methanesulfonyl-1-thio-2,3,4-o-trimethylsilyl-α-lincosamide was produced in the same manner as in step (ii) of Example 1, except that 1.01 g (1.37 mmol) of methyl 6-N-((2S,4R)-1-tert-butoxycarbonyl-4-butyl)pipecolyl-1-thio-2,3,4-o-trimethylsilyl-α-lincosamide was used. The title compound (565 mg, yield 52%) was produced from 1.17 g of the crude product in the same manner as in step (iii) of Example 1.

¹H-NMR (300 MHz, CDCl₃) δ: 0.13 (9H, s), 0.13 (9H, s), 0.18 (9H, s), 1.49 (9H, s), 1.99 (3H, s), 2.29 (3H, s), 5.15 (1H, d, J=5.4 Hz).
MS (FAB) m/z: 795 (M⁺+1).

Step (iii) of Example 10

Methyl 7-acetylthio-6-N-((2S,4R)-1-tert-butoxycarbonyl-4-butyl)pipecolyl-7-deoxy-7-epi-α-lincosamide The title compound (378 mg, yield 92%) was produced in the same manner as in step (iv) of Example 1, except that 565 mg (0.711 mmol) of the title compound produced in step (ii) of Example 10 was used.

¹H-NMR (300 MHz, CD₃OD) δ: 1.38 (9H, s), 1.94 (3H, s), 2.25 (3H, s), 5.16 (1H, d, J=5.7 Hz).
MS (FAB) m/z: 579 (M⁺+1).

Step (iv) of Example 10

Methyl 6-N-((2S,4R)-1-tert-butoxycarbonyl-4-butyl)pipecoloyl-7-deoxy-7-epi-7-mercapto-1-thio-α-lincosamide The title compound (373 mg, yield 100%) was produced in the same manner as in step (v) of Example 1, excecpt that 378 mg (0.652 mmol) of the title compound produced in step (iii) of Example 10 was used.

¹H-NMR (300 MHz, CD₃OD) δ: 1.46 (9H, s), 2.15 (3H, s), 5.26 (1H, d, J=5.7 Hz).
MS (FAB) m/z: 537 (M⁺+1).

Step (v) of Example 10

Methyl 6-N-((2S,4R)-1-tert-butoxycarbonyl-4-butyl)pipecoloyl-7-deoxy-7-epi-7-(4-(pyrimidin-5-yl)phenylthio)-1-thio-α-lincosamide The title compound (151 mg, yield 78%) was produced in the same manner as in step (vi) of Example 1, except that 150 mg (0.280 mmol) of the title compound produced in step (iv) of Example 10 and 99.3 mg (0.422 mmol) of 5-(4-bromophenyl)pyrimidine were used.

¹H-NMR (300 MHz, CD₃OD) δ: 1.46 (9H, s), 1.92 (3H, s), 5.28 (1H, d, J=5.7 Hz), 7.55 (2H, d, J=8.4 Hz), 7.68 (2H, d, J=8.1 Hz), 9.07 (2H, s), 9.13 (1H, s).

Step (vi) of Example 10

Methyl 6-N-((2S,4R)-4-butyl)pipecoloyl-7-deoxy-7-epi-7-(4-(pyrimidin-5-yl)phenylthio)-1-thio-α-lincosamide (compound 66)

The title compound (103 mg, yield 80%) was produced in the same manner as in step (ix) of Example 7, except that 151 mg (0.218 mmol) of the title compound produced in step (v) of Example 10 was used.

For the title compound (66) produced in step (vi) of Example 10, ¹H-NMR data and MS data are shown in Table 4.

Example 11

Methyl 6-N-((2S,4R)-4-butyl-1-methyl)pipecoloyl-7-deoxy-7-epi-7-(4-(pyrimidin-5-yl)phenylthio)-1-thio-α-lincosamide (compound 67)

The title compound (54.3 mg, yield 98%) was produced in the same manner as in Example 4, except that 54.4 mg (0.092 mmol) of the title compound produced in step (vi) of Example 10 was used.

For the title compound (67) produced in Example 11, ¹H-NMR data and MS data are shown in Table 5.

Step (i) of Example 12

4-Cyclopropylmethylpyridine

A solution of 19.5 ml (200 mmol) of 4-picoline in tetrahydrofuran (120 ml) was cooled to −78° C. Lithium diisopropylamide (2 M heptane, tetrahydrofuran, ethylbenzene solution) (200 ml) was added dropwise to the cooled solution over a period of 20 min, and the mixture was stirred at −40° C. for 20 min and was then cooled to −78° C. Cyclopropyl bromide (16.0 ml, 200 mmol) was added dropwise to the reaction solution over a period of 25 min, and the mixture was stirred at −78° C. for one hr. The reaction solution was then added to 300 ml of a saturated aqueous ammonium chloride solution, and the mixture was washed with 100 ml of water. The solution was extracted twice with 200 ml of ethyl acetate, and the extract was dried over anhydrous sodium sulfate. After filtration, the filtrate was concentrated, and the residue was purified by distillation under the reduced pressure (8 mmHg, 86 to 87° C.) and column chromatography on silica gel (hexane:ethyl acetate=70:30) to give 17.6 g (yield 66%) of the title compound.

¹H-NMR (400 MHz, CDCl₃) δ: 0.19-0.25 (2H, m), 0.55-0.61 (2H, m), 0.93-1.04 (1H, m), 2.54 (2H, d, J=7.1 Hz), 7.17-7.22 (2H, m), 8.47-8.52 (2H, m).

MS (FAB) m/z 134 (M+1)⁺.

Step (ii) of Example 12

4-Cyclopropylmethylpyridine-N-oxide

Meta-chloroperbenzoic acid (42.7 g, purity>65%) was added to a solution of 21.4 g (161 mmol) of the title compound, produced in step (i) of Example 12, in dichloromethane (240 ml), and the mixture was stirred at room temperature for 1 hr 20 min. A 20% (w/v) sodium thiosulfate pentahydrate solution (120 ml) was added to the reaction solution, and the mixture was stirred at room temperature for one hr. A saturated aqueous sodium hydrogencarbonate solution (200 ml) and 50 ml of a saturated aqueous potassium carbonate solution were added to the reaction solution, and the mixture was extracted thrice with a mixed solution composed of chloroform and isopropanol (8:1, 450 ml). The extract was dried over anhydrous sodium sulfate. After filtration, the filtrate was concentrated to give 23.9 g (yield 100%) of the title compound.

¹H-NMR (400 MHz, CDCl₃) δ: 0.19-0.27 (2H, m), 0.58-0.66 (2H, m), 0.90-1.02 (1H, m), 2.54 (2H, d, J=7.1 Hz), 7.21 (2H, d, J=6.8 Hz), 8.15 (2H, d, J=6.8 Hz).

Step (iii) of Example 12

2-Cyano-4-cyclopropylmethylpyridine

Trimethylsilyl cyanide (25.8 ml, 0.193 mmol) was added to a solution of 23.9 g (160 mmol) of the title compound In step (ii) of Example 12 in dichloromethane (300 ml). Dimethylcarbamic acid chloride (17.8 ml, 193 mmol) was added in three divided portions at intervals of 20 min. The mixture was stirred at room temperature for 24 hr. A 10% (w/v) aqueous potassium carbonate solution (300 ml) was added to the reaction solution, and the mixture was stirred for 30 min. Dichloromethane (100 ml) was then added to the reaction solution, followed by extraction. Dichloromethane (200 ml) was added to the aqueous layer, followed by extraction. The organic layers were combined and were dried over anhydrous sodium sulfate. After filtration, the filtrate was concentrated, and the residue thus obtained was purified by column chromatography on silica gel (hexane:ethyl acetate=100:0→85:15) to give 22.6 g (yield 89%) of the title compound.

¹H-NMR (400 MHz, CDCl₃) δ: 0.22-0.29 (2H, m), 0.62-0.68 (2H, m), 0.93-1.04 (1H, m), 2.61 (2H, d, J=7.1 Hz), 7.41-7.45 (1H, m), 7.63-7.66 (1H, m), 8.58-8.62 (1H, m).

MS (EI) m/z 158 M⁺.

Step (iv) of Example 12

4-(Cyclopropylmethyl)picolinic acid

A 5 N aqueous sodium hydroxide solution (250 ml) was added to a solution of 25.5 g (161 mmol) of the title compound in step (iii) of Example 12 in methanol (250 ml), and the mixture was stirred at 50° C. for 8 hr. 5 N hydrochloric acid (250 ml) was added to the reaction solution under ice cooling. The mixture was then rendered weakly acidic by the addition of 1 N hydrochloric acid. The adjusted solution was extracted seven times with a mixed solution composed of chloroform and isopropanol (5:1, 600 ml). The organic layers were combined and dried over anhydrous sodium sulfate. After filtration, the filtrate was concentrated to give 27.6 g (yield 97%) of the title compound.

¹H-NMR (400 MHz, CDCl₃) δ: 0.24-0.30 (2H, m), 0.60-0.67 (2H, m), 0.98-1.08 (1H, m), 2.67 (2H, d, J=7.1 Hz), 7.48-7.53 (1H, m), 8.15-8.19 (1H, m), 8.52-8.56 (1H, m).

MS (FAB) m/z 178 (M+H)⁺.

Step (v) of Example 12

Methyl 6-N-((2S,4R)-1-tert-butoxycarbonyl-4-cyclopropylmethyl)pipecoloyl-1-thio-2,3,4-tri-o-trimethylsilyl-α-lincosamide Methyl 6-N-((2S,4R)-1-tert-butoxycarbonyl-4-cyclopropylmethyl)pipecoloyl-1-thio-α-lincosamide (three steps, 35.0 g, yield 40%) was produced in the same manner as in step (i) of Example 8, except that 30.0 (168 mmol) of the title compound produced in step (iv) of Example 12 was used. The title compound (30.6 g, yield 62%) was produced in the same manner as in step (i) of Example 1, except that 35.0 g (67.5 mmol) of methyl 6-N-((2S,4R)-1-tert-butoxycarbonyl-4-cyclopropylmethyl)pipecoloyl-1-thio-α-lincosamide was used.

¹H-NMR (400 MHz, CDCl₃) δ: −0.04-0.02 (2H, m), 0.13 (9H, s), 0.14 (9H, s), 0.19 (9H, s), 0.39-0.46 (2H, m), 0.62-0.72 (1H, m), 1.11-1.34 (6H, m), 1.47 (9H, s), 1.56-1.68 (2H, m), 1.82-1.92 (1H, m), 2.00-2.16 (4H, m), 2.86 (1H, d, J=6.6

Hz), 3.30-3.65 (3H, m), 3.88-4.23 (5H, m), 4.29-4.39 (1H, m), 5.17 (1H, d, J=5.4 Hz), 6.42 (1H, d, J=9.3 Hz).
MS (FAB) m/z 735 (M+H)+.

Step (vi) of Example 12

Methyl 6-N-((2S,4R)-1-tert-butoxycarbonyl-4-cyclopropylmethyl)pipecoloyl-7-deoxy-7-epi-7-(5-(4-(methylamino)thiazol-4-yl)-1,3,4-thiadiazol-2-ylthio)-1-thio-α-lincosamide Triphenylphosphine (52.5 mg, 0.2 mmol), 0.032 ml (0.2 mmol) of diethylazodicarboxylate, and 46.2 mg (0.2 mmol) of 5-(5-(methylamino)thiazol-4-yl)-1,3,4-thiadiazole-2-thiol were added under ice cooling to a solution of 100.0 g (0.13 mmol) of the title compound, produced in step (v) of Example 12, in toluene (2 ml). The mixture was stirred at room temperature for 16 hr. The reaction solution was post treated in the same manner as in step (vi) of Example 1 to give 98.4 mg (yield 81%) of the title compound.
$^1$H-NMR (300 MHz, CDCl$_3$) 1.51 (9H, s), 2.19 (3H, s), 3.17 (3H, d, J=5.4 Hz), 5.38 (1H, d, J=5.4 Hz), 7.51 (1H, d, J=5.4 Hz), 8.00 (1H, s).

Step (vii) of Example 12

Methyl 6-N-((2S,4R)-4-cyclopropylmethyl)pipecoloyl-7-deoxy-7-epi-7-(5-(4-(methylamino)-thiazol-4-yl)-1,3,4-thiadiazol-2-ylthio)-1-thio-α-lincosamide (compound 68)

The title compound (74.3 mg, yield 89%) was produced in the same manner as in step (ix) of Example 7, except that 95.0 (0.10 mmol) of the title compound produced in step (vi) of Example 12 was used.
For the title compound (68) produced in step (vii) of Example 12 and compounds (69 to 71) produced in the same manner as in step (vii) of Example 12, $^1$H-NMR data and MS data are shown in Table 5.

Step (i) of Example 13

Methyl 6-N-((2S,4R)-1-tert-butoxycarbonyl-4-cyclopropylmethyl)pipecoloyl-7-o-methanesulfonyl-1-thio-2,3,4-tri-o-trimethylsilyl-α-lincosamide The title compound (1.06 g, yield 96%) was produced in the same manner as in step (ii) of Example 1, except that 1.00 g (1.36 mmol) of the title compound produced in step (v) of Example 12 was used.
MS (EI) m/z 813 (M+1)+.

Step (ii) of Example 13

Methyl 7-acetylthio-6-N-((2S,4R)-1-tert-butoxycarbonyl-4-cyclopropyl methyl)pipecoloyl-7-deoxy-7-epi-1-thio-2,3,4-tri-o-trimethylsilyl-α-lincosamide The title compound (4.00 g, yield 54%) was produced in the same manner as in step (iii) of Example 1, except that 8.75 g (9.37 mmol) of the title compound produced in step (i) of Example 13 was used.
$^1$H-NMR (400 MHz, CDCl$_3$) δ: −0.03-0.05 (2H, m), 0.13 (18H, m), 0.18 (9H, s), 0.38-0.46 (2H, m), 0.62-0.73 (1H, m), 1.17-1.29 (3H, m), 1.36 (3H, d, J=6.8 Hz), 1.50 (9H, s), 1.58-1.72 (2H, m), 1.87-2.17 (5H, m), 2.29 (3H, s), 3.11 (1H, br), 3.58 (1H, dd, J=2.2, 9.5 Hz), 3.67-3.84 (3H, m), 3.88- 4.03 (2H, m), 4.12 (1H, dd, J=5.4 Hz, 9.5 Hz), 4.30-4.40 (1H, m), 4.52-4.62 (1H, m), 5.16 (1H, d, J=5.4 Hz), 6.27 (1H, br).
MS (EI) m/z 793 (M+1)+.

Step (iii) of Example 13

Methyl 6-N-((2S,4R)-1-tert-butoxycarbonyl-4-cyclopropylmethyl)pipecoloyl-7-deoxy-7-epi-7-mercapto-1-thio-α-lincosamide The title compound (3.45 g, yield 99%) was produced in the same manner as in steps (iv) and (v) of Example 1, except that 5.20 g (6.55 mmol) of the title compound produced in step (ii) of Example 13 was used.
$^1$H-NMR (400 MHz, CDCl$_3$) δ: −0.02-0.07 (2H, m), 0.41-0.48 (2H, m), 0.63-0.74 (1H, m), 1.14-1.49 (6H, m), 1.44 (1H, d, J=4.9 Hz), 1.48 (9H, s), 1.65-1.78 (2H, m), 1.86-1.97 (1H, m), 2.02-2.12 (1H, m), 2.22 (3H, s), 2.39 (1H, d, J=5.1 Hz), 2.65 (1H, d, J=10.2 Hz), 3.31 (1H, br), 3.55 (1H, dt, J=3.7, 10.0 Hz), 3.63 (1H, br), 3.70-3.79 (H, m), 3.84-3.92 (2H, m), 4.06-4.19 (2H, m), 4.26 (1H, br), 4.85 (1H, d, J=3.7 Hz), 5.33 (1H, d, J=5.6 Hz), 6.69 (1H, d, J=9.0 Hz).
MS (FAB) m/z 535 (M+1)+.

Step (iv) of Example 13

Methyl 6-N-((2S,4R)-1-tert-butoxycarbonyl-4-cyclopropylmethyl)pipecoloyl-7-deoxy-7-epi-7-(4-(1-methyl-1,2,3,6-tetrahydropyridin-3-yl)phenylthio)-1-thio-α-lincosamide The title compound (252 mg, yield 86%) was produced in the same manner as in step (vi) of Example 1, except that 222 mg (0.416 mmol) of the title compound produced in step (iii) of Example 13 and 126 mg (0.498 mmol) of 5-(4-bromophenyl)-1-methyl-1,2,3,6-tetrahydropyridine were used.
$^1$H-NMR (300 MHz, CDCl$_3$) δ: 1.47 (9H, s), 2.09 (3H, s), 2.36-2.45 (2H, m), 2.47 (3H, s), 2.59 (2H, t, J=5.4 Hz), 3.28 (2H, d, J=1.8 Hz), 5.35 (1H, d, J=5.7 Hz), 6.12-6.17 (1H, m), 7.28 (2H, d, J=8.7 Hz), 7.35 (2H, d, J=8.4 Hz).
MS (FAB) m/z: 706 (M++1).

Step (v) of Example 13

Methyl 6-N-((2S,4R)-4-cyclopropylmethyl)pipecoloyl-7-deoxy-7-epi-7-(4-(1-methyl-1,2,3,6-tetrahydropyridin-3-yl)phenylthio)-1-thio-α-lincosamide (compound 86)

The title compound (101 mg, yield 89%) was produced in the same manner as in step (ix) of Example 7, except that 127 mg (0.18 mmol) of the title compound produced in step (iv) of Example 13 was used.
For the title compound (86) produced in step (v) of Example 13 and compounds (72 to 85, 87 to 93, and 145) produced in the same manner as in step (v) of Example 13, $^1$H-NMR data and MS data are shown in Tables 5, 6, and 17.

Step (vi) of Example 13

Methyl 6-N-((2S,4R)-1-tert-butoxycarbonyl-4-cyclopropylmethyl)pipecoloyl-7-deoxy-7-epi-7-(4-(4-methylmorpholin-2-yl)phenylthio)-1-thio-α-lincosamide 2,6-Lutidine (0.011 ml, 0.093 mmol) was added to a solution of 15 mg (0.078 mmol) of the title compound, produced in step (v) of Reference Example 6, in methylene chloride (1 ml), and the mixture was stirred at 0° C. for 10 min. Trifluoromethanesulfonic anhydride (0.019 ml, 0.116 mmol) was added to the solution, and the mixture was stirred for 15 min. A saturated aqueous sodium hydrogencarbonate solution was added to the reaction solution to stop the reaction, and the mixture was then extracted with methylene chloride. The organic layer was washed with water and saturated brine and was then dried over anhydrous sodium sulfate. After filtration, the filtrate was concentrated under the reduced pressure, and the residue was dried. The title compound (42.5 mg, yield 81%) was produced in the same manner as in step (vi) of Example 1, except that a solution of the resultant crude product in dioxane (0.7 ml) and 39.4 mg (0.0931 mmol) of the title compound produced in step (iii) of Example 13 were used.

Step (vii) of Example 13

Methyl 6-N-((2S,4R)-4-cyclopropylmethyl)pipecoloyl-7-deoxy-7-epi-7-(4-(4-methylmorpholin-2-yl)phenylthio)-1-thio-α-lincosamide (compound 94)

The title compound (30.5 mg, yield 88%) was produced in the same manner as in step (ix) of Example 7, except that 40 mg (0.056 mmol) of the title compound produced in step (v) of Example 13 was used.

For the title compound (94) produced in step (v) of Example 13, $^1$H-NMR data and MS data are shown in Table 6.

Step (i) of Example 14

Methyl 6-N-((2S,4R)-1-tert-butoxycarbonyl-4-cyclopropylmethyl)pipecoloyl-7-deoxy-7-epi-7-(4-(1-methylpiperidin-3-yl)phenylthio)-1-thio-α-lincosamide The title compound (27.7 mg, (yield 14%) was produced in the same manner as in Example 6, except that 202 mg (0.289 mmol) of the title compound produced in step (iv) of Example 13 was used.

$^1$H-NMR (300 MHz, CD$_3$OD) δ: 1.45-1.55 (1H, m), 1.46 (9H, s), 1.66-2.18 (5H, m), 1.94 (3H, s), 2.37 (3H, s), 2.75-2.85 (1H, m), 2.94-3.03 (2H, m), 5.25 (1H, d, J=5.4 Hz), 7.20 (2H, d, J=8.1 Hz), 7.36 (2H, d, J=8.4 Hz).
MS (FAB) m/z: 708 (M$^+$+1).

Step (ii) of Example 14

Methyl 6-N-((2S,4R)-4-cyclopropylmethyl)pipecolyl-7-deoxy-7-epi-7-(4-(1-methylpiperidin-3-yl)phenylthio)-1-thio-α-lincosamide (compound 95)

The title compound (4.5 mg, yield 76%) was produced in the same manner as in step (ix) of Example 7, except that 6.9 mg (0.0098 mmol) of the title compound produced in step (i) of Example 14 was used.

For the title compound (95) produced in step (ii) of Example 14, $^1$H-NMR data and MS data are shown in Table 6.

Step (i) of Example 15

Methyl 6-N-((2S,4R)-4-cyclopropylmethyl-1-methyl)pipecoloyl-7-(4-(pyrimidin-5-yl)phenylthio)-7-deoxy-7-epi-1-thio-α-lincosamide (compound 100)

The title compound (56.9 mg, yield 94%) was produced in the same manner as in Example 4, except that 59.4 mg (0.10 mmol) of the compound (72) was used.

For the title compound (100) produced in step (i) of Example 15 and compounds (96 to 99, 101 to 120, and 146) produced in the same manner as in step (i) of Example 15, $^1$H-NMR data and MS data are shown in Tables 6, 7, and 17.

Step (ii) of Example 15

Methyl 6-N-((2S,4R)-4-cyclopropylmethyl-1-(2-hydroxy)ethyl)pipecoloyl-7-deoxy-7-epi-7-(4-(pyrimidin-5-yl)phenylthio)-1-thio-α-lincosamide Compound 121)

Diisopropylethylamine (34.0 μl, 0.2 mmol) and 2 ml (2.0 mmol) of a 1.0 M ethylene oxide/methylene chloride solution were added to a solution of 59.3 mg (0.1 mmol) of the compound (72) in methanol (1 ml), and the mixture was stirred at 0° C. overnight. The solvent was removed by distillation, and the residue was purified by preparative chromatography (chloroform:acetone:28% aqueous ammonia=10:1:0.1) to give 36.2 mg (yield 22%) of the title compound.

For the title compound (121) produced in step (ii) of Example 15, $^1$H-NMR data and MS data are shown in Table 7.

Step (iii) of Example 15

Methyl 6-N-((2S,4R)-1-cyclopropyl-4-cyclopropylmethyl)pipecoloyl-7-(4-(pyrimidin-5-yl)phenylthio)-7-deoxy-7-epi-1-thio-α-lincosamide (compound 122)

Acetic acid (0.03 mg, 0.5 mmol), 80 mg (0.5 mmol) of (1-methoxycyclopropyl)trimethylsilane, and 38 mg (0.5 mmol) of sodium cyanoborohydride were added to a solution of 59.3 mg (0.1 mmol) of the compound (72) in methanol (1 ml), and the mixture was stirred at 50° C. overnight. The solvent was removed by distillation, and the residue was purified by preparative chromatography (chloroform:acetone:28% aqueous ammonia=10:1:0.1) to give 35.4 mg (yield 33%) of the title compound.

For the title compound (122) produced in step (iii) of Example 15, $^1$H-NMR data and MS data are shown in Table 7.

Step (i) of Example 16

(S)-Methyl 2-(2-nitrophenylsulfonamide)pent-4-enoate

L-2-amino-4-pentenoic acid was added to a solution of 3.18 ml (43.5 mmol) of thionylchloride in methanol (40 ml), which had been cooled to 0° C., and the mixture was then stirred at room temperature for 24 hr. The reaction solution was concentrated under the reduced pressure, and the residue was dried. A solution of the crude product in diethyl ether (26 ml) was cooled to 0° C. A saturated aqueous sodium hydrogencarbonate solution (26 ml) was then added thereto. 2-Nitrobenzenesulfonyl chloride (4.24 g, 19.14 mol) was added, and the mixture was stirred at room temperature for 7 hr. Thereafter, the reaction solution was cooled to 0° C. N,N-Dimethylethylenediamine (2 ml) was added to the cooled solution, and the mixture was stirred at room temperature for 30 min. The organic layer was separated. The aqueous layer was then adjusted to pH 3 by the addition of citric acid and was then extracted with diethyl ether. The combined organic layers were washed with a 3% aqueous citric acid solution, a saturated aqueous sodium hydrogencarbonate solution, and saturated brine in that order, were dried over anhydrous sodium sulfate, and were then filtered. The filtrate was concentrated under the reduced pressure, and the residue was then purified by column chromatography on silica gel (hexane:ethyl acetate=5:1) to give 4.52 g (yield 83%) of the title compound.

$^1$H-NMR (400 MHz, CDCl$_3$) δ: 2.58 (2H, dd, J=5.9, 6.8 Hz), 3.52 (3H, s), 4.30 (1H, dt, J=5.8, 8.8 Hz), 5.12-5.15 (1H, m), 5.17 (1H, s), 5.62-5.72 (1H, m), 6.09 (1H, d, J=8.7 Hz), 7.72-7.76 (2H, m), 7.91-7.96 (1H, m), 8.06-8.10 (1H, m).

MS (FAB$^+$) m/z: 315 (M$^+$+1).

Step (ii) of Example 16

3-Methylenehexan-1-ol

Butyllithium (a 2.66 M toluene solution) (82 ml, 218.2 mmol) was added to a solution of 39 ml (258 mmol) of N,N,N',N'-tetramethylethylenediamine in diethyl ether (148 ml), which had been cooled to 0° C., and the mixture was then stirred at room temperature for one hr. The reaction solution was cooled to 0° C. 3-Methyl-3-buten-1-ol 10.1 ml (99.2 mmol) was added to the cooled solution, and the mixture was then stirred at room temperature for 6 hr. The reaction solution was cooled to −78° C. A solution of 8.9 ml (119 mmol) of bromoethane in diethyl ether (29.2 ml) was added to the cooled solution. The mixture was gradually raised to room temperature and was stirred for 15 hr. A saturated aqueous ammonium chloride solution was added thereto, and the mixture was extracted with dithyl ether. The organic layer was washed with a 3% aqueous citric acid solution, a saturated aqueous sodium hydrogencarbonate solution, and saturated brine in that order, was dried over anhydrous magnesium sulfate, and was then filtered. The filtrate was concentrated under the reduced pressure, and the residue was then purified by distillation under the reduced pressure to give 1.4 g (yield 12%) of the title compound.

$^1$H-NMR (400 MHz, CDCl$_3$) δ: 0.80 (3H, t, J=7.3 Hz), 1.35 (2H, tq, J=7.3. 7.5 Hz), 1.89 (2H, t, J=7.5 Hz), 2.17 (2H, t, J=6.3 Hz), 3.59 (2H, dt, J=5.3, 6.1 Hz), 4.70 (1H, dd, J=0.7, 1.2 Hz), 4.74 (1H, d, J=1.5 Hz).

MS (GC) m/z: 114 (M$^+$).

Step (iii) of Example 16

(S)-Methyl 2-(N-(3-methylenehexyl)-2-nitrophenylsulfonamide)pent-4-enoate

Tetrahydrofuran (30.2 ml) was added to 2.27 g (7.22 mmol) of the title compound in step (i) of Example 16 and 1.07 g (9.39 mmol) of the title compound in step (ii) of Example 16. The mixture was cooled to 0° C. Triphenylphosphine (2.84 g, 10.8 mmol) was added thereto, and the mixture was stirred for 10 min. Diisopropyl azodicarboxylate (2.1 ml, 10.8 mmol) was added thereto. The temperature of the mixture was then gradually raised over a period of 2 hr, and the mixture was stirred for 19 hr. The solvent was removed under the reduced pressure, and the residue was then purified by column chromatography on silica gel (hexane:ethyl acetate=20:1) to give 2.42 g (yield 82%) of the title compound.

$^1$H-NMR (400 MHz, CDCl$_3$) δ: 0.90 (3H, t, J=7.3 Hz), 1.45 (2H, tq, J=7.3. 7.6 Hz), 1.99 (2H, t, J=7.5 Hz), 2.32 (1H, dt, J=5.1, 12.9 Hz), 2.44-2.55 (2H, m), 2.83 (1H, dtt, J=1.5, 6.0, 15.1 Hz), 3.25 (1H, ddd, J=5.1, 12.2, 15.4 Hz), 3.53 (1H, ddd, J=5.1, 12.0, 15.3 Hz), 3.58 (3H, s), 4.71-4.75 (2H, m), 4.79 (1H, d, J=1.4 Hz), 5.14 (1H, dq, J=1.5, 10.2 Hz), 5.20 (1H, dq, J=1.5, 17.1 Hz), 5.82 (ddt, J=6.8, 10.5, 17.0 Hz), 7.56-7.60 (1H, m), 7.67-7.74 (2H, m), 8.02-8.06 (1H, m).

MS (FAB$^+$) m/z: 411 (M$^+$+1).

Step (iv) of Example 16

(S,Z)-Methyl 1-(2-nitrophenylsulfonyl)-5-propyl-2,3,6,7-tetrahydro-1H-azepine-2-carboxylate Benzylidene[1,3-bis(2,4,6-trimethylphenyl)-2-imidazolidinylidene]dichloro(tricyclohexylphosphine)ruthenium (250 mg, 0.295 mmol) was added to a solution of 2.42 g (5.89 mmol) of the title compound in step (iii) of Example 16 in methylene chloride (295 ml), and the mixture was heated under reflux for one hr. The reaction solution was cooled to room temperature. The solvent was removed under the reduced pressure, and the residue was purified by column chromatography on silica gel (hexane:ethyl acetate=10:1) to give 1.84 g (yield 82%) of the title compound.

$^1$H-NMR (400 MHz, CDCl$_3$) δ: 0.82 (3H, t, J=7.3 Hz), 1.22-1.42 (2H, m), 1.91 (3H, t, J=7.3 Hz), 2.28 (1H, ddd, J=1.9, 6.1, 16.3 Hz), 2.38-2.47 (1H, m), 2.56-2.64 (1H, m), 2.79 (1H, dt, J=7.3, 14.9 Hz), 3.45 (1H, ddd, J=2.2, 10.5, 14.4 Hz), 3.62 (3H, s), 3.83 (1H, ddd, J=3.2, 6.3, 14.4 Hz), 4.90 (1H, dd, J=3.4, 6.8 Hz), 5.45 (1H, ddd, J=1.0, 5.3, 7.3 Hz), 7.61-7.65 (1H, m), 7.66-7.71 (2H, m), 8.05-8.10 (1H, m).

MS (ESI$^+$) m/z: 383 (M$^+$+1).

Step (v) of Example 16

Methyl 6-N-((2S,Z)-1-(2-nitrophenylsulfonyl)-5-propyl-2-(2,3,6,7-tetra hydroazepine)carbonyl)-1-thio-α-lincosamide Lithium hydroxide monohydrate (164.6 mg, 3.92 mmol) was added to a solution of 500 mg (1.31 mmol) of the title compound produced in step (iv) of Example 16 in a solution (7 ml) of 1,4-dioxane:water=4:1, and the mixture was stirred at room temperature for 4 hr. The reaction solution was diluted by the addition of water and diethyl ether, and the diluted solution was filtered through Celite. The organic layer was separated, a 3% aqueous citric acid solution was added to the aqueous layer, and the mixture was extracted with ethyl acetate. The organic layers were combined, were dried over anhydrous sodium sulfate, and were filtered. The filtrate was concentrated under the reduced pressure and was dried. 1-Hydroxybenzotriazole 265.0 mg (1.96 mmol), 1-ethyl-3-(3-dimethylaminopropyl)carbodiimide hydrochloride 375.8 mg (1.96 mmol), N,N-dimethylformamide (5.0 ml) were added in that order to the crude product, and the mixture was stirred at room temperature for 20 min. Thereafter, 496.8 mg (1.96 mmol) of methyl 1-thio-α-lincosamide was added thereto, and the mixture was stirred at room temperature for 13 hr. A saturated aqueous sodium hydrogencarbonate solution was added thereto, and the mixture was then extracted with ethyl acetate. The extract was dried over anhydrous sodium sulfate and was then filtered. The filtrate was concentrated under the reduced pressure, and the residue was then purified by column chromatography on silica gel (chloroform:methanol=50:1) to give 660 mg (yield 84%) of the title compound.

$^1$H-NMR (400 MHz, CD$_3$OD) δ: 0.83 (3H, t, J=7.3 Hz), 1.15 (3H, d, J=6.3 Hz), 1.26-1.34 (2H, m), 1.80 (2H, t, J=7.3 Hz), 2.05 (3H, s), 2.25-2.55 (3H, m), 2.75 (1H, dt, J=7.5, 15.8 Hz), 3.58 (1H, dd, J=3.4, 10.2 Hz), 3.75-3.83 (3H, m), 4.03-4.11 (3H, m), 4.38 (1H, d, J=5.8 Hz), 5.22 (1H, d, J=5.6 Hz), 5.37-5.42 (1H, m), 7.74-7.78 (1H, m), 7.79-7.86 (2H, m), 8.09-8.14 (1H, m).

MS (FAB$^+$) m/z: 604 (M$^+$+1).

Step (vi) of Example 16

Methyl 6-N-((2S,5S)-5-propyl-2-azepanecarbonyl)-1-thio-α-lincosamide

4-Bromobenzenethiol (413.4 mg, 2.19 mmol) was added to a solution of 660 mg (1.09 mmol) of the title compound produced in step (v) of Example 16 in N,N-dimethylformamide (5 ml), and the mixture was cooled to 0° C. 1,3,4,6,7,8-Hexahydro-1-methyl-2H-pyrimido[1,2-a]pyrimidine was added to this solution, and the mixture was stirred for 6 hr. The solvent was removed under the reduced pressure, and the residue was purified by column chromatography (hexane:ethyl acetate=1:1, chloroform:methanol=10:1). Raney nickel (1 g) was added to a solution of 475 mg of the crude product in methanol (5 ml), and the mixture was stirred in a hydrogen atmosphere for 37 hr. The reaction solution was filtered through Celite, and the filtrate was removed under the reduced pressure. The residue was purified by column chromatography on silica gel (chloroform:methanol:28% aqueous ammonia=20:1:0.1) to give 130 mg (yield 28%) of the title compound.

$^1$H-NMR (400 MHz, CD$_3$OD) δ: 0.90 (3H, t, J=7.3 Hz), 1.18 (3H, d, J=6.6 Hz), 1.19-1.42 (7H, m), 1.61-1.71 (1H, m), 1.80-1.86 (1H, m), 1.95-2.03 (2H, m), 2.08 (3H, s), 2.74-2.82 (1H, m), 3.03 (1H, ddd, J=2.4, 5.6, 14.2 Hz), 3.57 (1H, dd, J=3.4, 10.2 Hz), 3.59 (1H, t, J=5.6 Hz), 3.96 (1H, d, J=2.7 Hz), 4.06 (1H, q, J=6.4 Hz), 4.10 (1H, dd, J=5.6, 10.2 Hz), 4.18 (1H, dd, J=6.3, 7.8 Hz), 4.24 (1H, d, J=7.8 Hz), 5.24 (1H, d, J=5.4 Hz).

MS (FAB$^+$) m/z: 421 (M$^+$+1).

Step (vii) of Example 16

Methyl 7-acetylthio-7-deoxy-7-epi-6-N-((2S,5S)-1-tert-butoxycarbonyl-5-propyl-2-azepanecarbonyl)-2,3,4-tri-o-trimethylsilyl-1-thio-α-lincosamide Lithium hydroxide monohydrate (16.5 mg, 0.393 mmol) was added to a solution (5.5 ml) of 110 mg (0.262 mmol) of the title compound produced in step (vi) of Example 16 in 1,4-dioxane:water=4:1. The mixture was stirred at room temperature for 5 min. Tert-butyl dicarbonate was then added to the reaction solution, and the mixture was stirred at room temperature for one hr. A saturated aqueous sodium hydrogencarbonate solution was added thereto, and the mixture was extracted with ethyl acetate. The extract was dried over anhydrous sodium sulfate and was filtered. The filtrate was concentrated under the reduced pressure, and the concentrate was dried to give methyl 6-N-((2S,5S)-1-tert-butoxycarbonyl-5-propyl-2-azepanecarbonyl)-1-thio-α-lincosamide as a crude product. Methyl 6-N-((2S,5S)-1-tert-butoxycarbonyl-5-propyl-2-azepanecarbonyl)-2,3,4-tri-o-trimethylsilyl-1-thio-α-lincosamide was produced in the same manner as in step (i) of Example 1, except that the crude product and, further, 0.166 ml (1.31 mmol) of trimethylsilyl chloride, 0.275 mol (1.31 mmol) of hexamethyldisilazane, pyridine (5.5 ml), methanol (5.5 ml), and 0.171 ml (0.341 mmol) of a 2 N aqueous acetic acid solution were used. Methyl 6-N-((2S,5S)-1-tert-butoxycarbonyl-5-propyl-2-azepanecarbonyl)-7-o-methylsulfonyl-2,3,4-tri-o-trimethylsilyl-1-thio-α-lincosamide was produced in the same manner as in step (i) of Example 2, except that the crude product and, further, 0.182 ml (1.31 mmol) of triethylamine, 0.082 ml (1.05 mmol) of methanesulfonyl chloride, and chloroform (3.0 ml) were used. The title compound (96 mg, 46%) was produced in the same manner as in step (iii) of Example 1, except that the crude product and, further, 181.3 mg (1.59 mmol) of potassium thioacetate, and N,N-dimethylformamide (1.5 ml) were used.

$^1$H-NMR (400 MHz, CDCl$_3$) δ: −0.0043 (9H, s), 0.00 (9H, s), 0.042 (9H, s), 0.76 (3H, t, J=6.9 Hz), 1.06-1.23 (9H, m), 1.35-1.38 (1H, m), 1.38 (9H, s), 1.50-1.80 (4H, m), 1.85 (3H, s), 2.16 (3H, s), 2.70-2.95 (1H, m), 3.35-3.45 (2H, m), 3.58-4.20 (4H, m), 4.25-4.50 (2H, m), 5.02 (1H, d, J=5.6 Hz), 6.16 (1H, brd).

MS (FAB$^+$) m/z: 795 (M$^+$+1).

Step (viii) of Example 16

Methyl 6-N-((2S,5S)-1-tert-butoxycarbonyl-5-propyl-2-azepanecarbonyl)-7-deoxy-7-epi-7-mercapto-1-thio-α-lincosamide 1 N hydrochloric acid (0.424 ml, 0.424 mmol) was added to a solution of 96 mg (0.121 mmol) of the title compound produced in step (vii) of Example 16 in methanol (2.0 ml), and the mixture was stirred at room temperature for 40 min. The reaction solution was concentrated under the reduced pressure, and the concentrate was then dried. A solution (0.03 ml) of 4.1 N sodium methoxide in methanol was added to a solution of the crude product in methanol (2 ml), and the mixture was stirred at room temperature for 30 min. A saturated aqueous sodium hydrogencarbonate solution was added to the reaction solution, and the mixture was extracted with ethyl acetate. The extract was dried over anhydrous sodium sulfate and was then filtered. The filtrate was concentrated under the reduced pressure, and the residue was purified by column chromatography on silica gel (chloroform:methanol:28% aqueous ammonia=20:1:0.1) to give 40 mg (yield 62%) of the title compound.

$^1$H-NMR (400 MHz, CD$_3$OD) δ: 0.91 (3H, t, J=6.8 Hz), 1.24-1.35 (8H, m), 1.45-1.50 (1H, m), 1.48 (9H, s), 1.60-1.75 (3H, m), 1.90-2.05 (2H, m), 2.15 (3H, s), 3.45-3.59 (3H, m), 3.80-3.90 (1H, m), 4.02-4.15 (2H, m), 4.24-4.34 (1H, m), 4.36-4.32 (2H, m), 5.24 (1H, d, J=5.6 Hz).

MS (ESI$^+$) m/z: 537 (M$^+$+1).

Step (ix) of Example 16

Methyl 6-N-((2S,5S)-1-tert-butoxycarbonyl-5-propyl-2-azepanecarbonyl)-7-deoxy-7-epi-7-(4-(pyrimidin-5-yl)phenylthio)-1-thio-α-lincosamide The title compound (101 mg, yield 77%) was produced in the same manner as in step (vi) of Example 1, except that 100 mg (0.19 mmol) of the title compound produced in step (viii) of Example 16 and 66.0 mg (0.289 mmol) of 5-(4-bromophenyl)pyrimidine were used.

Step (x) of Example 16

Methyl 6-N-((2S,5S)-5-propyl-2-azepanecarbonyl)-7-deoxy-7-epi-7-(4-(pyrimidin-5-yl)phenylthio)-1-thio-α-lincosamide The title compound (78.2 mg, yield 91%) was produced in the same manner as in step (ix) of Example 7, except that 100 mg (0.15 mmol) of the title compound produced in step (v) of Example 10 was used.

For the title compound (123) produced in step (x) of Example 16, $^1$H-NMR data and MS data are shown in Table 7.

Example 17

Methyl 6-N-((2S,5S)-1-methyl-5-propyl-2-azepanecarbonyl)-7-deoxy-7-epi-7-(4-(pyrimidin-5-yl)phenylthio)-1-thio-α-lincosamide (compound 124)

The title compound (34.3 mg, yield 84%) was produced in the same manner as in Example 4, except that 40.0 mg (0.069 mmol) of the title compound produced in step (x) of Example 16 was used.

For the title compound (124) of Example 17, $^1$H-NMR data and MS data are shown in Table 7.

Step (i) of Example 18

Methyl 6-N-((2S,4R)-1-acetamidemethyl-4-cyclopropylmethyl)pipecoloyl-7-deoxy-7-epi-7-(4-(pyrimidin-5-yl)phenylthio)-1-thio-α-lincosamide (compound 125)

Benzamide (145 mg, 1.20 mmol) and 40 µl of formalin were added to a solution of 50 mg (80.0 µmol) of the compound (72) monohydrochloride in methanol (0.5 ml), and the mixture was stirred at room temperature for 3 days. Further, 145 mg (1.20 mmol) of benzamide and 40 µl of formalin were added thereto, and the mixture was stirred at 50° C. for 4 days. The reaction solution was then diluted with ethyl acetate. The diluted solution was washed with a 10% aqueous sodium hydrogencarbonate solution and was then dried over anhydrous sodium sulfate. After filtraiton, the filtrate was concentrated. The residue was purified by column chromatography on silica gel (chloroform:methanol=100:0 to 90:10) to give 35 mg (yield 61%) of the title compound.

For the title compound (125) produced in step (i) of Example 18, $^1$H-NMR data and MS data are shown in Table 7.

Step (ii) of Example 18

Methyl 6-N-((2S,4R)-4-cyclopropylmethyl-1-ethoxycarbonyl)pipecoloyl-7-deoxy-7-epi-7-(4-(pyrimidin-5-yl)phenylthio)-1-thio-α-lincosamide (compound 126)

A 1 N aqueous sodium hydroxide solution (136 µl) and 8.9 µl of ethylchloroformate were added to a solution of 40 mg (68 µmol) of the compound (72) in dioxane (0.4 ml), and the mixture was stirred at room temperature for one hr. Further, 68 µl of a 1 N aqueous sodium hydroxide solution and 4.4 µl of ethylchloroformate were added to the reaction solution, and the mixture was stirred at room temperature for 30 min. The reaction solution was diluted with ethyl acetate. The diluted solution was washed with a 10% aqueous sodium hydrogencarbonate solution followed by drying over anhydrous sodium sulfate. After filtration, the filtrate was concentrated, and the residue was purified by column chromatography on silica gel (chloroform:methanol=100:0→96:4) to give 31 mg (yield 69%) of the title compound.

For the title compound (126) produced in step (ii) of Example 18 and the compound (127) produced in the same manner as in step (ii) of Example 18, $^1$H-NMR data and MS data are shown in Table 7.

Step (iii) of Example 18

Methyl 6-N-((2S,4R)-4-cyclopropylmethyl-1-((5-methyl-2-oxo-1,3-diox ol-4-yl)methoxy)carbonyl)pipecoloyl-7-deoxy-7-epi-7-(4-(pyrimidin-5-yl)phenylthio)-1-thio-α-lincosamide (compound 128)

Diisopropylethylamine (18 µl, 102 µmol) and 22 mg (75 µmol) of (5-methyl-2-oxo-1,3-dioxol-4-en-4-yl)methyl p-nitrophenylcarbonate produced as described in J. Med. Chem., 1996, 39, 480 were added to a solution of 40 mg (68 µmol) of the compound (72) in N,N-dimethylformamide (0.5 ml), and the mixture was stirred at room temperature for 6 hr. The reaction solution was diluted with ethyl acetate, and the diluted solution was then washed with a 10% aqueous sodium chloride solution followed by drying over anhydrous sodium sulfate. After filtration, the filtrate was concentrated. The residue was purified by column chromatography on silica gel (ethyl acetate:acetone=100:0→80:20) to give 37 mg (yield 73%) of the title compound.

For the title compound (128) produced in step (iii) of Example 18, $^1$H-NMR data and MS data are shown in Table 7.

Step (iv) of Example 18

Methyl 6-N-((2S,4R)-4-cyclopropylmethyl-1-((5-methyl-2-oxo-1,3-dioxol-4-yl)methyl)pipecoloyl-7-deoxy-7-epi-7-(4-(pyrimidin-5-ylphenylthio)-1-thio-α-lincosamide (compound 129)

Sodium carbonate (5.9 mg, 56 µmol) and 13 mg (56 µmol) of 4-chloromethyl-5-methyl-2-oxo-1,3-dioxolene produced as described in Chem. Pharm. Bull., 32, 2241 (1984) were added to a solution of 30 mg (51 µmol) of the compound (72) in N,N-dimethylformamide (0.5 ml), and the mixture was stirred at room temperature for 1.5 hr.

The reaction solution was diluted with ethyl acetate. The diluted solution was washed with a 10% aqueous sodium chloride solution followed by drying over anhydrous sodium sulfate. After filtration, the filtrate concentrated, and the residue was purified by column chromatography on silica gel (ethyl acetate:acetone=100:0→80:20) to give 37 mg (yield 100%) of the title compound.

For the title compound (129) produced in step (iv) of Example 18, $^1$H-NMR data and MS data are shown in Table 7.

Step (v) of Example 18

Methyl 6-N-((2S,4R)-4-cyclopropylmethyl-1-((chloromethoxy)carbonyl))pipecoloyl-7-deoxy-7-epi-7-(4-(pyrimidin-5-yl)phenylthio)-1-thio-α-lincosamide A 1 N aqueous sodium hydroxide solution (255 µl), 250 µl of water, and 18 µl of chloromethyl chloroformate were added to a solution of 100 mg (170 µmol) of the compound (72) in dioxane (0.6 ml), and the mixture was stirred at room temperature for 4 hr. The reaction solution was diluted with ethyl acetate, and the diluted solution was washed with a 10% aqueous sodium hydrogencarbonate solution and was then dried over anhydrous sodium sulfate. After filtration, the filtrate was concentrated, and the residue was purified by column chromatography on silica gel (chloroform:methanol=100:0→97:3) to give 58 mg (yield 50%) of the title compound.

MS (EI) m/z 681 (M+1)$^+$.

Step (vi) of Example 18

Methyl 6-N-((2S,4R)-1-((acetoxymethoxy)carbonyl)-4-cyclopropylmethyl)pipecoloyl-7-deoxy-7-epi-7-(4-(pyrimidin-5-yl)phenylthio)-1-thio-α-lincosamide (compound 131)

Potassium acetate (8.4 mg, 85 μmol) was added to a solution of the title compound (29 mg, 43 μmol) produced in step (iv) of Example 18 in N,N-dimethylformamide (0.3 ml), and the mixture was stirred at room temperature for 2 hr 20 min. The reaction solution was diluted with ethyl acetate, and the diluted solution was washed with a 10% aqueous sodium chloride solution, following by drying over anhydrous sodium sulfate. After filtration, the filtrate was concentrated, and the residue was purified by preparative TLC (ethyl acetate:methanol=7:1) to give 16 mg (yield 53%) of the title compound.

For the title compound (131) produced in step (vi) of Example 18 and the compound (132) produced in the same manner as in step (vi) of Example 18, $^1$H-NMR data and MS data are shown in Table 8.

Step (vii) of Example 18

Methyl 6-N-((2S,4R)-4-cyclopropylmethyl-1-formyl)pipecoloyl-7-deoxy-7-epi-7-(4-(pyrimidin-5-yl)phenylthio)-1-thio-α-lincosamide (compound 130)

A mixed solvent composed of 20 μl of acetic anhydride and 40 μl of formic acid was heated at 60° C. for one hr. A solution of 20 mg (34 μmol) of the compound (72) in methanol (0.2 ml) was added thereto, and the mixture was stirred at 60° C. for 16 hr. The reaction solution was concentrated, and the residue was purified by preparative chromatography (chloroform:acetone:28% aqueous ammonia=10:1:0.1) to give 19.2 mg (yield 22%) of the title compound.

For the title compound (130) produced in step (vii) of Example 18, $^1$H-NMR data and MS data are shown in Table 7.

Step (i) of Example 19

Methyl 6-N-((2S,4R)-1-tert-butoxycarbonyl-4-cyclopropylmethyl)pipecoloyl-7-deoxy-2,3-o-diacetyl-7-epi-7-(4-(pyrimidin-5-yl)phenylthio)-1-thio-α-lincosamide Acetic anhydride (0.123 ml, 1.31 mmol) was added to a solution of methyl 6-N-((2S,4R)-1-tert-butoxycarbonyl-4-cyclopropylmethyl)pipecoloyl-7-deoxy-7-epi-7-(4-(pyrimidin-5-yl)phenylthio)-1-thio-α-lincosamide 300 mg (0.435 mmol) produced as described in step (iv) of Example 13 in pyridine (2.4 ml), and the mixture was stirred at room temperature for 18 hr. The reaction solution was concentrated, and the residue was purified by column chromatography on silica gel (hexane:ethyl acetate=70:30→30:70) to give 244 mg (yield 73%) of the title compound.

MS (FAB) m/z 773 (M+1)$^+$.

Step (ii) of Example 19

Methyl 6-N-((2S,4R)-4-cyclopropylmethyl)pipecoloyl-7-deoxy-2,3-o-diacetyl-7-epi-7-(4-(pyrimidin-5-yl)phenylthio)-1-thio-α-lincosamide monohydrochloride (compound 133)

The title compound (38 mg, yield 91%) was produced in the same manner as in step (ix) of Example 7, except that 46 mg (0.059 mmol) of the title compound produced in step (i) of Example 19 was used.

For the title compound (133) produced in step (ii) of Example 19, $^1$H-NMR data and MS data are shown in Table 8.

Step (iii) of Example 19

Methyl 6-N-((2S,4R)-1-tert-butoxycarbonyl-4-cyclopropylmethyl)pipecoloyl-7-deoxy-7-epi-2,3-o-(propan-2,2-diyl)-7-(4-(pyrimidin-5-yl)phenylthio)-1-thio-α-lincosamide 2,2-Dimethoxypropane (190 μl, 2.95 mmol) and 254 mg (1.7 mmol) of tosylic acid were added to a solution of 300 mg (0.435 mmol) of methyl 6-N-((2S,4R)-1-tert-butoxycarbonyl-4-cyclopropylmethyl)pipecoloyl-7-deoxy-7-epi-7-(4-(pyrimidin-5-yl)phenylthio)-1-thio-α-lincosamide produced in the same manner as in step (iv) of Example 13 in N,N-dimethylformamide (5 ml), and the mixture was stirred at room temperature for 18 hr. The reaction solution was diluted with ethyl acetate. The diluted solution was washed with a 10% aqueous sodium hydrogencarbonate solution and a 10% aqueous sodium chloride solution. The washed solution was then dried over anhydrous sodium sulfate. After filtration, the filtrate was concentrated. The residue was purified by column chromatography on silica gel (chloroform:methanol=100:0→98.5:1.5) to give 302 mg (yield 92%) of the title compound.

Step (iv) of Example 19

Methyl 2-o-acetyl-6-N-((2S,4R)-4-cyclopropylmethyl)pipecoloyl-7-deoxy-7-epi-7-(4-(pyrimidin-5-yl)phenylthio)-1-thio-α-lincosamide (compound 134)

Acetic anhydride (88 μl, 993 μmol) and a catalytic amount of N,N-dimethylaminopyridine were added to a solution of 250 mg (343 μmol) of the title compound produced in step (iii) of Example 19 in pyridine (2 ml), and the mixture was stirred at room temperature for 30 min.

The reaction solution was diluted with ethyl acetate, and the diluted solution was washed with a 10% aqueous sodium hydrogencarbonate solution and a 10% aqueous sodium chloride solution. The washed solution was then dried over anhydrous sodium sulfate. After filtration, the filtrate was concentrated. Trifluoroacetic acid (1.5 ml) was added to a solution of the residue in dichloromethane (3 ml) under ice cooling, and the mixture was stirred at room temperature for 30 min. The reaction solution was diluted with ethyl acetate. The diluted solution was washed with a 10% aqueous sodium hydrogencarbonate solution and a 10% aqueous sodium chloride solution. The washed solution was then dried over anhydrous sodium sulfate. After filtration, the filtrate was concentrated, and the residue was purified by column chromatography on silica gel (chloroform:methanol=100:0 to 98:2) to give 185 mg (yield 86%) of the title compound.

For the title compound (134) produced in step (iv) of Example 19, $^1$H-NMR data and MS data are shown in Table 8.

Step (i) of Example 20

Methyl 6-N-((2S,4R)-4-cyclopropylmethyl-1-methyl)pipecoloyl-7-deoxy-2,3-o-diacetyl-7-epi-7-(4-(pyrimidin-5-yl)phenylthio)-1-thio-α-lincosamide (compound 138)

Acetic anhydride (113 μl, 1.19 mmol) was added to a solution of 180 mg (299 μmol) of the compound (100) in pyridine (1.5 ml), and the mixture was stirred at room temperature for 18 hr. The reaction solution was diluted with ethyl acetate. The diluted solution was washed with a 10% aqueous sodium chloride solution. The washed solution was then dried over anhydrous sodium sulfate. After filtration, the filtrate was concentrated, and the residue was purified by column chromatography on silica gel (chloroform:methanol=100:0 to 98.5:1.5) to give 166 mg (yield 78%) of the title compound.

For the title compound (138) produced in step (i) of Example 20 and the compound (141) produced in the same manner as in step (i) of Example 20, $^1$H-NMR data and MS data are shown in Table 8.

Step (ii) of Example 20

Methyl 6-N-((2S,4R)-4-cyclopropylmethyl-1-methyl)pipecoloyl-7-deoxy-7-epi-2,3-o-(propan-2,2-diyl)-7-(4-(pyrimidin-5-yl)phenylthio)-1-thio-α-lincosamide The title compound (520 mg, yield 82%) was produced in the same manner as in step (ii) of Example 19, except that 592 mg (982 μmol) of the compound (100) was used.

Step (iii) of Example 20

Methyl 2-o-acetyl-6-N-((2S,4R)-4-cyclopropylmethyl-1-methyl)pipecoloyl-7-deoxy-7-epi-7-(4-(pyrimidin-5-yl)phenylthio)-1-thio-α-lincosamide (compound 139)

The title compound (177 mg, yield 88%) was produced in the same manner as in step (ii) of Example 19, except that 200 mg (311 μmol) of the title compound produced in step (ii) of Example 20 was used.

For the title compound (139) produced in step (iii) of Example 20 and the compounds (137 and 142 to 144) produced in the same manner as in step (iii) of Example 20, $^1$H-NMR data and MS data are shown in Table 8.

Step (iv) of Example 20

Methyl 6-N-((2S,4R)-4-cyclopropylmethyl-1-methyl)pipecoloyl-7-deoxy-2,3,4-o-triacetyl-7-epi-7-(4-(pyrimidin-5-yl)phenylthio)-1-thio-α-lincosamide (compound 140)

Acetic anhydride (113 μl, 1.19 μmol) and a catalytic amount of N,N-dimethylaminopyridine were added to a solution of 180 mg (299 μmol) of the compound (100) in pyridine (0.5 ml), and the mixture was stirred at room temperature for 15 hr. The reaction solution was diluted with ethyl acetate. The diluted solution was washed with a 10% aqueous sodium hydrogencarbonate solution and a 10% aqueous sodium chloride solution. The washed solution was then dried over anhydrous sodium sulfate. After filtration, the filtrate was concentrated, and the residue was purified by column chromatography on silica gel (hexane:ethyl acetate=50:50 to 0:100) to give 37 mg (yield 89%) of title compound.

For the title compound (140) produced in step (iv) of Example 20, $^1$H-NMR data and MS data are shown in Table 8.

Step (i) of Example 21

Methyl 6-N-((2S,4R)-4-cyclopropylmethyl-1-((5-methyl-2-oxo-1,3-dioxol-4-yl)methoxy)carbonyl)pipecoloyl-7-deoxy-2,3-o-diacetyl-7-epi-7-(4-(pyrimidin-5-yl)phenylthio)-1-thio-α-lincosamide (compound 135)

The title compound (15 mg, yield 28%) was produced in the same manner as in step (iii) of Example 18, except that 50 mg (65 μmol) of the compound (133) was used.

For the title compound (135) produced in step (i) of Example 21, $^1$H-NMR data and MS data are shown in Table 8.

Step (ii) of Example 21

Methyl 2-acetyl-6-N-((2S,4R)-4-cyclopropylmethyl-1-((5-methyl-2-oxo-1,3-dioxol-4-yl)methoxy)carbonyl)pipecoloyl-7-deoxy-7-epi-7-(4-(pyrimidin-5-yl)phenylthio)-1-thio-α-lincosamide (compound 136)

The title compound (9 mg, yield 51%) was produced in the same manner as in step (iii) of Example 18, except that 15 mg (23 μmol) of the compound (134) was used.

For the title compound (136) produced in step (ii) of Example 21, $^1$H-NMR data and MS data are shown in Table 8.

Specific examples of compounds according to the present invention include compounds shown in Tables 9 to 16 below.

Test Example 1

Antimicrobial Activity

For representative compounds among lincomycin derivatives according to the present invention, the minimum growth inhibitory concentration (MIC, μg/ml) against various pneumococci was measured according to the method described in CHEMOTHERAPY, vol. 16, No. 1, 99, 1968. The results are shown in Table 1. Sensitivity disk agar-N+5% horse blood was used as the medium for the measurement. The amount of bacteria inoculated was about $10^6$ CFU/ml. In Table 1, CLDM represents clindamycin.

TABLE 1

| | Example No. | | | | | | |
|---|---|---|---|---|---|---|---|
| | 3 | 17 | 59 | 65 | 93 | 120 | CLDM |
| S. pneumoniae DP1 TypeI | 0.015 | 0.03 | ≦0.008 | 0.015 | 0.06 | 0.13 | 0.13 |
| S. pneumoniae IP692 | 0.03 | 0.03 | ≦0.008 | 0.015 | 0.13 | 0.13 | 0.13 |
| S. pneumoniae 1913 | ≦0.008 | 0.03 | 0.015 | 0.015 | 0.13 | 0.25 | 0.13 |
| S. pneumoniae 1820 | 2 | 4 | 0.25 | 2 | 1 | 4 | 256 |
| S. pneumoniae 1700 | 2 | 2 | 0.13 | 2 | 0.5 | 2 | 256 |
| S. pneumoniae PRC-206 | 2 | 4 | 0.25 | 2 | 1 | 4 | 256 |
| S. pneumoniae 225 | 8 | 32 | 1 | 4 | 1 | 8 | 256 |
| S. pneumoniae TH-662 | 0.25 | 2 | 0.13 | 0.5 | 0.5 | 1 | 256 |
| S. pneumoniae PRC-53 | ≦0.008 | 0.015 | ≦0.008 | ≦0.008 | 0.06 | 0.13 | 0.03 |

As can be seen from the results, the lincomycin derivatives of formula (I) according to the present invention demonstrated potent antimicrobial activity against macrolide resistant pneumococci.

TABLE 2

| Compound No. | Compound name | NMR data δ (ppm) from TMS | Solvent/Hz | MS (FAB$^+$) |
|---|---|---|---|---|
| 1 | 7-Deoxy-7-epi-7-(4-(pyrimidin-5-yl)phenylthio)lincomycin | 1.96 (3H, s), 2.43 (3H, s), 5.27 (1H, d, J = 5.4 Hz), 7.57 (2H, d, J = 8.7 Hz), 7.71 (2H, d, J = 8.4 Hz), 9.07 (2H, s), 9.13 (1H, s). | CD$_3$OD (300 MHz) | 577 (M$^+$ + 1) |
| 2 | 7-Deoxy-7-(3,5-difluoro-4-(pyrimidin-5-yl)phenylthio)-7-epilincomycin | 1.96 (3H, s), 2.41 (3H, s), 3.79 (3H, s), 5.27 (1H, d, J = 5.6 Hz), 7.22 (2H, d, J = 8.8 Hz), 8.92 (2H, dd, J = 1.2, 1.2 Hz), 9.18 (1H, s) | CD$_3$OD (400 MHz) | 613 (M$^+$ + 1) |
| 3 | 7-Deoxy-7-epi-7-(3-fluoro-4-(pyrimidin-5-yl)phenylthio)lincomycin | 1.95 (3H, s), 2.41 (3H, s), 5.27 (1H, d, J = 5.6 Hz), 7.34-7.38 (2H, m), 7.58-7.62 (1H, t, J = 8.2 Hz), 8.99 (2H, d, J = 1.4 Hz), 9.15 (1H, s) | CD$_3$OD (400 MHz) | 595 (M$^+$ + 1) |
| 4 | 7-Deoxy-7-epi-7-(2-fluoro-4-(pyrimidin-5-yl)phenylthio)lincomycin | 2.01 (3H, s), 2.42 (3H, s), 5.26 (1H, d, J = 5.6 Hz), 7.57-7.68 (3H, m), 9.09 (2H, s), 9.15 (1H, s) | CD$_3$OD (400 MHz) | 595 (M$^+$ + 1) |
| 5 | 7-(2-Cyano-4-pyrimidin-5-yl)phenylthio)-7-deoxy-7-epilincomycin | 1.95 (3H, s), 2.57 (3H, s), 5.26 (1H, d, J = 5.4 Hz), 7.80 (1H, d, J = 8.3 Hz), 7.89 (1H, dd, J = 8.3, 2.0 Hz), 8.17 (1H, d, J = 2.0 Hz), 9.12 (2H, s), 9.18 (1H, s) | CD$_3$OD (400 MHz) | 602 (M$^+$ + 1) |
| 6 | 7-(3-Cyano-4-(pyrimidin-5-yl)phenylthio)-7-deoxy-7-epilincomycin | 1.96 (3H, s), 2.42 (3H, s), 5.26 (1H, d, J = 5.6 Hz), 7.65 (1H, d, J = 8.3 Hz), 7.83 (1H, dd, J = 8.3, 2.0 Hz), 7.94 (1H, d, J = 2.0 Hz), 9.04 (2H, s), 9.25 (1H, s) | CD$_3$OD (400 MHz) | 602 (M$^+$ + 1) |
| 7 | 7-Deoxy-7-(2,5-dimethox-4-(pyrimidin-5-yl)phenylthio)-7-epilincomycin | 1.95 (3H, s), 2.41 (3H, s), 3.83 (3H, s), 3.90 (3H, s), 5.23 (1H, d, J = 5.6 Hz), 7.09 (1H, s), 7.21 (1H, s), 8.97 (2H, s), 9.08 (1H, s) | CD$_3$OD (400 MHz) | 637 (M$^+$ + 1) |
| 8 | 7-Deoxy-7-epi-7-(4-(pyrimidin-2-yl)phenylthio)lincomycin | 1.93 (3H, s), 2.39 (3H, s), 5.29 (1H, d, J = 5.7 Hz), 7.33 (1H, t, J = 4.8 Hz), 7.51 (2H, d, J = 8.4 Hz), 8.35 (2H, d, J = 8.4 Hz), 8.82 (2H, d, J = 4.8 Hz). | CD$_3$O (300 MHz) | 577 (M$^+$ + 1) |
| 9 | 7-Deoxy-7-epi-7-(4-(2-nitrophenylthio)-phenylthio)-lincomycin | 1.93 (3H, s), 2.42 (3H, s), 5.27 (1H, d, J = 5.6 Hz), 6.90 (1H, d, J = 7.3 Hz), 7.30 (1H, dd, J = 7.3, 7.3 Hz), 7.41-7.50 (5H, m), 8.18 (1H, d, J = 8.2 Hz) | CD$_3$OD (400 MHz) | 651 EI (M$^+$) |
| 10 | 7-Deoxy-7-epi-7-(4-(methoxy(pyridin-2-yl)methyl)phenylthio)-lincomycin | 1.83 (3H, d, J = 3.0 Hz), 2.35 (3H, s), 3.38 (3H, s), 5.23 (1H, d, J = 5.7 Hz), 5.34 (1H, s), 7.26-7.31 (1H, m), 7.35 (2H, d, J = 9.3 Hz), | CD$_3$OD (300 MHz) | 620 (M$^+$ + 1) |

TABLE 2-continued

| Compound No. | Compound name | NMR data δ (ppm) from TMS | Solvent/Hz | MS (FAB+) |
|---|---|---|---|---|
| 11 | 7-Deoxy-7-epi-7-(4-(hydroxy(pyridin-3-yl)methyl)phenylthio)-lincomycin | 7.39 (2H, d, J = 9.9 Hz), 7.57 (1H, d, J = 7.8 Hz), 7.82 (1H, dt, J = 1.5, 7.8 Hz), 8.45 (1H, ddd, J = 0.6, 0.9) 1.89 (3H, s), 2.38 (3H, s), 5.24 (1H, d, J = 5.4 Hz), 5.84 (1H, s), 7.32-7.42 (5H, m), 7.82 (1H, ddd, J = 1.8, 2.1, 8.1 Hz), 8.40 (1H, dd, J = 1.8, 5.1 Hz), 8.55 (1H, d, J = 2.1 Hz). | $CD_3OD$ (300 MHz) | 606 ($M^+$ + 1) |
| 12 | 7-Deoxy-7-epi-7-(4-(methoxy(pyridin-4-yl)methyl)phenylthio)-lincomycin | 1.84 (3H, s), 2.38 (3H, s), 3.36 (3H, s), 5.22 (1H, d, J = 6.0 Hz), 5.33 (1H, s), 7.33 (2H, d, J = 8.1 Hz), 7.41 (2H, d, J = 8.4 Hz), 7.43 (2H, d, J = 4.5 Hz), 7.85 (2H, dd, J = 1.5, 4.5 Hz). | $CD_3OD$ (300 MHz) | 620 ($M^+$ + 1) |
| 13 | 7-Deoxy-7-epi-7-(4-(methoxy(pyridin-3-yl)methyl)phenylthio)-lincomycin | 1.85 (3H, s), 2.37 (3H, s), 3.36 (3H, s), 5.23 (1H, d, J = 5.4 Hz), 5.38 (1H, s), 7.29-7.44 (5H, m), 7.80 (1H, ddd, J = 1.8, 1.8, 7.8 Hz), 8.42 (1H, dd, J = 1.8, 5.1 Hz), 8.52 (1H, d, J = 2.1 Hz). | $CD_3OD$ (300 MHz) | 620 ($M^+$ + 1) |
| 14 | 7-(5-Amino-1,3,4-thiadiazol-2-yl)phenylthio)-7-deoxy-7-epilincomycin | 2.04 (3H, s), 2.39 (3H, s), 5.36 (1H, d, J = 5.4 Hz), 7.44 (2H, d, J = 8.4 Hz), 7.72 (2H, d, J = 8.4 Hz) | $CDCl_3$ (300 MHz) | 598 ($M^+$ + 1) |
| 15 | 7-(4-(2-Aminothiazol-4-yl)phenylthio)-7-deoxy-7-epilincomycin | 2.09 (3H, s), 2.35 (3H, s), 5.35 (1H, d, J = 5.4 Hz), 6.70 (1H, s), 7.42 (2H, d, J = 7.8 Hz), 7.70 (2H, d, J = 7.8 Hz) | $CDCl_3$ (300 MHz) | 597 ($M^+$ + 1) |
| 16 | 7-Deoxy-7-epi-7-(4-(thiazol-2-yl)phenylthio)lincomycin | 1.97 (3H, s), 2.28 (3H, s), 5.27 (1H, d, J = 5.1 Hz), 7.26 (1H, d, J = 3.3 Hz), 7.38 (2H, d, J = 8.4 Hz), 7.78 (1H, d, J = 3.3 Hz), 7.82 (2H, d, J = 8.4 Hz) | $CDCl_3$ (300 MHz) | 582 ($M^+$ + 1) |
| 17 | 7-Deoxy-7-(4-(4-(dimethylcarbamoyl)-thiazol-2-yl)phenylthio)-7-epilincomycin | 2.07 (3H, s), 2.38 (3H, s), 3.16 (3H, s), 3.36 (3H, s), 5.38 (1H, d, J = 5.4 Hz), 7.48 (2H, d, J = 8.4 Hz), 7.90 (1H, s), 7.91 (2H, d, J = 8.4 Hz) | $CDCl_3$ (300 MHz) | 653 ($M^+$ + 1) |
| 18 | 7-(4-(4-Carbamoylthiazol-2-yl)phenylthio)-7-deoxy-7-epilincomycin | 2.04 (3H, s), 2.35 (3H, s), 5.23 (1H, d, J = 5.7 Hz), 7.47 (2H, d, J = 8.4 Hz), 7.89 (2H, d, J = 8.4 Hz), 8.16 (1H, s) | $CDCl_3$ (300 MHz) | 625 ($M^+$ + 1) |
| 19 | 7-(4-(5-Carbamoylthiazol-2-yl)phenylthio)-7-deoxy-7-epilincomycin | 2.02 (3H, s), 2.40 (3H, s), 5.35 (1H, d, J = 6.6 Hz), 7.46 (2H, d, J = 8.4 Hz), 7.90 (2H, d, J = 8.4 Hz), 8.25 (1H, s) | $CDCl_3$ (300 MHz) | 625 ($M^+$ + 1) |
| 20 | 7-Deoxy-7-(4-(5-(dimethylcarbamoyl)-thiazol-2-yl)phenylthio)-7-epilincomycin | 1.98 (3H, s), 2.05 (3H, s), 2.31 (6H, s), 5.30 (1H, d, J = 4.2 Hz), 7.40 (2H, d, J = 8.1 Hz), 7.81 (2H, d, J = 8.1 Hz), 8.80 (1H, s) | $CDCl_3$ (300 MHz) | 653 ($M^+$ + 1) |
| 22 | 7-Deoxy-7-epi-7-(4-(1,3,4-thiadiazol-2-yl)phenylthio)lincomycin | 2.03 (3H, s), 2.40 (3H, s), 5.37 (1H, d, J = 5.7 Hz), 7.50 (2H, d, J = 8.4 Hz), 7.96 (2H, d, J = 8.4 Hz), 9.14 (1H, s) | $CDCl_3$ (300 MHz) | 583 ($M^+$ + 1) |

TABLE 3

| Compound No. | Compound name | NMR data δ (ppm) from TMS | Solvent/Hz | MS (FAB+) |
|---|---|---|---|---|
| 23 | 7-Deoxy-7-epi-7-(4-(isoxazol-5-yl)phenylthio)lincomycin | 2.05 (3H, s), 2.39 (3H, s), 5.37 (1H, d, J = 5.1 Hz), 6.53 (1H, s), 7.49 (2H, d, J = 7.5 Hz), 7.74 (2H, d, J = 7.5 Hz), 8.31 (1H, s) | $CDCl_3$ (300 Hz) | 566 ($M^+$ + 1) |
| 24 | 7-Deoxy-7-epi-7-(4-(1,2,3-thiadiazol-4-yl)phenylthio)lincomycin | 2.07 (3H, s), 2.35 (3H, s), 5.36 (1H, d, J = 5.4 Hz), 7.55 (2H, d, J = 7.2 Hz), 8.00 (2H, d, J = 7.2 Hz), 8.67 (1H, s) | $CDCl_3$ (300 Hz) | 583 ($M^+$ + 1) |
| 25 | 7-Deoxy-7-epi-7-(4-(pyrazin-2-yl)phenylthio)lincomycin | 2.39 (3H, s), 3.05 (3H, s), 5.38 (1H, d, J = 5.4 Hz), 7.55 (2H, d, J = 8.1 Hz), 7.90 (2H, d, J = 8.1 Hz), 8.53 (1H, d, J = 2.4 Hz), 8.64 (1H, d, J = 2.4 Hz), 9.03 (1H, s) | $CDCl_3$ (300 Hz) | 577 ($M^+$ + 1) |
| 26 | 7-Deoxy-7-epi-7-(4-(thiazol-4-yl)phenylthio)lincomycin | 2.13 (3H, s), 2.35 (3H, s), 5.38 (1H, d, J = 5.1 Hz), 7.50 (2H, d, J = 8.1 Hz), | $CDCl_3$ (300 Hz) | 582 ($M^+$ + 1) |

TABLE 3-continued

| Compound No. | Compound name | NMR data δ (ppm) from TMS | Solvent/Hz | MS (FAB+) |
|---|---|---|---|---|
| | | 7.57 (1H, s), 7.89 (2H, d, J = 8.1 Hz), 8.90 (1H, s) | | |
| 27 | 7-Deoxy-7-epi-7-(4-(oxazol-5-yl)phenylthio)lincomycin | 2.10 (3H, s), 2.37 (3H, s), 5.37 (1H, d, J = 5.7 Hz), 7.38 (1H, s), 7.48 (2H, d, J = 8.4 Hz), 7.61 (2H, d, J = 8.4 Hz), 7.94 (1H, s) | CDCl₃ (300 Hz) | 566 (M+ + 1) |
| 28 | 7-Deoxy-7-epi-7-(4-(thiazol-5-yl)phenylthio)lincomycin | 2.12 (3H, s), 2.37 (3H, s), 5.37 (1H, d, J = 4.8 Hz), 7.46 (2H, d, J = 8.1 Hz), 7.57 (2H, d, J = 8.1 Hz), 8.01 (1H, s), 8.78 (1H, s) | CDCl₃ (300 Hz) | 582 (M+ + 1) |
| 29 | 7-Deoxy-7-(4-(4-dimethylcarbamoyl-thiazol-5-yl)phenylthio)-7-epilincomycin | 2.07 (3H, s), 2.40 (3H, s), 2.80 (3H, s), 3.10 (3H, s), 5.38 (1H, d, J = 4.8 Hz), 7.42 (2H, d, J = 8.1 Hz), 7.50 (2H, d, J = 8.1 Hz), 8.77 (1H, s) | CDCl₃ (300 MHz) | 653 (M+ + 1) |
| 30 | 7-(4-(5-Aminopyrazin-2-yl)phenylthio)-7-deoxy-7-epilincomycin | 2.12 (3H, s), 2.36 (3H, s), 5.39 (1H, d, J = 5.7 Hz), 7.49 (2H, d, J = 8.1 Hz), 7.83 (2H, d, J = 8.1 Hz), 8.06 (1H, s), 8.43 (1H, s) | CDCl₃ (300 MHz) | 592 (M+ + 1) |
| 31 | 7-Deoxy-7-epi-7-(4-(6-oxo-1,4,5,6-tetrahydropyridazin-3-yl)phenylthio)lincomycin | 2.05 (3H, s), 2.39, (3H, s), 2.62 (2H, t, J = 8.1 Hz), 2.98 (2H, t, J = 8.1 Hz), 5.37 (1H, d, J = 5.1 Hz), 7.42 (2H, d, J = 8.4 Hz), 7.67 (2H, d, J = 8.4 Hz), 9.06 (1H, s) | CDCl₃ (300 Hz) | 595 (M+ + 1) |
| 32 | 7-Deoxy-7-epi-7-(4-(2-oxopyrrolidin-1-yl)phenylthio)lincomycin | 2.04 (3H, s), 2.39 (3H, s), 5.28 (1H, d, J = 5.6 Hz), 7.42 (2H, d, J = 8.8 Hz), 7.45 (2H, d, J = 8.8 Hz) | CD₃OD (400 MHz) | 582 (M+ + 1) |
| 33 | 7-Deoxy-7-epi-7-(4-(1-methyl-1,2,3,6-tetrahydropyridin-3-yl)phenylthio)lincomycin | 1.98 (3H, s), 2.37 (3H, s), 2.47 (3H, s), 2.36-2.46 (2H, m), 2.65 (2H, t, J = 6.0 Hz), 3.34 (2H, s), 5.26 (1H, d, J = 5.4 Hz), 6.19-6.24 (1H, m), 7.35 (2H, d, J = 8.4 Hz), 7.39 (2H, d, J = 8.4 Hz). | CD₃OD (300 MHz) | 594 (M+ + 1) |
| 34 | 7-Deoxy-7-epi-7-(4-(1-ethyl-1,2,3,6-tetrahydropyridin-3-yl)phenylthio)lincomycin | 1.20 (3H, t, J = 7.2 Hz), 1.98 (3H, s), 2.36-2.45 (2H, m), 2.37 (3H, s), 2.66 (2H, q, J = 7.2 Hz), 2.69 (2H, t, J = 6.0 Hz), 3.38 (2H, d, J = 2.1 Hz), 5.27 (1H, d, J = 5.7 Hz), 6.19-6.24 (1H, m), 7.35 (2H, d, J = 8.4 Hz), 7.40 (2H, d, J-8.7 Hz). | CD₃OD (300 MHz) | 608 (M+ + 1) |
| 35 | 7-Deoxy-7-epi-7-(4-(1-(2-hydroxyethyl)-1,2,3,6-tetrahydropyridin-3-yl)phenylthio)lincomycin | 1.98 (3H, s), 2.37 (3H, s), 2.36-2.44 (2H, m), 2.76 (2H, t, J = 5.7 Hz), 2.76 (2H, t, J = 6.0 Hz), 3.46 (2H, d, J = 1.8 Hz), 3.79 (2H, t, J = 6.0 Hz), 5.26 (1H, d, J = 5.7 Hz), 6.20-6.24 (1H, m), 7.35 (2H, d, J = 8.7 Hz), 7.39 (2H, d, J = 8.7 Hz). | CD₃OD (300 MHz) | 624 (M+ + 1) |
| 36 | 7-Deoxy-7-epi-7-(4-(1-(2-methoxyethyl)-1,2,3,6-tetrahydropyridin-3-yl)phenylthio)lincomycin | 1.98 (3H, s), 2.35-2.44 (2H, m), 2.37 (3H, s), 2.74 (2H, t, J = 5.7 Hz), 2.80 (2H, t, J = 5.7 Hz), 3.44 (2H, d, J = 1.8 Hz), 3.63 (2H, t, J = 5.7 Hz), 5.26 (1H, d, J = 5.4 Hz), 6.19-6.24 (1H, m), 7.34 (2H, d, J = 8.7 Hz), 7.39 (2H, d, J = 8.4 Hz). | CD₃OD (300 MHz) | 638 (M+ + 1) |
| 37 | 7-Deoxy-7-(4-(1-(2-dimethylaminoethyl)-1,2,3,6-tetrahydropyridin-3-yl)phenylthio)-7-epilincomycin | 1.98 (3H, s), 2.31 (6H, s), 2.36-2.42 (2H, m), 2.37 (3H, s), 2.60-2.64 (2H, m), 2.67-2.74 (4H, m), 3.38 (2H, d, J = 2.0 Hz), 5.26 (1H, d, J = 5.6 Hz), 6.19-6.23 (1H, m), 7.35 (2H, d, J = 8.8 Hz), 7.39 (2H, d, J = 8.8 Hz). | CD₃OD (400 MHz) | 651 (M+ + 1) |
| 38 | 7-Deoxy-7-epi-7-(4-(2-2-thioxo-2,3-dihydro-1H-imidazol-1-yl)phenylthio)lincomycin | 2.12 (3H, s), 2.45 (3H, s), 4.32 (d, 1H, 2.7 Hz), 5.35 (1H, d, J = 5.4 Hz), 6.37 (2H, d, J = 8.7 Hz), 6.45 (d, 1H, J = 2.7 Hz), 6.93 (2H, d, J = 8.7 Hz) | CDCl₃ (300 Hz) | 597 (M+ + 1) |
| 39 | 4-((R)-5-(Acetamidemethyl)-2-oxooxazolidin-3-yl)-2-fluorophenylthio)-7-deoxy-7-epilincomycin | 2.03 (3H, s), 2.27 (3H, s), 2.37 (3H, s), 3.00-3.60 (4H, m), 5.38 (1H, d, J = 5.4 Hz), 7.19 (1H, d, J = 8.4 Hz), 7.43 (1H, d, J = 5.1 Hz), 7.52 (1H, d, J = 8.4 Hz) | CDCl₃ (300 Hz) | 673 (M+ + 1) |
| 40 | 7-Deoxy-7-epi-7-(5-(oxoxazol-5-yl)thiophen-2-ylthio)lincomycin | 2.25 (3H, s), 2.30 (3H, s), 5.40 (1H, d, J = 5.7 Hz), 7.18 (1H, d, J = 3.9 Hz), 7.23 (1H, d, J = 3.9 Hz), 7.25 (1H, s), 7.88 (1H, s) | CDCl₃ (300 MHz) | 572 (M+ + 1) |
| 41 | 7-Deoxy-7-epi-7-(5-(pyrimidin-5-yl)thiophen-2-ylthio)lincomycin | 2.31 (6H, s), 5.41 (1H, d, J = 5.4 Hz), 7.25 (1H, d, J = 3.6 Hz), 7.34 (1H, d, J = 3.6 Hz), 8.92 (2H, s), 9.16 (1H, s) | CDCl₃ (300 MHz) | 583 (M+ + 1) |

TABLE 3-continued

| Compound | | NMR data | | MS |
|---|---|---|---|---|
| No. | Compound name | δ (ppm) from TMS | Solvent/Hz | (FAB+) |
| 42 | 7-Deoxy-7-epi-7-(5-(pyrimidin-5-yl)pyridin-2-ylthio)lincomycin | 2.01 (3H, s), 2.43 (3H, s), 5.30 (1H, d, J = 5.7 Hz), 8.05 (2H, d, J = 1.5 Hz), 8.74 (1H, t, J = 1.5 Hz), 9.18 (1H, s), 9.42 (2H, s). | CD$_3$OD (300 MHz) | 578 (M+ + 1) |
| 43 | 7-Deoxy-7-epi-7-(6-(pyrimidin-5-yl)pyridin-3-ylthio)lincomycin | 1.99 (3H, s), 2.43 (3H, s), 5.28 (1H, d, J = 5.4 Hz), 8.00 (2H, d, J = 1.5 Hz), 8.72 (1H, t, J = 1.5 Hz), 9.19 (1H, s), 9.41 (2H, s). | CD$_3$OD (300 Hz) | 578 (M+ + 1) |
| 44 | 7-Deoxy-7-epi-7-(6-(1-methyl-1,2,5,6-tetrahydropyridin-3-yl)pyridin-3-ylthio)lincomycin | 2.00 (3H, s), 2.37 (3H, s), 2.54 (3H, s), 5.25 (1H, d, J = 5.6 Hz), 6.73 (1H, dddd, J = 2.2, 2.2, 2.2, 2.2 Hz), 7.56 (1H, d, J = 8.3 Hz), 7.83 (1H, dd, J = 8.3, 2.0 Hz), 8.51 (1H, d, J = 2.0 Hz), | CD$_3$OD (400 MHz) | 595 (M+ + 1) |

TABLE 4

| Compound | | NMR data | | MS |
|---|---|---|---|---|
| No. | Compound name | δ (ppm) from TMS | Solvent/Hz | (FAB+) |
| 45 | 7-(5,5'-Bipyrimidin-2-ylthio)-7-deoxy-7-epilincomycin | 1.92 (3H, s), 2.44 (3H, s), 5.35 (1H, d, J = 5.7 Hz), 8.79 (2H, s), 9.02 (2H, s), 9.32 (1H, s) | CDCl$_3$ (300 MHz) | 579 (M+ + 1) |
| 46 | 7-(5,5'-Bipyrimidin-5-ylthio)-7-deoxy-7-epilinocomycin | 2.17 (3H, s), 2.37 (3H, s), 5.36 (1H, d, J = 5.7 Hz), 8.89 (2H, s), 9.34 (1H, s), 9.70 (2H, s) | CDCl$_3$ (300 MHz) | 579 (M+ + 1) |
| 47 | 7-Deoxy-7-epi-7-(4-(piperazin-1-yl)phenylthio)lincomycin | 2.25 (3H, s), 2.31 (3H, s), 2.95-3.05 (4H, m), 3.15-3.25 (4H, m), 5.38 (1H, d, J = 5.4 Hz), 6.83 (2H, d, J = 8.4 Hz), 7.36 (2H, d, J = 8.4 Hz) | CDCl$_3$ (300 MHz) | 583 (M+ + 1) |
| 48 | 7-Deoxy-7-epi-7-(4-(4-hydroxypiperidin-4-yl)phenylthio)lincomycin | 1.97 (3H, s), 2.40 (3H, s), 5.25 (1H, d, J = 5.6 Hz), 7.32-7.50 (4H, m) | CD$_3$OD (400 MHz) | 598 (M+ + 1) |
| 49 | 7-(6-(3-Aminopyrrolidin-1-yl)pyridin-3-ylthio)-7-deoxy-7-epilincomycin | 2.26 (3H, s), 2.32 (3H, s), 5.36 (1H, d, J = 5.4 Hz), 6.33 (1H, d, J = 8.7 Hz), 7.52 (1H, d, J = 8.7 Hz), 8.21 (1H, s) | CDCl$_3$ (300 Hz) | 584 (M+ + 1) |
| 50 | 7-Deoxy-7-epi-7-(4-(piperidin-3-yl)phenylthio)lincomycin | 1.59-1.69 (2H, m), 1.98 (3H, s), 2.38 (3H, s), 2.58-2.76 (3H, m), 3.06 (2H, brd, J = 11.1 Hz), 5.25 (1H, d, J = 5.4 Hz), 7.20 (2H, d, J = 8.1 Hz), 7.37 (2H, d, J = 8.4 Hz). | CD$_3$OD (300 MHz) | 582 (M+ + 1) |
| 51 | 7-Deoxy-7-epi-7-(4-(1-methylpiperidin-3-yl)phenylthio)lincomycin | 1.40-1.53 (1H, m), 1.66-2.11 (5H, m), 1.98 (3H, s), 2.33 (3H, s), 2.39 (3H, s), 2.74-2.86 (1H, m), 2.90-2.97 (2H, m), 5.25 (1H, d, J = 5.7 Hz), 7.21 (2H, d, J = 8.4 Hz), 7.38 (2H, d, J = 8.4 Hz). | CD$_3$OD (300 Hz) | 596 (M+ + 1) |
| 52 | 7-Deoxy-7-epi-7-(4-(4-methylpiperazin-1-yl)phenylthio)lincomycin | 2.25 (3H, s), 2.30 (3H, s), 2.36 (3H, s), 2.45-2.55 (4H, m), 3.20-3.30 (4H, m), 5.38 (1H, d, J = 5.7 Hz), 6.84 (2H, d, J = 9.0 Hz), 7.36 (2H, d, J = 9.0 Hz) | CDCl$_3$ (300 MHz) | 597 (M+ + 1) |
| 53 | 7-Deoxy-7-epi-7-(4-(4-hydroxy-1-methylpiperidin-4-yl)phenylthio)lincomycin | 1.96 (3H, s), 2.45 (3H, s), 2.81 (3H, s), 5.26 (1H, d, J = 5.6 Hz), 7.42 (2H, d, J = 8.4 Hz), 7.46 (2H, d, J = 8.4 Hz) | CD$_3$OD (400 MHz) | 612 (M+ + 1) |
| 54 | 7-Deoxy-7-epi-7-(6-(3-(dimethylamino)-pyrrolidin-1-yl)pyridin-3-ylthio)lincomycin | 2.23 (6H, s), 2.34 (6H, s), 2.7-3.0 (5H, m), 5.35 (1H, d, J = 5.7 Hz), 6.31 (1H, d, J = 8.7 Hz), 7.37 (1H, d, J = 8.7 Hz), 8.24 (1H, s) | CDCl$_3$ (300 MHz) | 612 (M+ + 1) |
| 55 | 7-(4-(1-Acetylpiperidin-3-yl)phenylthio)-7-deoxy-7-epilincomycin | 1.50-1.93 (4H, m), 1.98 (3H, d, J = 3.9 Hz), 2.11 (3H, d, J = 8.7 Hz), 2.42 (3H, d, J = 2.7 Hz), 2.58-2.80 (2H, m), 3.10-3.22 (1H, m), 3.83-3.95 (1H, m), 4.51-4.60 (1H, m), 5.26 (1H, d, J = 6.0 Hz), 7.26 (2H, dd, J = 8.1, 8.4 Hz), 7.39 (2H, dd, J = 3.0 | CD$_3$OD (300 MHz) | 624 (M+ + 1) |
| 56 | 7-Deoxy-7-epi-7-(4-(1-ethylpiperidin-3-yl)phenylthio)lincomycin | 1.15 (3H, t, J = 7.2 Hz), 1.50-1.60 (1H, m), 1.70-2.19 (5H, m), 1.98 (3H, s), 2.39 (3H, s), 2.58 (2H, q, J = 7.2 Hz), | CD$_3$OD (300 MHz) | 610 (M+ + 1) |

TABLE 4-continued

| Compound No. | Compound name | NMR data δ (ppm) from TMS | Solvent/Hz | MS (FAB+) |
|---|---|---|---|---|
| | | 2.76-2.88 (1H, m), 3.04-3.16 (2H, m), 5.25 (1H, d, J = 5.7 Hz), 7.22 (2H, d, J = 8.4 Hz), 7.38 (2H, d, J = 8.4 Hz). | | |
| 57 | 7-Deoxy-7-epi-7-(6-(1-methyl-piperidin-3-yl)pyridin-3-ylthio)lincomycin | 2.00 (3H, s), 2.32 (3H, s), 2.38 (3H, s), 5.24 (1H, d, J = 5.6 Hz), 7.30 (1H, d, J = 8.3 Hz), 7.85 (1H, dd, J = 8.3, 2.4 Hz), 8.49 (1H, d, J = 2.4 Hz). | CD$_3$OD (400 MHz) | 597 (M+ + 1) |
| 58 | 1'-Demethyl-7-deoxy-7-epi-7-(4-(pyrimidin-5-yl)phenylthio)lincomycin | 1.95 (3H, s), 5.31 (1H, d, J = 5.4 Hz), 7.54 (2H, d, J = 8.4 Hz), 7.69 (2H, d, J = 8.4 Hz), 9.07 (2H, s), 9.13 (1H, s). | CD$_3$OD (300 MHz) | 563 (M+ + 1) |
| 59 | Methyl 7-deoxy-7-epi-6-N-((2S,4R)-4-propyl)pipecoloyl-7-(4-(pyrimidin-5-yl)phenylthio)-1-thio-α-lincosamide | 1.93 (3H, s), 5.31 (1H, d, J = 5.7 Hz), 7.54 (2H, d, J = 8.4 Hz), 7.69 (2H, d, J = 8.7 Hz), 9.07 (2H, s), 9.13 (1H, s). | CD$_3$OD (300 MHz) | 577 (M+ + 1) |
| 60 | Methyl 7-deoxy-7-epi-6-N-((2S,4R)-4-propyl)pipecoloyl-7-(4-(1,3,4-thiadiazol-2-yl)phenylthio)-1-thio-α-lincosamide | 1.93 (3H, s), 5.42 (1H, d, J = 4.8 Hz), 7.46 (2H, d, J = 8.4 Hz), 7.89 (2H, d, J = 8.4 Hz), 9.12 (1H, s) | CDCl$_3$ (300 MHz) | 583 (M+ + 1) |
| 61 | Methyl 7-deoxy-7-epi-7-(4-(isoxazole-5-yl)phenylthio)-6-N-((2S,4R)-4-propyl)pipecoloyl-1-thio-α-lincosamide | 2.01 (3H, s), 5.38 (1H, d, J = 5.1 Hz), 7.48 (2H, d, J = 8.4 Hz), 7.72 (2H, d, J = 8.4 Hz), 8.29 (1H, s) | CDCl$_3$ (300 MHz) | 566 (M+ + 1) |
| 62 | Methyl 7-deoxy-7-epi-6-N-((2S,4R)-4-propyl)pipecoloyl-7-(4-(1,2,3-thiadiazol-4-yl)phenylthio)-1-thio-α-lincosamide | 2.08 (3H, s), 5.39 (1H, d, J = 5.4 Hz), 7.56 (2H, d, J = 7.5 Hz), 8.00 (2H, d, J = 7.5 Hz), 8.67 (1H, s) | CDCl$_3$ (300 MHz) | 583 (M+ + 1) |
| 63 | Methyl 7-deoxy-7-epi-7-(4-(pyrazin-2-yl)phenylthio)-6-N-((2S,4R)-4-propyl)pipecoloyl-1-thio-α-lincosamide | 1.97 (3H, s), 5.42 (1H, d, J = 5.4 Hz), 7.49 (2H, d, J = 7.5 Hz), 7.93 (2H, d, J = 7.5 Hz), 8.49 (1H, s), 8.59 (1H, s), 8.99 (1H, s) | CDCl$_3$ (300 MHz) | 577 (M+ + 1) |
| 64 | Methyl 7-deoxy-7-epi-7-(4-(oxazol-5-yl)phenylthio)-6-N-((2S,4R)-4-propyl)pipecoloyl-1-thio-α-lincosamide | 1.98 (3H, s), 5.39 (1H, d, J = 5.4 Hz), 7.33 (1H, s), 7.43 (2H, d, J = 8.1 Hz), 7.56 (2H, d, J = 8.1 Hz), 7.93 (1H, s) | CDCl$_3$ (300 MHz) | 566 (M+ + 1) |
| 65 | Methyl 7-deoxy-7-epi-1-methyl6-N-((2S,4R)-4-propyl)pipecoloyl-7-(4-(pyrimidin-5-yl)phenylthio)-1-thio-α-lincosamide☐ | 1.94 (3H, s), 2.32 (3H, s), 5.30 (1H, d, J = 5.4 Hz), 7.55 (2H, d, J = 8.4 Hz), 7.70 (2H, d, J = 8.4 Hz), 9.07 (2H, s), 9.13 (1H, s). | CD$_3$OD (300 MHz) | 591 (M+ + 1) |
| 66 | Methyl 6-N-((2S,4R)-4-butyl)pipecoloyl-7-deoxy-7-epi-7-(4-(pyrimidin-5-yl)phenylthio)-1-thio-α-lincosamide☐ | 1.93 (3H, s), 5.29 (1H, d, J = 5.4 Hz), 7.54 (2H, d, J = 8.1 Hz), 7.69 (2H, d, J = 8.4 Hz), 9.07 (2H, s), 9.12 (1H, s). | CD$_3$OD (300 MHz) | 591 (M+ + 1) |

TABLE 5

| Compound No. | Compound name | NMR data δ (ppm) from TMS | Solvent/Hz | MS (FAB+) |
|---|---|---|---|---|
| 67 | Methyl 6-N-((2S,4R)-4-butyl-1-methyl-)pipecoloyl- | 1.94 (3H, s), 2.32 (3H, s), 5.30 (1H, d, J = 5.7 Hz), 7.55 (2H, d, J = 9.0 Hz), 7.70 (2H d, J = 8.7 Hz), | CD$_3$OD (300 Hz) | 605 (M+ + 1) |

TABLE 5-continued

| Compound No. | Compound name | NMR data δ (ppm) from TMS | Solvent/Hz | MS (FAB⁺) |
|---|---|---|---|---|
| | 7-deoxy-7-epi-7-(4-(pyrimidin-5-yl)phenylthio)-1-thio-α-lincosamide | 9.07 (2H, s), 9.13 (1H, s). | | |
| 68 | Methyl 6-N-((2S,4R)-4-cyclopropylmethyl)-pipecoloyl-7-deoxy-7-epi-7-(5-(4-(methylamino)thiazole-4-yl)-1,3,4-thiadiazol-2-ylthio)-1-thio-α-lincosamide | 2.17 (3H, s), 3.14 (3H, d, J = 5.4 Hz), 5.36 (1H, d, J = 5.7 Hz), 7.54 (1H, d, J = 5.4 Hz), 7.97 (1H, s) | CDCl₃ (300 Hz) | 631 (M⁺ + 1) |
| 69 | Methyl 6-N-((2S,4R)-4-cyclopropylmethyl)-pipecoloyl-7-deoxy-7-epi-7-(5-(5-methyl-2-nitrophenyl)-1,3,4-thiadiazol-2-ylthio)-1-thio-α-lincosamide | 2.20 (3H, s), 2.59 (3H, s), 5.42 (1H, d, J = 5.4 Hz), 7.54 (1H, s), 7.56 (2H, d, J = 7.8 Hz), 8.07 (2H, d, J = 7.8 Hz) | CDCl₃ (300 Hz) | 654 (M⁺ + 1) |
| 70 | Methyl 6-N-((2S,4R)-4-cyclopropylmethyl)pipecolilamide)-7-deoxy-7-(5-(4,5-dimethox-2-nitrophenyl)oxazol-2-ylthio)-7-epi-1-thio-α-lincosamide | 2.00 (3H, s), 3.94 (3H, s), 3.96 (3H, s), 5.26 (1H, d, J = 5.6 Hz), 7.14 (1H, s), 7.39 (1H, s), 7.61 (1H, s) | CD₃OD (400 Hz) | 683 (M⁺ + 1) |
| 71 | Methyl 6-N-((2S,4R)-4-cyclopropylmethyl)-pipecoloyl-7-deoxy-7-epi-7-(5-(4-(methylamino)thiazol-4-yl)-1,3,4-oxadiazol-2-ylthio)-1-thio-α-lincosamide | 2.13 (3H, s), 3.14 (3H, d, J = 4.8 Hz), 5.37 (1H, d, J = 5.1 Hz), 6.98 (1H, d, J = 5.1 Hz), 8.03 (1H, s) | CDCl₃ (300 Hz) | 615 (M⁺ + 1) |
| 72 | Methyl 6-N-((2S,4R)-4-cyclopropylmethyl)-pipecoloyl-7-deoxy-7-epi-7-(4-(pyrimidin-5-yl)phenylthio)-1-thio-α-lincosamide | −0.02-0.04 (2H, m), 0.40-0.47 (2H, m), 0.68-0.77 (1H, m), 1.36 (3H, d, J = 6.8 Hz), 1.93 (3H, s), 5.27 (1H, d, J = 5.6 Hz), 7.59 (2H, d, J = 8.5 Hz), 7.69 (2H, d, J = 8.5 Hz), 9.07 (2H, s), 9.12 (1H, s) | CD₃OD (400 MHz) | 589 (M⁺ + 1) |
| 73 | Methyl 6-N-((2S,4R)-4-cyclopropylmethyl)-pipecoloyl-7-deoxy-7-epi-7-(4-(pyridin-3-yl)phenylthio)-1-thio-α-lincosamide | −0.05-0.10 (2H, m), 0.40-0.50 (2H, m), 0.70-0.80 (1H, m), 1.10-1.30 (5H, m), 1.35 (3H, d, J = 6.8 Hz), 1.60-1.80 (2H, m), 1.95 (3H, s), 2.08 (1H, m), 2.66 (1H, m), 3.14 (1H, m), 3.57 (1H, m), 3.80-3.90 (2H, m), 4.09 (1H, dd, J = 5.4 Hz, 10.2 Hz) | CD₃OD (400 MHz) | 588 (M⁺ + 1) |
| 74 | Methyl 6-N-((2S,4R)-4-cyclopropylmethyl)-pipecoloyl-7-deoxy-7-epi-7-(4-(5-fluoropyridin-3-yl)phenylthio)-1-thio-α-lincosamide | 2.02 (3H, s), 5.42 (1H, d, J = 5.4 Hz), 7.50 (4H, s), 7.56 (1H, s), 8.50 (1H, s), 8.63 (1H, s) | CDCl₃ (300 MHz) | 606 (M⁺ + 1) |
| 75 | Methyl 6-N-((2S,4R)-4-cyclopropylmethyl)-pipecoloyl-7-deoxy-7-epi-7-(4-(6-fluoropyridin-3-yl)phenylthio)-1-thio-α-lincosamide | 2.01 (3H, s), 5.49 (1H, d, J = 4.8 Hz), 6.99 (1H, d, J = 8.4 Hz), 7.41 (2H, d, J = 8.1 Hz), 7.47 (2H, d, J = 8.1 Hz), 7.95 (1H, t, J = 8.4 Hz), 8.50 (1H, s) | CDCl₃ (300 MHz) | 606 (M⁺ + 1) |
| 76 | Methyl 6-N-((2S,4R)-4-cyclopropylmethyl)-pipecoloyl-7-deoxy-7-epi-7-(4-(4-nitro-1-oxidopyridin-3-yl)phenylthio)-1-thio-α-lincosamide | 1.88 (3H, s), 5.27 (1H, d, J = 5.6 Hz), 7.34 (2H, d, J = 8.3 Hz), 7.46 (2H, d, J = 8.3 Hz), 8.11 (1H, d, J = 7.0 Hz), 8.38 (1H, d, J = 2.0 Hz), 8.42 (1H, dd, J = 7.0, 2.0 Hz) | CD₃OD (400 MHz) | 649 (M⁺ + 1) |
| 77 | Methyl 7-(4-(5-cyanopyridin-3-yl)phenylthio)-6-N—(2S, | 1.98 (3H, s), 5.45 (1H, d, J = 5.4 Hz), 7.50 (4H, s), 8.10 (1H, s), 8.85 (1H, s), 8.98 (1H, s) | CDCl₃ (300 MHz) | 613 (M⁺ + 1) |

TABLE 5-continued

| Compound No. | Compound name | NMR data δ (ppm) from TMS | Solvent/Hz | MS (FAB+) |
|---|---|---|---|---|
| | 4R)-4-cyclopropylmethyl)-pipecoloyl-7-deoxy-7-epi-1-thio-α-lincosamide | | | |
| 78 | Methyl 6-N-((2S,4R)-4-cyclopropylmethyl)-pipecoloyl-7-deoxy-7-epi-7-(4-(5-methoxypyridin-3-yl)phenylthio)-1-thio-α-lincosamide | 2.09 (3H, s), 3.48 (3H, s), 5.37 (1H, d, J = 5.1 Hz), 7.57 (2H, d, J = 8.4 Hz), 7.61 (2H, d, J = 8.4 Hz), 8.12 (1H, s), 8.85 (1H, s), 9.00 (1H, s) | CDCl$_3$ (300 MHz) | 618 (M$^+$ + 1) |
| 79 | Methyl 6-N-((2S,4R)-4-cyclopropylmethyl)-pipecoloyl-7-deoxy-7-epi-7-(4-(methoxy(pyridin-2-yl)methyl)phenylthio)-1-thio-α-lincosamide | −0.01-0.04 (2H, m), 0.40-0.50 (2H, m), 0.65-0.75 (1H, m), 1.10-1.45 (5H, m), 1.28 (3H, d, J = 6.8 Hz), 1.60-1.85 (5H, m), 2.10 (1H, m), 2.67 (1H, m), 3.15 (1H, m), 3.37 (3H, s), 3.53 (1H, m), 3.75-3.85 (2H, m), 4.06 (1H, dd, J = 5.6 Hz, 10.2 Hz) | CD$_3$OD (400 MHz) | 632 (M$^+$ + 1) |
| 80 | Methyl 6-N-((2S,4R)-4-cyclopropylmethyl)-pipecoloyl-7-deoxy-7-epi-7-(4-(methoxy(pyridin-4-yl)methyl)phenylthio)-1-thio-α-lincosamide | −0.03-0.03 (2H, m), 0.40-0.45 (2H, m), 0.65-0.75 (1H, m), 1.10-1.20 (5H, m), 1.27 (3H, d, J = 6.6 Hz), 1.60-1.85 (5H, m), 2.05 (1H, m), 2.62 (1H, m), 3.12 (1H, m), 3.30 (3H, s), 3.53 (1H, m), 3.75-3.85 (2H, m), 4.04 (1H, dd, J = 5.6 Hz, 10.2 Hz), | CD$_3$OD (400 MHz) | 632 (M$^+$ + 1) |
| 81 | Methyl 6-N—(2S,4R)-4-cyclopropylmethyl)-pipecoloyl-7-deoxy-7-epi-7-(4-(isoxazol-5-yl)phenylthio)-1-thio-α-lincosamide | 2.01 (3H, s), 5.43 (1H, d, J = 5.4 Hz), 6.52 (1H, s), 7.51 (2H, d, J = 6.6 Hz), 7.72 (2H, d, J = 6.6 Hz), 8.30 (1H, s) | CDCl$_3$ (300 MHz) | 578 (M$^+$ + 1) |
| 82 | Methyl 6-N-((2S,4R)-4-cyclopropylmethyl)-pipecoloyl-7-deoxy-7-epi-7-(4-(1,2,3-thiadiazol-4-yl)phenylthio)-1-thio-α-lincosamide | 2.00 (3H, s), 5.47 (1H, d, J = 5.4 Hz), 7.49 (2H, d, J = 7.8 Hz), 7.96 (2H, d, J = 7.8 Hz), 8.72 (1H, s) | CDCl$_3$ (300 MHz) | 595 (M$^+$ + 1) |
| 83 | Methyl 6-N-((2S,4R)-4-cyclopropylmethyl)-pipecoloyl-7-deoxy-7-epi-7-(4-(pyrazin-2-yl)phenylthio)-1-thio-α-lincosamide | 1.80 (3H, s), 5.36 (1H, d, J = 5.4 Hz), 7.39 (2H, d, J = 7.8 Hz), 7.92 (2H, d, J = 7.8 Hz), 8.40 (1H, s), 8.50 (1H, s), 8.90 (1H, s) | CDCl$_3$ (300 MHz) | 589 (M$^+$ + 1) |
| 84 | Methyl 6-N-((2S,4R)-4-cyclopropylmethyl)-pipecoloyl-7-deoxy-7-(4-(4,6-diamino-1,3,5-triazin-2-yl)phenylthio)-7-epi-1-thio-α-lincosamide | 2.00 (3H, s), 5.37 (1H, d, J = 5.7 Hz), 6.59 (2H, d, J = 4.2 Hz), 7.29 (2H, d, J = 8.4 Hz), 7.47 (2H, d, J = 8.4 Hz) | CDCl$_3$ (300 MHz) | 620 (M$^+$ + 1) |
| 85 | Methyl 6-N-((2S,4R)-4-cyclopropylmethyl)-pipecoloyl-7-deoxy-7-epi-7-(4-(1-H-imidazol-1-yl)phenylthio)-1-thio-α-lincosamide | 2.09 (3H, s), 5.42 (1H, d, J = 5.1 Hz), 7.27 (2H, s), 7.29 (1H, s), 7.35 (2H, d, J = 8.1 Hz), 7.53 (2H, d, J = 8.1 Hz), 7.88 (1H, s) | CDCl$_3$ (300 MHz) | 577 (M$^+$ + 1) |
| 86 | Methyl 6-N-((2S,4R)-4-cyclopropylmethyl)-pipecoloyl-7-deoxy-7-epi-7-(4-(1-methyl-1,2,5,6-tetrahydropyridin-3-yl)phenylthio)-1-thio-α-lincosamide | 1.94 (3H, s), 2.35-2.44 (2H, m), 2.44 (3H, s), 2.61 (2H, t, J = 5.4 Hz), 3.28-3.36 (2H, m), 5.26 (1H, d, J = 5.4 Hz), 6.17-6.21 (1H, m), 7.32 (2H, d, J = 8.7 Hz), 7.36 (2H, d, J = 8.7 Hz). | CD$_3$OD (300 MHz) | 606 (M$^+$ + 1) |
| 87 | Methyl 6-N-((2S,4R)-4-cyclopropylmethyl)-pipecoloyl-7-deoxy-7-epi-7-(4-(1-ethyl-1,2,5,6-tetrahydropyridin-3-yl)phenylthio)-1-thio-α-lincosamide | 1.19 (3H, t, J = 7.2 Hz), 1.94 (3H, s), 2.35-2.43 (2H, m), 2.63 (2H, q, J = 7.2 Hz), 2.66 (2H, t, J = 5.7 Hz), 3.35 (2H, s), 5.26 (1H, d, J = 5.7 Hz), 6.18-6.21 (1H, m), 7.32 (2H, d, J = 9.0 Hz), 7.36 (2H, d, J = 9.0 Hz). | CD$_3$OD (300 MHz) | 620 (M$^+$ + 1) |
| 88 | Methyl 6-N-((2S,4R)-4-cyclopropylmethyl)-pipecoloyl- | −0.08-0.05 (2H, m), 0.36-0.48 (2H, m), 0.63-0.78 (1H, m), 1.34 (3H, d, J = 6.8 Hz), 1.88 (3H, s), | CD$_3$OD (400 MHz) | 624 (M$^+$ + 1) |

TABLE 5-continued

| Compound No. | Compound name | NMR data δ (ppm) from TMS | Solvent/Hz | MS (FAB+) |
|---|---|---|---|---|
| | 7-deoxy-7-epi-7-(4-(morpholinecarbonyl)-phenylthio)-1-thio-α-lincosamide | 3.45-3.80 (8H, br), 5.24 (1H, d, J = 5.6 Hz), 7.37 (2H, d, J = 8.3 Hz), 7.44 (2H, d, J = 8.3 Hz) | | |

TABLE 6

| Compound No. | Compound name | NMR data δ (ppm) from TMS | Solvent/Hz | MS (FAB+) |
|---|---|---|---|---|
| 89 | Methyl 6-N-((2S,4R)-4-cyclopropylmethyl)-pipecoloyl-7-deoxy-7-epi-7-(5-(pyridin-3-yl)pyridin-2-ylthio)-1-thio-α-lincosamide | 1.83 (3H, s), 5.24 (1H, d, J = 5.6 Hz), 7.45 (1H, d, J = 8.5 Hz), 7.55 (1H, dd, J = 8.0, 4.9 Hz), 7.95 (1H, dd, J = 8.5, 2.5 Hz), 8.13 (1H, ddd, J = 8.0, 1.5, 1.5 Hz), 8.57 (1H, dd, J = 4.9, 1.5 Hz), 8.75 (1H, d, J = 2.5 Hz), 8.83 (1H, d, J = 1.5 Hz) | CD$_3$OD (400 MHz) | 589 (M+ + 1) |
| 90 | Methyl 6-N-((2S,4R)-4-cyclopropylmethyl)-pipecoloyl-7-deoxy-7-epi-7-(5-(pyridin-5-yl)pyridin-2-ylthio)-1-thio-α-lincosamide | 1.84 (3H, s), 5.29 (1H, d, J = 6.0 Hz), 7.50 (1H, d, J = 8.4 Hz), 8.03 (1H, dd, J = 2.7, 8.4 Hz), 8.83 (1H, d, J = 2.7 Hz), 9.14 (2H, s), 9.20 (1H, s). | CD$_3$OD (300 MHz) | 590 (M+ + 1) |
| 91 | Methyl 6-N-((2S,4R)-4-cyclopropylmethyl)-pipecoloyl-7-deoxy-7-epi-7-(6-(pyrimidin-5-yl)pyridin-3-ylthio)-1-thio-α-lincosamide | 1.99 (3H, s), 5.32 (1H, d, J = 5.7 Hz), 8.01 (2H, d, J = 1.2 Hz), 8.73 (1H, t, J = 1.5 Hz), 9.21 (1H, s), 9.42 (2H, s). | CD$_3$OD (300 MHz) | 590 (M+ + 1) |
| 92 | Methyl 6-N-((2S,4R)-4-cyclopropylmethyl)-pipecoloyl-7-deoxy-7-epi-7-(6-(pyridin-3-yl)pyridin-3-ylthio)-1-thio-α-lincosamide | 1.98 (3H, s), 5.27 (1H, d, J = 5.6 Hz), 7.55 (1H, dd, J = 7.9, 4.9 Hz), 7.91-7.93 (1H, m), 7.97 (1H, dd, J = 8.3, 2.2 Hz), 8.43-8.46 (1H, m), 8.59 (1H, dd, J = 4.9, 1.4 Hz), 8.68-8.69 (1H, m), 9.17-9.18 (1H, m) | CD$_3$OD (400 MHz) | 589 (M+ + 1) |
| 93 | Methyl 6-N-((2S,4R)-4-cyclopropylmethyl)-pipecoloyl-7-deoxy-7-epi-7-(6-(1-methyl-1,2,3,6-tetrahydropyridin-3-yl)pyridin-3-ylthio)-1-thio-α-lincosamide | 1.98 (3H, s), 2.49 (3H, s), 5.25 (1H, d, J = 5.6 Hz), 6.64-6.74 (1H, m), 7.53 (1H, d, J = 8.5 Hz), 7.80 (1H, dd, J = 8.5, 2.4 Hz), 8.47 (1H, d, J = 2.4 Hz) | CD$_3$OD (400 MHz) | 607 (M+ + 1) |
| 94 | Methyl 6-N-((2S,4R)-4-cyclopropylmethyl)-pipecoloyl-7-deoxy-7-epi-7-(4-(4-morpholin-2-yl)phenylthio)-1-thio-α-lincosamide | 1.90-1.91 (3H, m), 2.29 (3H, s) 5.25 (1H, d, J = 5.6 Hz), 7.27 (2H, d, J = 8.4 Hz), 7.35 (2H, d, J = 8.4 Hz) | CD$_3$OD (400 MHz) | 610 (M+ + 1) |
| 95 | Methyl 6-N-((2S,4R)-4-cyclopropylmethyl)-pipecoloyl-7-deoxy-7-epi-7-(4-(1-methylpiperidin-3-yl)phenylthio)-1-thio-α-lincosamide | 1.40-1.52 (1H, m), 1.60-2.06 (5H, m), 1.95 (3H, s), 2.30 (3H, s), 2.71-2.83 (1H, m), 2.86-2.96 (2H, m), 5.25 (1H, d, J = 5.4 Hz), 7.18 (2H, d, J = 8.1 Hz), 7.35 (2H, d, J = 8.1 Hz). | CD$_3$OD (300 MHz) | 608 (M+ + 1) |
| 96 | Methyl 6-N-((2S,4R)-4-cyclopropylmethyl-1-methyl)pipecoloyl-7-deoxy-7-epi-7-(5-(4-(methylamino)thiazol-4-yl)-1,3,4-thiadiazol-2-ylthio)-1-thio-α-lincosamide | 2.19 (3H, s), 2.21 (3H, s), 3.15 (3H, d, J = 4.8 Hz), 5.35 (1H, d, J = 5.4 Hz), 7.60 (1H, d, J = 4.8 Hz), 7.99 (1H, s) | CDCl$_3$ (300 MHz) | 645 (M+ + 1) |
| 97 | Methyl 6-N-((2S,4R)-4-cyclopropylmethyl-1-methyl)pipecoloyl-7-deoxy-7-epi-7-(5-(4,5-dimethox-2-nitrophenyl)oxazol- | 2.02 (3H, s), 2.33 (3H, s), 3.94 (3H, s), 3.96 (3H, s), 5.27 (1H, d, J = 5.6 Hz), 7.14 (1H, s), 7.40 (1H, s), 7.61 (1H, s) | CD$_3$OD (400 MHz) | 697 (M+ + 1) |

TABLE 6-continued

| Compound No. | Compound name | NMR data δ (ppm) from TMS | Solvent/Hz | MS (FAB⁺) |
|---|---|---|---|---|
| | 2-ylthio)-1-thio-α-lincosamide | | | |
| 98 | Methyl 6-N-((2S,4R)-4-cyclopropylmethyl-pipecoloyl)-7-deoxy-7-epi-7-(5-(3,4-dimethoxy-2-nitrophenyl)-1,3,4-oxadiazol-2-ylthio)-1-thio-α-lincosamide | −0.03-0.03 (2H, m), 0.39-0.47 (2H, m), 0.65-0.77 (1H, m), 1.55 (3H, d, J = 7.1 Hz), 2.05 (3H, s), 3.98 (3H, s), 4.00 (3H, s), 5.28 (1H, d, J = 5.6 Hz), 7.35 (1H, s), 7.78 (1H, s) | $CD_3OD$ (400 MHz) | 684 (M + 1)⁺ |
| 99 | Methyl 6-N-((2S,4R)-4-cyclopropylmethyl-1-methyl)pipecoloyl-7-deoxy-7-epi-7-(5-(4-(methylamino)thiazol-4-yl)-1,3,4-oxadiazol-2-ylthio)-1-thio-α-lincosamide | 2.19 (3H, s), 2.21 (3H, s), 3.15 (3H, d, J = 4.8 Hz), 5.35 (1H, d, J = 5.4 Hz), 7.00 (1H, d, J = 4.8 Hz), 8.03 (1H, s) | $CDCl_3$ (300 MHz) | 629 (M⁺ + 1) |
| 100 | Methyl 6-N-((2S,4R)-4-cyclopropylmethyl-1-methyl)pipecoloyl-7-deoxy-7-epi-7-(4-(pyrimidin-5-yl)phenylthio)-1-thio-α-lincosamide | −0.06-0.03 (2H, m), 0.38-0.46 (2H, m), 0.62-0.74 (1H, m), 1.38 (3H, d, J = 7.1 Hz), 1.95 (3H, s), 2.27 (3H, s), 5.27 (1H, d, J = 5.6 Hz), 7.59 (2H, d, J = 8.6 Hz), 7.69 (2H, d, J = 8.6 Hz), 9.07 (2H, s), 9.12 (1H, s) | $CD_3OD$ (400 MHz) | 603 (M + 1)⁺ |
| 101 | Methyl 6-N-((2S,4R)-4-cyclopropylmethyl-1-methyl)pipecoloyl-7-deoxy-7-epi-7-(4-(pyridin-3-yl)phenylthio)-1-thio-α-lincosamide | −0.05-0.05 (2H, m), 0.40-0.40 (2H, m), 0.70-0.80 (1H, m), 1.37 (3H, d, J = 7.1 Hz), 1.40-1.80 (2H, m), 1.97 (3H, s), 4.11 (1H, dd, J = 5.4 Hz, 10.2 Hz), 4.43 (1H, m), 4.61 (1H, m), 5.27 (1H, d, J = 5.6 Hz), 7.50-7.60 (3H, m), 7.64 (1H, d, J = 6.6 Hz), 8.10 (1H, m), 8.51 (1H, m), 8.80 (1H, m) | $CD_3OD$ (400 MHz) | 602 (M⁺ + 1) |
| 102 | Methyl 6-N-((2S,4R)-4-cyclopropylmethyl-1-methyl)pipecoloyl-7-deoxy-7-epi-7-(4-(5-fluoropyridin-3-yl)phenylthio)-1-thio-α-lincosamide | 2.12 (3H, s), 2.27 (3H, s), 5.40 (1H, d, J = 5.7 Hz), 7.55 (4H, s), 7.57 (1H, s), 8.49 (1H, s), 8.68 (1H, s) | $CDCl_3$ (300 MHz) | 620 (M⁺ + 1) |
| 103 | Methyl 6-N-((2S,4R)-4-cyclopropylmethyl-1-methyl)pipecoloyl-7-deoxy-7-epi-7-(4-(6-fluoropyridin-3-yl)-phenylthio)-1-thio-α-lincosamide | 2.11 (3H, s), 2.25 (3H, s), 5.40 (1H, d, J = 5.7 Hz), 7.05 (1H, d, J = 8.1 Hz), 7.50 (2H, d, J = 8.4 Hz), 7.55 (2H, d, J = 8.4 Hz), 7.94 (1H, t, J = 8.1 Hz), 8.42 (1H, s), | $CDCl_3$ (300 MHz) | 620 (M⁺ + 1) |
| 104 | Methyl 7-(4-(5-cyanopyridin-3-yl)phenylthio)-6-N-((2S,4R)-4-cyclopropylmethyl-1-methyl)pipecoloyl-7-deoxy-7-epi-1-thio-α-lincosamide | 1.98 (3H, s), 2.24 (3H, s), 5.43 (1H, d, J = 5.1 Hz), 7.52 (4H, s), 8.12 (1H, s), 8.84 (1H, s), 9.00 (1H, s) | $CDCl_3$ (300 MHz) | 627 (M⁺ + 1) |
| 105 | Methyl 6-N-((2S,4R)-4-cyclopropylmethyl-1-N-methyl)pipecoloyl-7-deoxy-7-epi-7-(4-(5-methoxypyridin-3-yl)phenylthio)-1-thio-α-lincosamide | 2.10 (3H, s), 2.25 (3H, s), 3.50 (3H, s), 5.39 (1H, d, J = 5.4 Hz), 7.56 (2H, d, J = 8.4 Hz), 7.59 (2H, d, J = 8.4 Hz), 8.14 (1H, s), 8.88 (1H, s), 9.03 (1H, s) | $CDCl_3$ (300 MHz) | 632 (M⁺ + 1) |
| 106 | Methyl 6-N-((2S,4R)-4-cyclopropylmethyl-1-methyl)pipecoloyl-7-deoxy-7-epi-7-(4-(methoxy(pyridin-2-yl)methyl)phenylthio)-1-thio-α-lincosamide | −0.03-0.07 (2H, m), 0.35-0.50 (2H, m), 0.65-0.75 (1H, m), 1.10-1.60 (5H, m), 1.29 (3H, d, J = 7.1 Hz), 1.75-1.85 (4H, m), 1.95 (1H, m), 2.10 (1H, m), 2.22 (3H, s), 2.62 (1H, m), 2.94 (1H, m), 3.37 (3H, s), 3.54 (1H, m), 3.75-3.85 (2H, m), 4.07 (1 | $CD_3OD$ (400 MHz) | 646 (M⁺ + 1) |
| 107 | Methyl 6-N-((2S,4R)-4-cyclopropylmethyl-1-methyl)pipecoloyl-7-deoxy-7-epi-7-(4-(methoxy(pyridin-4-yl)methyl)phenylthio)- | −0.04-0.03 (2H, m), 0.40-0.45 (2H, m), 1.30 (3H, d, J = 7.1 Hz), 2.23 (3H, s), 2.59 (1H, m), 2.93 (1H, m), 3.30 (3H, s), 4.07 (1H, dd, J = 5.6 Hz, 10.2 Hz), 5.21 (1H, d, J = 5.6 Hz), 5.36 (1H, s), 7.30 (1H, d, J = 8.3 Hz), | $CD_3OD$ (400 MHz) | 646 (M⁺ + 1) |

TABLE 6-continued

| Compound | | NMR data | | MS |
|---|---|---|---|---|
| No. | Compound name | δ (ppm) from TMS | Solvent/Hz | (FAB+) |
| | 1-thio-α-lincosamide | 7.35-7.40 (3H, m), 7.78 (1H, m), 8.41 (1H, m), 8.50 (1H, m) | | |
| 108 | Methyl 6-N-((2S,4R)-4-cyclopropylmethyl-1-methyl)pipecoloyl-7-deoxy-7-epi-7-(4-(1,2,3-thiadiazol-4-yl)-phenylthio)-1-thio-α-lincosamide | 2.11 (3H, s), 2.20 (3H, s), 5.38 (1H, d, J = 5.4 Hz), 7.59 (2H, d, J = 8.1 Hz), 8.02 (2H, d, J = 8.1 Hz), 8.67 (1H, s) | CDCl$_3$ (300 MHz) | 609 (M+ + 1) |
| 109 | Methyl 6-N-((2S,4R)-4-cyclopropylmethyl-1-methyl)pipecoloyl-7-deoxy-7-epi-7-(4-(pyrazin-2-yl)phenylthio)-1-thio-α-lincosamide | 1.88 (3H, s), 2.13 (3H, s), 5.39 (1H, d, J = 5.7 Hz), 7.40 (2H, d, J = 8.1 Hz), 7.90 (2H, d, J = 8.1 Hz), 8.40 (1H, s), 8.49 (1H, s), 8.93 (1H, s) | CDCl$_3$ (300 MHz) | 603 (M+ + 1) |

TABLE 7

| Compound | | NMR data | | MS |
|---|---|---|---|---|
| No. | Compound name | δ (ppm) from TMS | Solvent/Hz | (FAB+) |
| 110 | Methyl 6-N-((2S,4R)-4-cyclopropylmethyl-1-methyl)pipecoloyl-7-deoxy-7-(4-(4,6-diamino-1,3,5-triazin-2-yl)phenylthio)-7-epi-1-thio-α-lincosamide | 2.02 (3H, s), 2.20 (3H, s), 5.39 (1H, d, J = 5.39 Hz), 6.57 (2H, d, J = 4.2 Hz), 7.28 (2H, d, J = 8.4 Hz), 7.45 (2H, d, J = 8.4 Hz) | CDCl$_3$ (300 MHz) | 634 (M+ + 1) |
| 111 | Methyl 6-N-((2S,4R)-4-cyclopropylmethyl-1-methyl)pipecoloyl-7-deoxy-7-epi-7-(4-(1-H-imidazol-1-yl)phenylthio)-1-thio-α-lincosamide | 2.13 (3H, s), 2.20 (3H, s), 5.37 (1H, d, J = 5.4 Hz), 7.21 (1H, s), 7.26 (1H, s), 7.35 (2H, d, J = 8.4 Hz), 7.55 (2H, d, J = 8.4 Hz), 7.86 (1H, s) | CDCl$_3$ (300 MHz) | 591 (M+ + 1) |
| 112 | Methyl 6-N-((2S,4R)-4-cyclopropylmethyl-1-methyl)pipecoloyl-7-deoxy-7-epi-7-(4-(4-morpholin-2-yl)phenylthio)-1-thio-α-lincosamide | 1.93-1.94 (3H, m), 2.27 (3H, s), 2.30 (3H, s), 5.25 (1H, d, J = 5.6 Hz), 7.29 (2H, d, J = 8.3 Hz), 7.37 (2H, d, J = 8.3 Hz) | CD3OD (400 MHz) | 610 (M+ + 1) |
| 113 | Methyl 6-N-((2S,4R)-4-cyclopropylmethyl-1-methyl)pipecoloyl-7-deoxy-7-epi-7-(4-(1-methyl-1,2,5,6-tetrahydropyridin-3-yl)phenylthio)-1-thio-α-lincosamide☐ | 1.97 (3H, s), 2.36-2.44 (2H, m), 2.47 (3H, s), 2.64 (2H, t, J = 5.7 Hz), 3.31-3.35 (2H, m), 5.28 (1H, d, J = 5.7 Hz), 6.19-6.23 (1H, m), 7.33 (2H, d, J = 9.0 Hz), 7.38 (d, J = 8.7 Hz). | CD$_3$OD (300 MHz) | 620 (M+ + 1) |
| 114 | Methyl 6-N-((2S,4R)-4-cyclopropylmethyl-1-methyl)pipecoloyl-7-deoxy-7-epi-7-(4-(1-ethyl-1,2,3,6-tetrahydropyridin-3-yl)phenylthio)-1-thio-α-lincosamide | 1.24 (3H, t, J = 7.2 Hz), 1.98 (3H, s), 2.29 (3H, s), 2.40-2.48 (2H, m), 2.73 (2H, q, J = 7.2 Hz), 2.76 (2H, t, J = 6.0 Hz), 3.45 (2H, d, J = 1.8 Hz), 5.29 (1H, d, J = 5.7 Hz), 6.22-6.26 (1H, m), 7.36 (2H, d, J = 8.7 Hz), 7.40 (2H, d, J = 8.7 Hz). | CD$_3$OD (300 MHz) | 634 (M+ + 1) |
| 115 | Methyl 6-N-((2S,4R)-4-cyclopropylmethyl-1-methyl)pipecoloyl-7-deoxy-7-epi-7-(4-(1-methylpiperidin-3-yl)phenylthio)-1-thio-α-lincosamide | 1.43-1.56 (1H, m), 1.65-2.17 (5H, m), 1.97 (3H, s), 2.25 (3H, s), 2.34 (3H, s), 2.73-2.85 (1H, m), 2.90-3.01 (2H, m), 5.26 (1H, d, J = 5.4 Hz), 7.20 (2H, d, J = 8.1 Hz), 7.36 (2H, d, J = 7.8 Hz). | CD$_3$OD (300 MHz) | 622 (M+ + 1) |
| 116 | Methyl 6-N-((2S,4R)-4-cyclopropylmethyl-1-methyl)pipecoloyl- | −0.03-0.05 (2H, m), 0.40-0.48 (2H, m), 0.65-0.76 (1H, m), 1.36 (3H, d, J = 7.1 Hz), 1.89 (3H, s), 2.26 (3H, s), | CD$_3$OD (400 MHz) | 638 (M + 1)+ |

TABLE 7-continued

| Compound No. | Compound name | NMR data δ (ppm) from TMS | Solvent/Hz | MS (FAB+) |
|---|---|---|---|---|
| | 7-deoxy-7-epi-7-(4-(morpholinecarbonyl)phenylthio)-1-thio-α-lincosamide | 3.70 (8H, br), 5.26 (1H, d, J = 5.8 Hz), 7.38 (2H, d, J = 8.3 Hz), 7.45 (2H, d, J = 8.3 Hz) | | |
| 117 | Methyl 6-N-((2S,4R)-4-cyclopropylmethyl-1-methyl)pipecoloyl-7-deoxy-7-epi-7-(5-(pyrimidin-5-yl)pyridin-2-ylthio)-1-thio-α-lincosamide | 1.90 (3H, s), 2.34 (3H, s), 5.29 (1H, d, J = 6.0 Hz), 7.52 (1H, d, J = 8.4 Hz), 8.05 (1H, dd, J = 2.4, 8.4 Hz), 8.84 (1H, d, J = 2.1 Hz), 9.15 (2H, s), 9.21 (1H, s). | CD$_3$OD (300 MHz) | 604 (M+ + 1) |
| 118 | Methyl 6-N-((2S,4R)-4-cyclopropylmethyl-1-methyl)pipecoloyl-7-deoxy-7-epi-7-(5-(pyridin-3-yl)pyridin-2-ylthio)-1-thio-α-lincosamide | 1.99 (3H, s), 2.46 (3H, s), 5.31 (1H, d, J = 5.7 Hz), 8.00 (2H, d, J = 1.5 Hz), 8.72 (1H, t, J = 1.5 Hz), 9.20 (1H, s), 9.41 (2H, s). | CD$_3$OD (300 MHz) | 604 (M+ + 1) |
| 119 | Methyl 6-N-((2S,4R)-4-cyclopropylmethyl-1-methyl)pipecoloyl-7-deoxy-7-epi-7-(6-(pyridin-3-yl)pyridin-3-ylthio)-1-thio-α-lincosamide | 2.00 (3H, s), 2.26 (3H, s), 5.27 (1H, d, J = 5.6 Hz), 7.56 (1H, dd, J = 8.0, 4.9 Hz), 7.92 (1H, d, J = 8.4 Hz), 7.98 (1H, dd, J = 8.4, 2.5 Hz), 8.45 (1H, ddd, J = 8.0, 1.7, 1.7 Hz), 8.59 (1H, dd, J = 4.9, 1.7 Hz), 8.69 (1H, d, J = 2.5 Hz), 9.18 (1H, d, J = 1.7 Hz) | CD$_3$OD (400 MHz) | 603 (M+ + 1) |
| 120 | Methyl 6-N-((2S,4R)-4-cyclopropylmethyl-1-methyl)pipecoloyl-7-deoxy-7-epi-7-(6-(1-methyl-1,2,5,6-tetrahydropyridin-3-yl)pyridin-3-ylthio)-1-thio-α-lincosamide | 1.97 (3H, s), 2.45 (3H, s), 2.81 (3H, s), 5.26 (1H, d, J = 5.6 Hz), 6.78 (1H, brs), 7.60 (1H, d, J = 8.5 Hz), 7.82 (1H, dd, J = 8.5, 2.4 Hz), 8.49 (1H, d, J = 2.4 Hz) | CD$_3$OD (400 MHz) | 621 (M+ + 1) |
| 121 | Methyl 6-N-((2S,4R)-4-cyclopropylmethyl-1-(2-hydroxy)ethyl)pipecoloyl-7-deoxy-7-epi-7-(4-(pyrimidin-5-yl)phenylthio)-1-thio-α-lincosamide | 1.96 (3H, s), 5.28 (1H, d, J = 5.7 Hz), 7.55 (2H, d, J = 8.6 Hz), 7.68 (2H, d, J = 8.6 Hz) 9.07 (2H, s), 9.12 (1H, s) | CD$_3$OD (400 MHz) | 633 (M+ + 1) |
| 122 | Methyl 6-N-((2S,4R)-1-cyclopropyl-4-cyclopropylmethyl)-pipecoloyl-7-deoxy-7-epi-7-(4-(pyrimidin-5-yl)phenylthio)-1-thio-α-lincosamide | −0.10-0.01 (2H, m), 0.31-0.46 (4H, m), 0.55-0.70 (2H, m), 0.75-0.86 (1H, m), 1.36 (3H, d, J = 6.8 Hz), 1.97 (3H, s), 5.29 (1H, d, J = 5.6 Hz), 7.56 (2H, d, J = 8.5 Hz), 7.70 (2H, d, J = 8.3 Hz) 9.06 (2H, s), 9.12 (1H, s) | CD$_3$OD (400 MHz) | 629 (M + 1)+ |
| 123 | Methyl 6-N-((2S, 5S)-5-propyl-2-azepancarbonyl)-7-deoxy-7-epi-7-(4-(pyrimidin-5-yl)phenylthio)-1-thio-α-lincosamide | 1.95 (3H, s), 5.27 (1H, d, J = 5.6 Hz), 7.56 (2H, d, J = 8.5 Hz), 7.69 (2H, d, J = 8.5 Hz) 9.07 (2H, s), 9.12 (1H, s) | CD$_3$OD (400 MHz) | 591 (M+ + 1) |
| 124 | Methyl 6-N-((2S, 5S)-1-methyl-5-propyl-2-azepancarbonyl)-7-deoxy-7-epi-7-(4-(pyrimidin-5-yl)phenylthio)-1-thio-α-lincosamide | 2.02 (3H, s), 2.46 (3H, s), 5.30 (1H, d, J = 5.6 Hz), 7.59 (2H, d, J = 8.6 Hz), 7.67 (2H, d, J = 8.6 Hz) 9.05 (2H, s), 9.14 (1H, s) | CD$_3$OD (400 MHz) | 605 (M+ + 1) |
| 125 | Methyl 6-N-((2S,4R)-1-acetamidemethyl-4-cyclopropylmethyl)-pipecoloyl-7-deoxy-7-epi-7-(4-(pyrimidin-5-yl)phenylthio)-1-thio-α-lincosamide | −0.03-0.02 (2H, m), 0.39-0.46 (2H, m), 0.62-0.74 (1H, m), 1.40 (3H, d, J = 7.1 Hz), 1.93 (3H, s), 2.00 (3H, s), 5.27 (1H, d, J = 5.6 Hz), 7.55 (2H, d, J = 8.5 Hz), 7.68 (2H, d, J = 8.5 Hz), 9.06 (2H, s), 9.12 (1H, s) | CD$_3$OD (400 MHz) | 660 (M + 1)+ |
| 126 | Methyl 6-N-((2S,4R)-4-cyclopropylmethyl-1-ethoxycarbonyl)-pipecoloyl-7-deoxy-7-epi-7-(4-(pyrimidin-5-yl)phenylthio)-1-thio-α-lincosamide | −0.02-0.04 (2H, m), 0.40-0.47 (2H, m), 0.67-0.77 (1H, m), 1.38 (3H, d, J = 6.8 Hz), 1.93 (3H, s), 5.27 (1H, d, J = 5.3 Hz), 7.55 (2H, d, J = 8.5 Hz), 7.69 (2H, d, J = 8.5 Hz), 9.07 (2H, s), 9.12 (1H, s) | CD$_3$OD (400 MHz) | 661 (M + 1)+ |
| 127 | Methyl 6-N-((2S,4R)-4-cyclopropylmethyl-1-phenoxycarbonyl)- | 0.01-0.05 (2H, m), 0.42-0.49 (2H, m), 0.70-0.81 (1H, m), 1.39 (3H, d, J = 6.8 Hz), 1.94 (3H, s), 5.25 (1H, d, | CD$_3$OD (400 MHz) | 709 (M + 1)+ |

TABLE 7-continued

| Compound | | NMR data | | MS |
|---|---|---|---|---|
| No. | Compound name | δ (ppm) from TMS | Solvent/Hz | (FAB+) |
| | pipecoloyl-7-deoxy-7-epi-7-(4-(pyrimidin-5-yl)phenylthio)-1-thio-α-linocosamide | J = 5.8 Hz), 7.11-7.24 (3H, m), 7.32-7.40 (2H, m), 7.55 (2H, d, J = 8.5 Hz), 7.68 (2H, d, J = 8.5 Hz), 9.06 (2H, s), 9.12 (1H, s) | | |
| 128 | Methyl 6-N-((2S,4R)-4-cyclopropylmethyl-1-((5-methyl-2-oxo-1,3-dioxol-4-yl)methoxy)carbonyl)-pipecoloyl-7-deoxy-7-epi-7-(4-(pyrimidin-5-yl)phenylthio)-1-thio-α-lincosamide | −0.01-0.05 (2H, m), 0.42-0.48 (2H, m), 0.62-0.74 (1H, m), 1.31 (3H, d, J = 6.8 Hz), 2.07 (3H, s), 2.18 (3H, s), 5.37 (1H, d, J = 5.6 Hz), 7.51-7.58 (4H, m), 8.95 (2H, s), 9.23 (1H, s) | CDCl$_3$ (400 MHz) | 745 (M + 1)+ |
| 129 | Methyl 6-N-((2S,4R)-4-cyclopropylmethyl-1-((5-methyl-2-oxo-1,3-dioxol-4-yl)methyl)pipecoloyl-7-deoxy-7-epi-7-(4-(pyrimidin-5-yl)phenylthio)-1-thio-α-lincosamide | −0.03-0.07 (2H, m), 0.42-0.50 (2H, m), 0.62-0.73 (1H, m), 1.31 (3H, d, J = 6.8 Hz), 2.13 (3H, s), 2.20 (3H, s), 5.42 (1H, d, J = 5.6 Hz), 7.57 (2H, d, J = 8.2 Hz), 7.66 (2H, d, J = 8.2 Hz), 8.95 (2H, s), 9.22 (1H, s) | CD$_3$OD (400 MHz) | 701 (M + 1)+ |
| 130 | Methyl 6-N-((2S,4R)-4-cyclopropylmethyl-1-formyl)pipecoloyl-7-deoxy-7-epi-7-(4-(pyrimidin-5-yl)phenylthio)-1-thio-α-lincosamide | 0-0.1 (2H, m), 0.40-0.5 (2H, m), 0.65-0.75 (1H, m), 1.38 (3H, d, J = 6.9 Hz), 1.93 (3H, s), 5.24 (1H, d, J = 5.4 Hz), 7.57 (2H, d, J = 8.7 Hz), 7.70 (2H, d, J = 8.7 Hz), 8.02 (1H, s), 9.06 (2H, s), 9.10 (1H, s) | CDCl$_3$ (300 MHz) | 617 (M + 1)+ |

TABLE 8

| Compound | | NMR data | | MS |
|---|---|---|---|---|
| No. | Compound name | δ (ppm) from TMS | Solvent/Hz | (FAB+) |
| 131 | Methyl 6-N-((2S,4R)-1-((acetoxymethoxy)-carbonyl)-4-cyclopropylmethyl)-pipecoloyl-7-deoxy-7-epi-7-(4-(pyrimidin-5-yl)phenylthio)-1-thio-α-lincosamide | 0.00-0.06 (2H, m), 0.42-0.48 (2H, m), 0.62-0.74 (1H, m), 1.31 (3H, d, J = 6.8 Hz), 2.09 (3H, s), 5.38 (1H, d, J = 5.4 Hz), 5.74 (1H, d, J = 5.7 Hz), 5.84 (1H, d, J = 5.7 Hz), 7.55 (4H, s), 8.95 (2H, s), 9.23 (1H, s) | CDCl$_3$ (400 MHz) | 705 (M + 1)+ |
| 132 | Methyl 6-N-((2S,4R)-4-cyclopropylmethyl-1-((pivaloyloxy)methoxy-carbonyl))pipecoloyl-7-deoxy-7-epi-7-(4-(pyrimidin-5-yl)phenylthio)-1-thio-α-lincosamide | −0.01-0.04 (2H, m), 0.41-0.48 (2H, m), 0.62-0.74 (1H, m), 1.22 (9H, s), 1.30 (3H, d, J = 6.8 Hz), 2.09 (3H, s), 5.38 (1H, d, J = 5.6 Hz), 5.77 (1H, br), 5.84 (1H, d, J = 5.6 Hz), 7.55 (4H, s), 8.95 (2H, s), 9.23 (1H, s) | CDCl$_3$ (400 MHz) | 747 (M + 1)+ |
| 133 | Methyl 2,3-di-o-acetyl-6-N-((2S,4R)-4-cyclopropylmethyl)pipecoloyl-7-deoxy-7-epi-7-(4-(pyrimidin-5-yl)phenylthio)-1-thio-α-lincosamide monohydrochloride | 0.03-0.11 (2H, m), 0.46-0.57 (2H, m), 0.68-0.80 (1H, m), 1.92 (3H, s), 2.03 (3H, s), 2.08 (3H, s), 5.03 (1H, dd, J = 3.2, 11.0 Hz), 5.37 (1H, dd, J = 5.8, 11.0 Hz), 5.62 (1H, d, J = 5.8 Hz), 7.54 (2H, d, J = 8.5 Hz), 7.71 (2H, d, J = 8.5 Hz), 9.11 (2H, s) | CD$_3$OD (400 MHz) | 729 (M + 1)+ |
| 134 | Methyl 2-o-acetyl-6-N-((2S,4R)-4-cyclopropylmethyl)pipecoloyl-7-deoxy-7-epi-7-(4-(pyrimidin-5-yl)phenylthio)-1-thio-α-lincosamide monohydrochloride | 0.-0.08 (2H, m), 0.44-0.55 (2H, m), 0.68-0.79 (1H, m), 1.93 (3H, s), 2.08 (3H, s), 5.05 (1H, dd, J = 3.2, 11.0 Hz), 5.38 (1H, dd, J = 5.8, 11.0 Hz), 5.64 (1H, d, J = 5.8 Hz), 7.55 (2H, d, J = 8.5 Hz), 7.71 (2H, d, J = 8.5 Hz), 9.10 (2H, s) | CD$_3$OD (400 MHz) | 687 (M + 1)+ |
| 135 | Methyl 2,3-di-o-acetyl-6-N-((2S,4R)-4-cyclopropylmethyl-1-((5-methyl-2-oxo-1,3-dioxol-4-yl)methoxy)carbonyl)- | −0.02-0.04 (2H, m), 0.40-0.48 (2H, m), 0 62-0.73 (1H, m), 1.30 (3H, d, J = 7.1 Hz), 2.00 (3H, s), 2.07 (3H, s), 2.11 (3H, s), 2.20 (3H, s), 5.08 (1H, dd, J = 3.2, 11.0 Hz), 5.41 (1H, dd, | CDCl$_3$ (400 MHz) | 829 (M + 1)+ |

TABLE 8-continued

| Compound No. | Compound name | NMR data δ (ppm) from TMS | Solvent/Hz | MS (FAB+) |
|---|---|---|---|---|
| | pipecoloyl-7-deoxy-7-epi-7-(4-(pyrimidin-5-yl)phenylthio)-1-thio-α-lincosamide | 5.8, 11.0 Hz), 5.41 (1H, dd, J = 5.8, 11.0 Hz), 5.66 (1H, d, J = 5.6 Hz) 7.49-7.58 (4H, m), 8.95 (2H, s), 9.23 (1H, s) | | |
| 136 | Methyl 2-o-acetyl-6-N-((2S,4R)-4-cyclopropylmethyl-1-((5-methyl-2-oxo-1,3-dioxol-4-yl)methoxy)carbonyl-pipecoloyl-7-deoxy-7-epi-7-(4-(pyrimidin-5-yl)phenylthio)-1-thio-α-lincosamide | −0.02-0.06 (2H, m), 0.41-0.49 (2H, m), 0.62-0.73 (1H, m), 1.30 (3H, d, J = 6.8 Hz), 2.02 (3H, s), 2.13 (3H, s), 2.18 (3H, s), 5.16 (1H, dd, J = 5.6, 10.2 Hz), 5.55 (1H, d, J = 5.6 Hz), 7.48-7.59 (4H, m), 8.95 (2H, s), 9.23 (1H, s) | CDCl$_3$ (400 MHz) | 787 (M + 1)+ |
| 137 | Methyl 6-N-((2S,4R)-4-cyclopropylmethyl-1-methyl)pipecoloyl-7-deoxy-7-epi-2-octoyl-7-(4-(pyrimidin-5-yl)phenylthio)-1-thio-α-lincosamide | −0.05-0.05 (2H, m), 0.40-0.49 (2H, m), 0.61-0.74 (1H, m), 1.36 (3H, d, J = 6.8 Hz), 2.05 (3H, s), 2.23 (3H, s), 2.34 (3H, s), 5.17 (1H, dd, J = 5.6, 10.2 Hz), 5.56 (1H, d, J = 5.6 Hz), 7.52-7.60 (4H, m), 8.96 (2H, s), 9.23 (1H, s) | CDCl$_3$ (400 MHz) | 729 (M + 1)+ |
| 138 | Methyl 2,3-di-o-acetyl-6-N-((2S,4R)-4-cyclopropylmethyl-1-methyl)pipecoloyl-7-deoxy-7-epi-7-(4-(pyrimidin-5-yl)phenylthio)-1-thio-α-lincosamide | −0.01-0.05 (2H, m), 0.39-0.48 (2H, m), 0.60-0.72 (1H, m), 1.37 (3H, d, J = 6.8 Hz), 2.03 (3H, s), 2.07 (3H, s), 2.09 (3H, s), 2.21 (3H, s), 5.10 (1H, dd, J = 2.9, 11.0 Hz), 5.43 (1H, dd, J = 5.6, 11.0 Hz), 5.68 (1H, d, J = 5.6 Hz), 7.53-7.61 (4H, m), 8.96 (2H, s), 9.23 (1H, s) | CDCl$_3$ (400 MHz) | 687 (M + 1)+ |
| 139 | Methyl 2-o-acetyl-6-N-((2S,4R)-4-cyclopropylmethyl-1-methyl)pipecoloyl-7-deoxy-7-epi-7-(4-(pyrimidin-5-yl)phenylthio)-1-thio-α-lincosamide | −0.02-0.04 (2H, m), 0.42-0.48 (2H, m), 0.62-0.74 (1H, m), 1.37 (3H, d, J = 6.8 Hz), 2.06 (3H, s), 2.14 (3H, s), 2.23 (3H, s), 5.17 (1H, dd, J = 5.6, 10.5 Hz), 5.57 (1H, d, J = 5.6 Hz), 7.53-7.60 (4H, m), 9.23 (1H, s) | CDCl$_3$ (400 MHz) | 645 (M + 1)+ |
| 140 | Methyl 2,3,4-tri-o-acetyl-6-N-((2S,4R)-4-cyclopropylmethyl-1-methyl)pipecoloyl-7-deoxy-7-epi-7-(4-(pyrimidin-5-yl)phenylthio)-1-thio-α-lincosamide | −0.03-0.04 (1H, m), 0.06-0.12 (1H, m), 0.36-0.48 (2H, m), 0.63-0.75 (1H, m), 1.41 (3H, d, J = 6.8 Hz), 2.08 (3H, s), 2.15 (3H, s), 2.18 (6H, s), 2.25 (3H, s), 5.14 (1H, dd, J = 3.0, 11.1 Hz), 5.27 (1H, dd, 5.6, 11.1 Hz), 5.32 (1H, d, J = 3.0 Hz), 5.63 (1H, d, J = 5.6 Hz), 7.46-7.54 (4H, m), 8.94 (2H, s), 9.21 (1H, s) | CDCl$_3$ (400 MHz) | 729 (M + 1)+ |
| 141 | Methyl 6-N-((2S,4R)-4-cyclopropylmethyl-1-methyl)pipecoloyl-7-deoxy-7-epi-2,3-di-o-propionyl-7-(4-(pyrimidin-5-yl)phenylthio)-1-thio-α-lincosamide | 2.03 (3H, s), 2.21 (3H, s), 5.67 (1H, d, J = 5.6 Hz), 7.56 (4H, d, J = 4.1 Hz), 8.95 (2H, s), 9.23 (1H, s) | CDCl$_3$ (400 MHz) | 715 (M+ + 1) |
| 142 | Methyl 6-N-((2S,4R)-4-cyclopropylmethyl-1-methyl)pipecoloyl-7-deoxy-7-epi-2-o-propionyl-7-(4-(pyrimidin-5-yl)phenylthio)-1-thio-α-lincosamide | −0.04-0.06 (2H, m), 0.40-0.50 (2H, m), 0.63-0.74 (1H, m), 1.16 (3H, t, J = 7.6 Hz), 1.36 (3H, d, J = 7.1 Hz), 2.05 (3H, s), 2.23 (3H, s), 5.18 (1H, dd, J = 5.6, 10.2 Hz), 5.57 (1H, d, J = 5.6 Hz), 7.42-7.60 (4H, m), 8.95 (2H, s), 9.23 (1H, s) | CDCl$_3$ (400 MHz) | 659 (M + 1)+ |
| 143 | Methyl 6-N-((2S,4R)-4-cyclopropylmethyl-1-methyl)pipecoloyl-7-deoxy-7-epi-2-o-hexanoyl-7-(4-(pyrimidin-5-yl)phenylthio)-1-thio-α-lincosamide | −0.03-0.05 (2H, m), 0.42-0.48 (2H, m), 0.63-0.73 (1H, m), 1.37 (3H, d, J = 6.8 Hz), 2.05 (3H, s), 2.23 (3H, s), 5.17 (1H, dd, J = 5.6, 10.5 Hz), 5.56 1H, d, J = 5.6 Hz), 7.53-7.60 (4H, m), 8.96 (2H, s), 9.23 (1H, s) | CDCl$_3$ (400 MHz) | 701 (M + 1)+ |
| 144 | Methyl 2-o-benzoyl-6-N-((2S,4R)-4-cyclopropylmethyl-1-methyl)pipecoloyl-7-deoxy-7-epi-7-(4-(pyrimidin-5-yl)phenylthio)-1-thio-α-lincosamide | −0.03-0.04 (2H, m), 0.41-0.49 (2H, m), 0.63-0.74 (1H, m), 1.38 (3H, d, J = 6.8 Hz), 2.06 (3H, s), 2.24 (3H, s), 5.46 (1H, dd, J = 5.6, 10.2 Hz), 5.66 (1H, d, J = 5.6 Hz), 7.44 (2H, t, d = 8.0 Hz), 7.52-7.61 (5H, m), 8.07-8.12 (2H, m), 8.96 (2H, s), 9.23 (1H, s) | CDCl$_3$ (400 MHz) | 707 (M + 1)+ |

TABLE 9
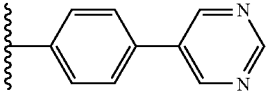
| Compound No. | A-R₁ |
|---|---|
| 1 | 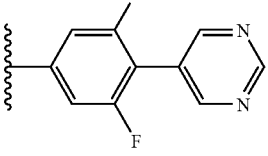 |
| 2 | 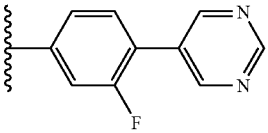 |
| 3 | 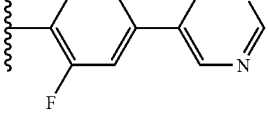 |
| 4 | 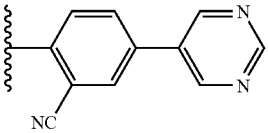 |
| 5 | 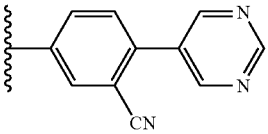 |
| 6 | 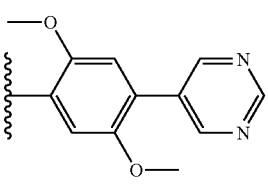 |
| 7 | 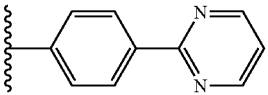 |
| 8 | 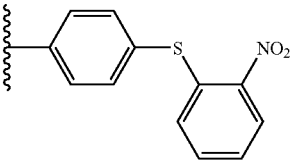 |
TABLE 9-continued
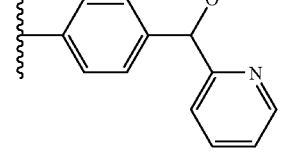
| Compound No. | A-R₁ |
|---|---|
| 9 | 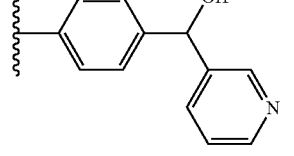 |
| 10 | 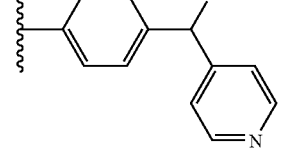 |
| 11 | 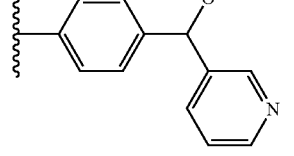 |
| 12 | 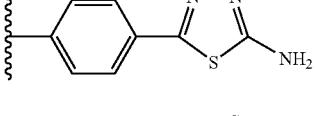 |
| 13 | 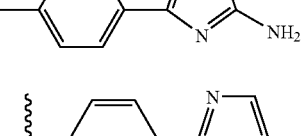 |
| 14 | |
| 15 | |
| 16 | |

TABLE 9-continued

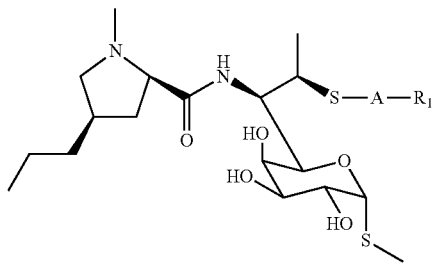

| Compound No. | A-R₁ |
|---|---|
| 17 | 4-(4-(dimethylcarbamoyl)thiazol-2-yl)phenyl |
| 18 | 4-(4-carbamoylthiazol-2-yl)phenyl |
| 19 | 4-(5-carbamoylthiazol-2-yl)phenyl |
| 20 | 4-(5-(dimethylcarbamoyl)thiazol-2-yl)phenyl |
| 21 | 4-(2-methoxypyrimidin-5-yl)phenyl |
| 22 | 4-(1,3,4-thiadiazol-2-yl)phenyl |
| 23 | 4-(isoxazol-5-yl)phenyl |
| 24 | 4-(1,2,3-thiadiazol-4-yl)phenyl |
| 25 | 4-(pyrazin-2-yl)phenyl |
| 26 | 4-(thiazol-4-yl)phenyl |

TABLE 9-continued

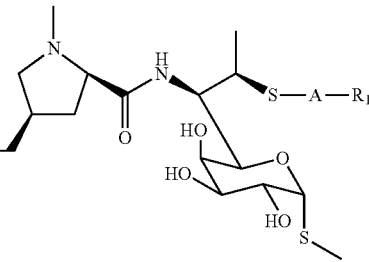

| Compound No. | A-R₁ |
|---|---|
| 27 | 4-(oxazol-5-yl)phenyl |
| 28 | 4-(thiazol-5-yl)phenyl |
| 29 | 4-(4-(dimethylcarbamoyl)thiazol-5-yl)phenyl |
| 30 | 4-(5-aminopyrazin-2-yl)phenyl |
| 47 | 4-(piperazin-1-yl)phenyl |
| 52 | 4-(4-methylpiperazin-1-yl)phenyl |
| 50 | 4-(piperidin-3-yl)phenyl |
| 51 | 4-(1-methylpiperidin-3-yl)phenyl |
| 56 | 4-(1-ethylpiperidin-3-yl)phenyl |
| 55 | 4-(1-acetylpiperidin-3-yl)phenyl |

TABLE 9-continued
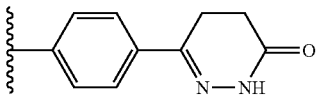
| Compound No. | A-R₁ |
|---|---|
| 31 | 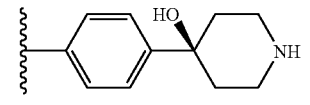 |
| 48 | 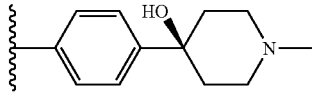 |
| 53 | 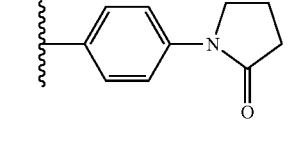 |
| 32 | 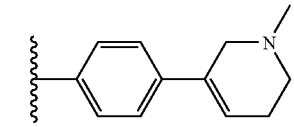 |
| 33 | 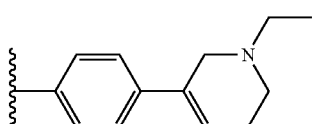 |
| 34 | 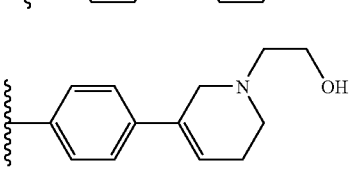 |
| 35 | 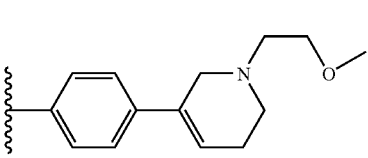 |
| 36 | 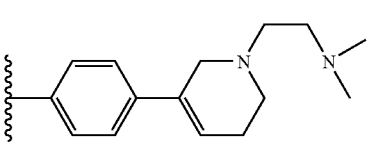 |
| 37 | 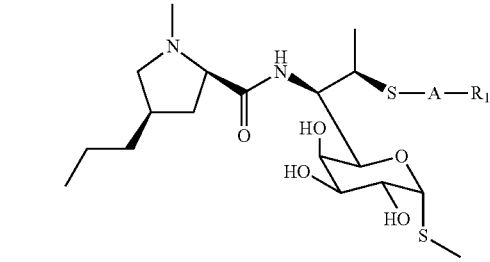 |
TABLE 9-continued
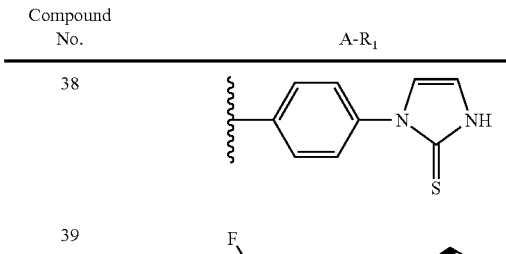
| Compound No. | A-R₁ |
|---|---|
| 38 | 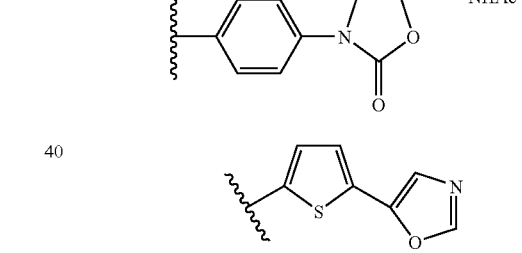 |
| 39 | 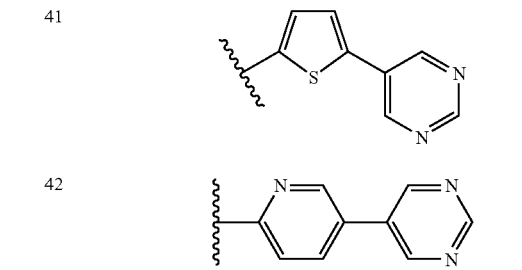 |
| 40 | 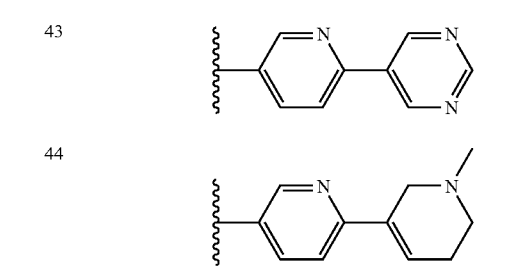 |
| 41 | 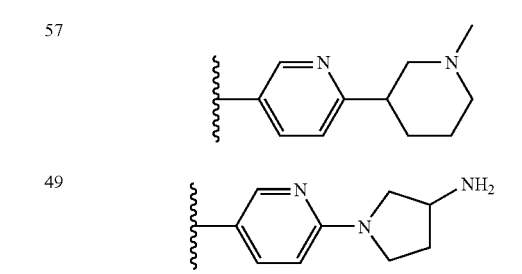 |
| 42 |  |
| 43 |  |
| 44 |  |
| 57 |  |
| 49 | |

TABLE 9-continued
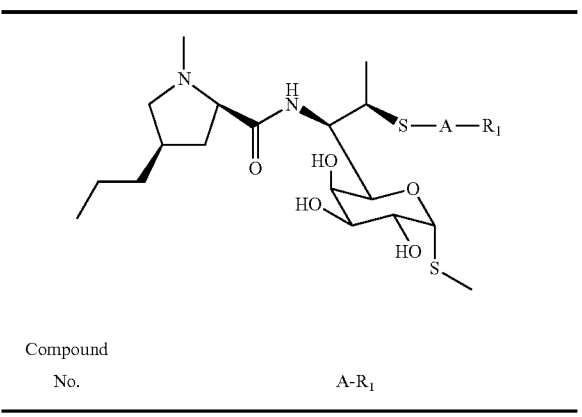
| Compound No. | A-R₁ |
|---|---|
| 54 | |
| 45 | |
| 46 | |
TABLE 10
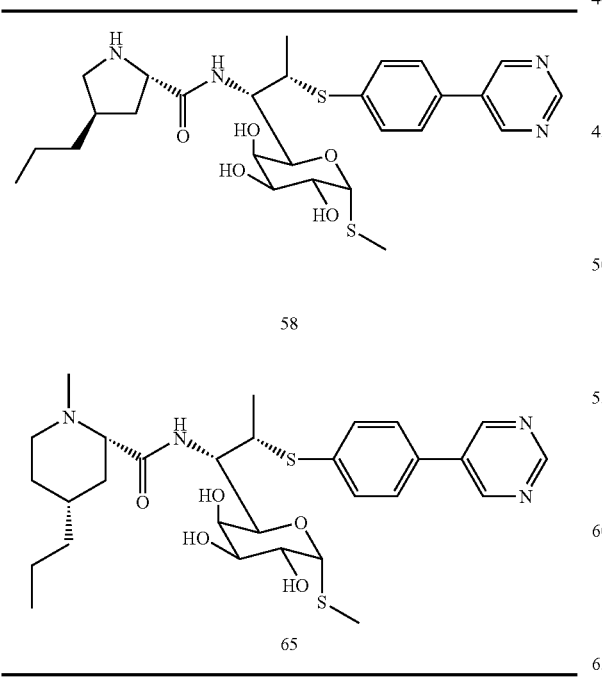
58
65
TABLE 11
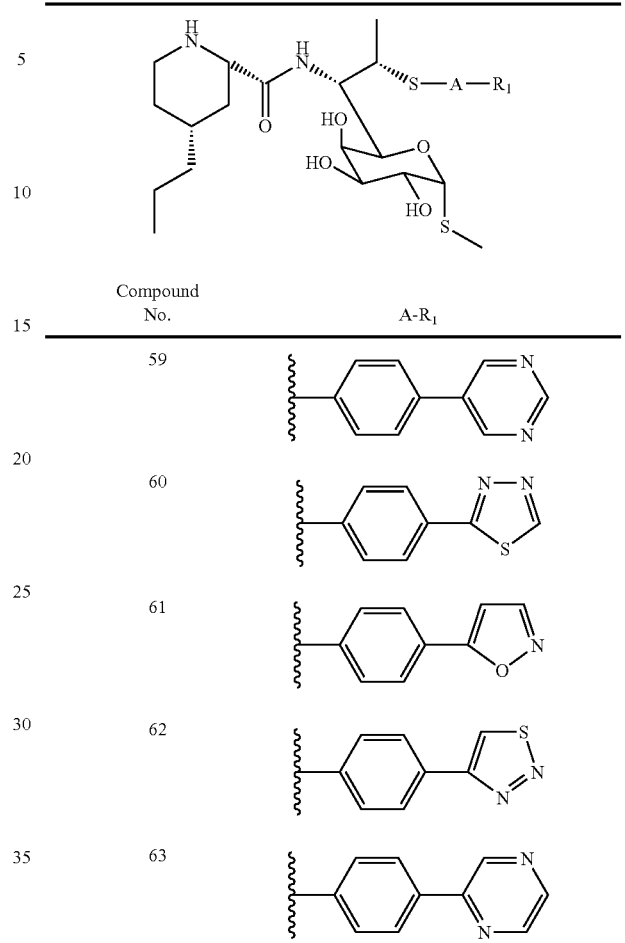
| Compound No. | A-R₁ |
|---|---|
| 59 | |
| 60 | |
| 61 | |
| 62 | |
| 63 | |
| 64 | |
TABLE 12
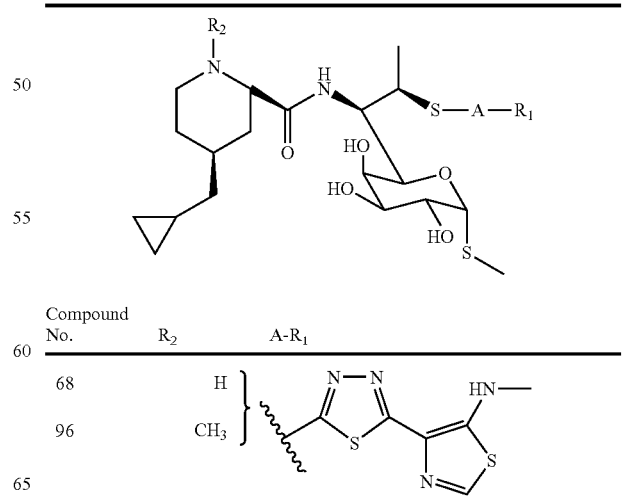
| Compound No. | R₂ | A-R₁ |
|---|---|---|
| 68 | H | |
| 96 | CH₃ | |

TABLE 12-continued

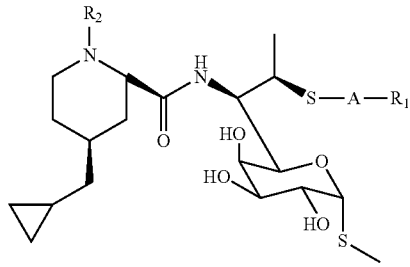

| Compound No. | R₂ | A-R₁ |
|---|---|---|
| 69 | H | (1,3,4-thiadiazole with 2-NO₂-5-methylphenyl) |
| 70 / 97 | H / CH₃ | (oxazole with 2-NO₂-4,5-dimethoxyphenyl) |
| 98 | H | (1,3,4-oxadiazole with 2-NO₂-4,5-dimethoxyphenyl) |
| 71 / 99 | H / CH₃ | (1,3,4-oxadiazole with 5-(methylamino)thiazole) |
| 72 / 100 / 121 / 122 | H / CH₃ / -CH₂CH₂OH / -cyclopropyl | (4-(pyrimidin-5-yl)phenyl) |
| 73 / 101 | H / CH₃ | (4-(pyridin-3-yl)phenyl) |

TABLE 12-continued

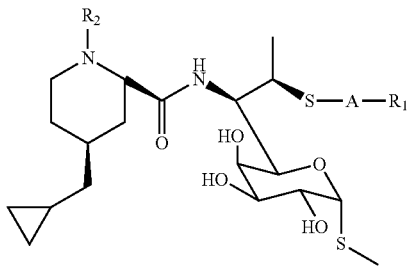

| Compound No. | R₂ | A-R₁ |
|---|---|---|
| 74 / 102 | H / CH₃ | (4-(5-fluoropyridin-3-yl)phenyl) |
| 75 / 103 | H / CH₃ | (4-(6-fluoropyridin-3-yl)phenyl) |
| 76 | H | (4-(4-nitropyridin-3-yl N-oxide)phenyl) |
| 77 / 104 | H / CH₃ | (4-(5-cyanopyridin-3-yl)phenyl) |
| 78 / 105 | H / CH₃ | (4-(5-methoxypyridin-3-yl)phenyl) |
| 79 / 106 | H / CH₃ | (4-(methoxy(pyridin-2-yl)methyl)phenyl) |
| 80 / 107 | H / CH₃ | (4-(methoxy(pyridin-4-yl)methyl)phenyl) |
| 81 | H | (4-(isoxazol-5-yl)phenyl) |

TABLE 12-continued

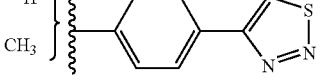

| Compound No. | R₂ | A-R₁ |
|---|---|---|
| 82 | H | |
| 108 | CH₃ | phenyl-thiadiazole |
| 83 | H | |
| 109 | CH₃ | phenyl-pyrazine |
| 84 | H | |
| 110 | CH₃ | phenyl-diaminotriazine |
| 85 | H | |
| 111 | CH₃ | phenyl-imidazole |
| 94 | H | |
| 112 | CH₃ | phenyl-methylmorpholine |
| 86 | H | |
| 113 | CH₃ | phenyl-N-methyltetrahydropyridine |
| 87 | H | |
| 114 | CH₃ | phenyl-N-ethyltetrahydropyridine |
| 95 | H | |
| 115 | CH₃ | phenyl-N-methylpiperidine |
| 88 | H | |
| 116 | CH₃ | phenyl-morpholinocarbonyl |

TABLE 12-continued

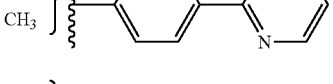

| Compound No. | R₂ | A-R₁ |
|---|---|---|
| 89 | H | pyridyl-pyridine |
| 90 | H | |
| 117 | CH₃ | pyridyl-pyrimidine |
| 91 | H | |
| 118 | CH₃ | pyridyl-pyrimidine |
| 92 | H | |
| 119 | CH₃ | pyridyl-pyridine |
| 93 | H | |
| 120 | CH₃ | pyridyl-N-methyltetrahydropyridine |

TABLE 13

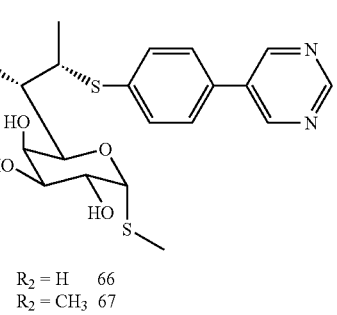

R₂ = H   66
R₂ = CH₃  67

TABLE 13-continued
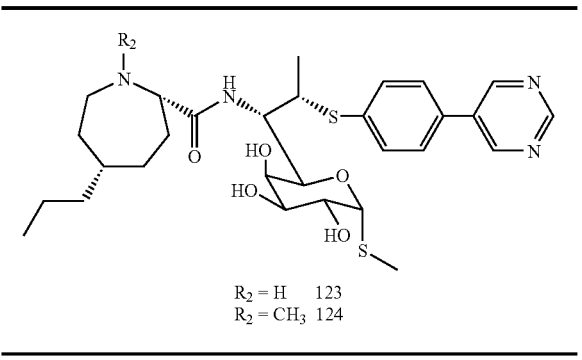
| | |
|---|---|
| $R_2$ = H | 123 |
| $R_2$ = $CH_3$ | 124 |
TABLE 14
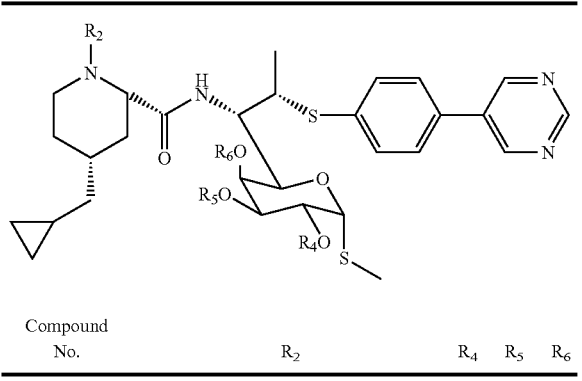
| Compound No. | $R_2$ | $R_4$ | $R_5$ | $R_6$ |
|---|---|---|---|---|
| 125 | $AcNHCH_2$ | H | H | H |
| 126 | EtOCO | H | H | H |
| 127 | PhOCO | H | H | H |
| 128 | 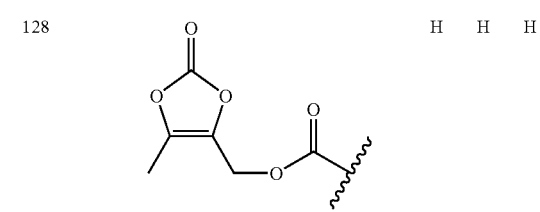 | H | H | H |
| 129 | 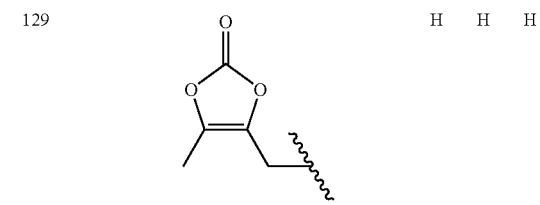 | H | H | H |
| 130 | CHO | H | H | H |
| 131 | $AcOCH_2CO$ | H | H | H |
| 132 | 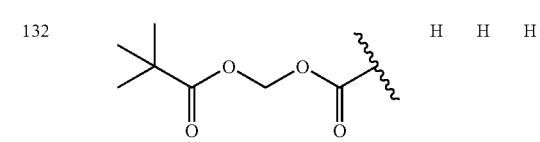 | H | H | H |
| 133 | H | Ac | Ac | H |
| 134 | H | Ac | H | H |
TABLE 14-continued
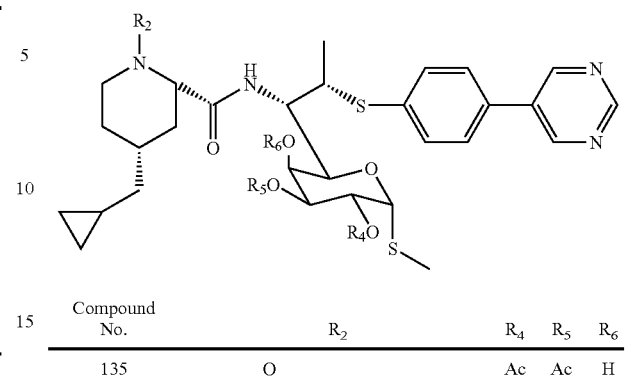
| Compound No. | $R_2$ | $R_4$ | $R_5$ | $R_6$ |
|---|---|---|---|---|
| 135 | 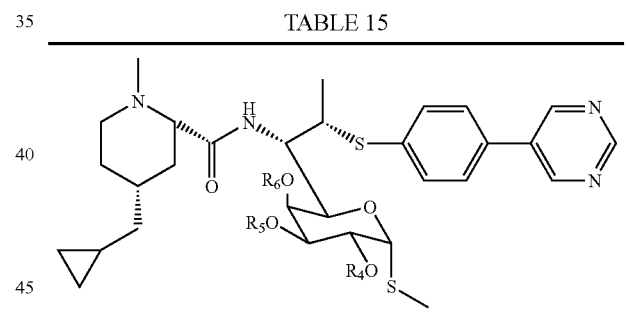 | | Ac | Ac | H |
| 136 | 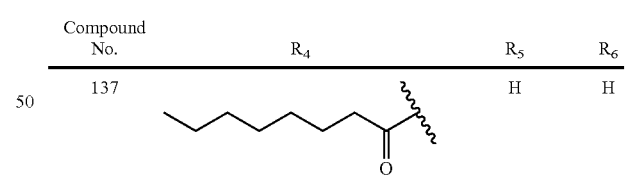 | | Ac | H | H |
TABLE 15
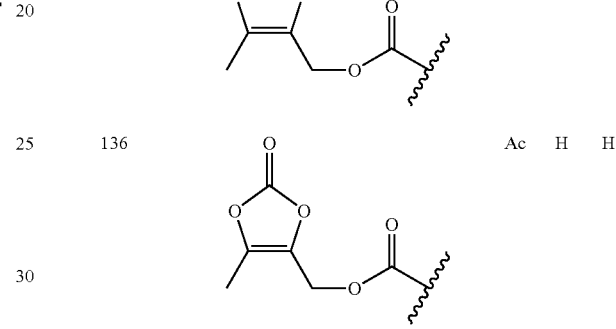
| Compound No. | $R_4$ | $R_5$ | $R_6$ |
|---|---|---|---|
| 137 | 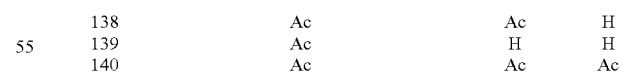 | H | H |
| 138 | Ac | Ac | H |
| 139 | Ac | H | H |
| 140 | Ac | Ac | Ac |
| 141 | 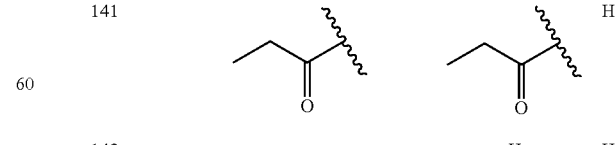 | 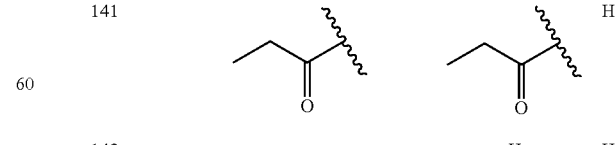 | H |
| 142 | 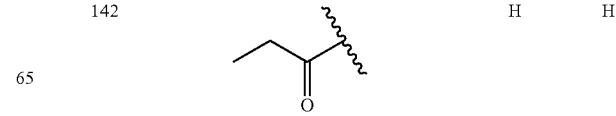 | H | H |

TABLE 15-continued

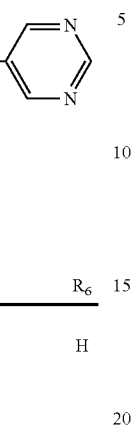

| Compound No. | R₄ | R₅ | R₆ |
|---|---|---|---|
| 143 | ![hexanoyl group] | H | H |
| 144 | Bz | H | H |

TABLE 16

[Structure with R = H (145) and R = CH₃ (146)]

R = H   145
R = CH₃ 146

TABLE 17

| Compound No. | Compound name | NMR data δ (ppm) from TMS | Solvent/Hz | MS (FAB⁺) |
|---|---|---|---|---|
| 145 | Methyl 6-N-((2S,4R)-(4-cyclopropylmethyl)-pipecoloyl)-7-deoxy-7-epi-7-(4-(1-methylpyrrolidin-3-yl)phenylthio)-1-thio-α-lincosamide | −0.04-0.03(2H, m), 0.39-0.46(2H, m), 0.64-0.76 (1H, m), 0.99-1.30(8H, m), 1.64(1H, br), 1.72-1.79 (1H, m), 1.80-1.92 (1H, m), 1.94 (3H, s), 1.99-2.18 (1H, m), 2.25-2.35 (1H, m), 2.44 (3H, s), 2.45(1H, t, J = 9.3 Hz), 2.57-2.70(2H, m), 2.80-2.89 (1H, m), 3.00-3.16(2H, m), 3.30-3.42 (1H, m), 3.52-3.58 (1H, m), 3.71-3.78 (1H, m), 3.84 (1H, d, J = 3.2 Hz), 4.06(1H, dd, J = 10.2, 5.6 Hz), 4.48(1H, d, J = 10.0 Hz), 4.50(1H, dd, J = 10.0, 2.2 Hz), 5.24(1H, d, J = 5.6 Hz), 7.20(2H, d, J = 8.3 Hz), 7.32(2H, d, J = 8.3 Hz) | CD₃OD (400 MHz) | 594 (M + H)⁺ |
| 146 | Methyl 6-N-((2S,4R)-(4-cyclopropylmethyl-1-methyl)pipecoloyl)-7-deoxy-7-epi-7-(4-(1-methylpyrrolidin-3-yl)phenylthio)-1-thio-α-lincosamide | −0.03-0.05(2H, m), 0.40-0.48(2H, m), 0.65-0.76 (1H, m), 1.17(2H, t, J = 6.8 Hz), 1.24-1.38(5H, m), 1.49(1H, br), 1.76-1.83 (1H, m), 1.84-2.02(5H, m), 2.07-2.17 (1H, m), 2.25 (3H, s), 2.28-2.38 (1H, m), 2.42 (3H, s), 2.48(1H, t, J = 8.8 Hz), 2.60(1H, dd, J = 11.5, 2.9 Hz), 2.69(1H, dt, J = 6.1, 8.8 Hz), 2.88-2.92 (1H, m), 2.93-2.99 (1H, m), 3.06-3.10 (1H, m), 3.34-3.44 (1H, m), 3.58(1H, dd, J = 10.2, 3.2 Hz), 3.66-3.74(2H, m), 4.10(1H, dd, J = 10.2, 5.6 Hz), 4.40(1H, d, J = 10.0 Hz), 4.54(1H, dd, J = 10.0, 2.7 Hz), 5.27(1H, d, J = 5.6 Hz), 7.23(2H, d, J = 8.3 Hz), 7.36(2H, d, J = 8.3 Hz) | CD₃OD (400 MHz) | 608 (M + H)⁺ |

The invention claimed is:
1. A compound of formula (I) or its pharmacologically acceptable salt:

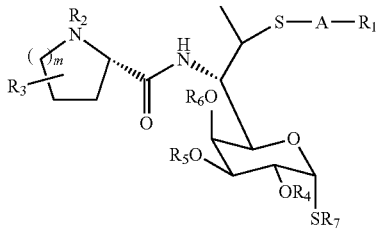

wherein
A represents
benzyl in which methylene in the benzyl group is bonded to S;
aryl optionally substituted by one or more groups selected from the group consisting of $C_{1-6}$ alkyl, a halide, cyano, and $C_{1-6}$ alkyloxy; or
a monocyclic or dicyclic heterocyclic group in which each ring has four to six members, optionally substituted by one or more groups selected from the group consisting of $C_{1-6}$ alkyl and $C_{1-6}$ alkyl halides
wherein the heterocyclic group contains 1 to 4 dissimilar atoms selected from the group consisting of nitrogen, oxygen, and sulfur atoms,
$R_1$ represents
pyridyl-$CHR_8$- wherein $R_8$ represents hydroxyl or $C_{1-6}$ alkyloxy;
morpholinocarbonyl;
arylthio optionally substituted by one or more groups selected from the group consisting of $C_{1-6}$ alkyl, halides, cyano, and nitro;
optionally substituted aryl
wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, $C_{1-6}$ alkyloxy halides, hydroxy-$C_{1-6}$ alkyl, hydroxy-$C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;
an optionally substituted five- to seven-membered monocyclic heterocyclic group
wherein the five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or
a dicyclic heterocyclic group in which each of the rings has four to six members
$R_2$ represents
a hydrogen atom;
optionally substituted $C_{1-6}$ alkyl;
optionally substituted $C_{2-6}$ alkenyl;
optionally substituted acyl;
$C_{1-6}$ alkylcarbonylaminomethyl;
$C_{1-6}$ alkylcarbonyloxymethylcarbonyl;
$C_{1-6}$ alkylcarbonyloxymethyloxycarbonyl;
(5-methyl-1,3-dioxol-2-oxo-4-yl)methyl;
(5-methyl-1,3-dioxol-2-oxo-4-yl)methyloxycarbonyl;
optionally substituted $C_{1-6}$ alkyloxycarbonyl
wherein the $C_{1-6}$ alkyl, $C_{2-6}$ alkenyl, acyl, and $C_{1-6}$ alkyloxycarbonyl groups in $R_2$ are optionally substituted by one or more groups selected from the group consisting of heterocyclic rings optionally substituted by $C_{1-6}$ alkyl, amino, hydroxy, and cyano;
aryloxycarbonyl; or
$C_{3-6}$ cycloalkyl,
$R_3$ represents
optionally substituted $C_{1-6}$ alkyl
wherein the $C_{1-6}$ alkyl group is optionally substituted by one or more groups that are selected from the group consisting of halides; nitro; hydroxy; amino; $C_{1-6}$ alkyloxycarbonyl; cyano; $C_{1-6}$ alkyloxy; oxo; heterocyclic rings; carbamoyl; azide; $C_{1-6}$ alkylaminocarbonyl; di-$C_{1-6}$ alkylaminocarbonyl; and aryl optionally substituted by a halide, hydroxy, or $C_{1-4}$ alkyl;
$C_{3-6}$ cycloalkyl-$C_{1-4}$ alkyl; or
$C_{2-6}$ alkenyl,
$R_4$, $R_5$, and $R_6$, which may be the same or different, represent
a hydrogen atom;
optionally substituted $C_{1-6}$ alkyl;
optionally substituted acyl
wherein the $C_{1-6}$ alkyl group and hydrogen atoms on the acyl group in $R_4$, $R_5$, and $R_6$ are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy or $C_{1-4}$ alkyl; or
benzoyl,
$R_7$ represents
$C_{1-6}$ alkyl optionally substituted by one or more groups selected from the group consisting of halides and hydroxy, and
m is 1 to 3,
provided that
when $R_3$ represents optionally substituted $C_{1-6}$ alkyl or $C_{2-6}$ alkenyl, $R_1$-A -represents
a group selected from the group consisting of 5-pyrimidinyl-phenyl-, 2-pyrimidinyl-phenyl-, 3-piperidinyl-phenyl-, 4-piperidinyl-phenyl-, 3-tetrahydropyridyl-phenyl-, 2-pyrazinyl-phenyl-, 6-tetrahydropyridazinyl-phenyl-, 1,2-oxazol-5-yl-phenyl-, 1,3-oxazolidin-3-yl-phenyl-, 1,2,3-thiadiazol-4-yl-phenyl, 1,3,4-thiadiazol-2-yl-phenyl, 2-(3-piperidinyl)-pyridin-3-yl, 1,3-oxazol-5-yl-phenyl-, phenylthio-phenyl-, $C_{1-6}$ alkyloxy(pyridyl)methyl-phenyl-, hydroxy(pyridyl)methyl-phenyl-, thiazol-4-yl-phenyl-, thiazol-2-yl-phenyl-, 1-piperazinyl-phenyl-, 1-pyrrolidinyl-phenyl-, 1-dihydroimidazolyl-phenyl-, 2-(1,3-oxazol-5-yl)-thiophen-4-yl -, 2-(pyrimidin-5-yl)-thiophen-4-yl, 3-(pyrimidin-5-yl)-pyridin-6-yl, 2-(pyrimidin-5-yl)-pyridin-5-yl, 2-(tetrahydropyridin-3-yl)-pyridin-5-yl, 2-(pyrrolidin-1-yl)-pyridin-5-yl, 5-(pyrimidin-5-yl)-pyrimidin-2-yl, and 2-(pyrimidin-5-yl)-pyrimidin-5-yl wherein $R_1$ and A in the $R_1$-A- group each are optionally substituted as defined above.

2. The compound according to claim 1 or its pharmacologically acceptable salt, wherein formula (I) is represented by formula (II):

$$\text{(II)}$$

wherein A, $R_1$, $R_2$, $R_3$, $R_4$, $R_5$, $R_6$, $R_7$, and m are as defined in formula (I) in claim 1.

3. The compound according to claim 1 or its pharmacologically acceptable salt, wherein
A represents
 benzyl in which methylene in the benzyl group is bonded to S;
 aryl optionally substituted by one or more groups selected from the group consisting of $C_{1-6}$ alkyl, halides, cyano, and $C_{1-6}$ alkyloxy; or
 a monocyclic or dicyclic heterocyclic group, in which each of the rings has four to six members, optionally substituted by one or more groups selected from the group consisting of $C_{1-6}$ alkyl and $C_{1-6}$ alkyl halides
  wherein the heterocyclic group is selected from the group consisting of azetidinyl, thienyl, imidazolyl, thiazolyl, 1,3,4-thiadiazolyl, 1,2,4-thiadiazolyl, 1,3,4-oxadiazolyl, 1,2,4-triazolyl, pyridyl, pyrimidinyl, benzoxazolyl, benzothiazolyl, and oxazolyl, and
$R_1$ represents
 pyridyl-$CHR_8$- wherein $R_8$ represents hydroxyl or $C_{1-6}$ alkyloxy;
 morpholinocarbonyl;
 arylthio optionally substituted by one or more groups selected from the group consisting of $C_{1-6}$ alkyl, halides, cyano, and nitro
 optionally substituted aryl
  wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, $C_{1-6}$ alkyloxy halides, hydroxy-$C_{1-6}$ alkyl, hydroxy-$C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;
 optionally substituted five- to seven-membered monocyclic heterocyclic group
  wherein the five- to seven-membered heterocyclic group is a group selected from the group consisting of pyridyl, furyl, pyrazolyl, imidazolyl, dihydroimidazolyl, pyrrolidinyl, dihydropyrrolyl, 1,3-oxazolidinyl, tetrazolyl, thiazolyl, 1,2,3-thiadiazolyl, 1,3,4-thiadiazolyl, 1,3,5-triazinyl, 1,3,4-triazolyl, pyrimidinyl, 1,2-oxazolyl, 1,3-oxazolyl, pyrazinyl, morpholinyl, piperidinyl, piperazinyl, tetrahydropyridazinyl, tetrahydropyridyl, 1,4-oxazepanyl, azepanyl, tetrahydroazepinyl, and 1,4-diazepanyl, and
 the five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, acylamino, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, $C_{1-6}$ alkylamino, amino, oxo, thioxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or
 a dicyclic heterocyclic group in which each of the rings has four to six members
  wherein the dicyclic heterocyclic group is a group selected from the group consisting of quinoline, quinazoline, benzoxazol, and benzothiazole.

4. The compound according to claim 1 or its pharmacologically acceptable salt, wherein
A represents
 optionally substituted aryl; or
 an optionally substituted monocyclic or dicyclic heterocyclic group in which each of the rings has four to six members,
$R_1$ represents
 pyridyl-$CHR_8$- wherein $R_8$ represents hydroxyl or $C_{1-6}$ alkyloxy;
 morpholinocarbonyl;
 optionally substituted arylthio;
 optionally substituted aryl; or
 an optionally substituted five- to seven-membered monocyclic heterocyclic group, and
$R_3$ represents
 optionally substituted $C_{1-6}$ alkyl; or
 $C_{3-6}$ cycloalkyl-$C_{1-4}$ alkyl.

5. The compound according to claim 1 or its pharmacologically acceptable salt, wherein
A represents
 phenyl optionally substituted by one or more groups selected from the group consisting of halides, cyano, and $C_{1-6}$ alkyloxy; or
 a four- to six-membered monocyclic heterocyclic group
  wherein the heterocyclic group is selected from the group consisting of thienyl, 1,3,4-thiadiazolyl, 1,3,4-oxadiazolyl, pyridyl, pyrimidinyl, and oxazolyl,
$R_1$ represents
 pyridyl-$CHR_8$- wherein $R_8$ represents hydroxyl or $C_{1-6}$ alkyloxy;
 morpholinocarbonyl;
 phenylthio optionally substituted by nitro;
 optionally substituted phenyl
  wherein the phenyl group is optionally substituted by one or more groups that may be the same or different and are selected from the group consisting of nitro, amino, $C_{1-6}$ alkyl, and $C_{1-6}$ alkyloxy; or
 an optionally substituted five- to seven-membered monocyclic heterocyclic group
  wherein the five- to seven-membered heterocyclic group is a group selected from the group consisting of pyridyl, imidazolyl, dihydroimidazolyl, pyrrolidinyl, thiazolyl, 1,2,3-thiadiazolyl, 1,3,4-thiadiazolyl, 1,3,5-triazinyl, pyrimidinyl, 1,2-oxazolyl, 1,3-oxazolyl, pyrazinyl, morpholinyl, piperidinyl, piperazinyl, tetrahydropyridazinyl, and tetrahydropyridyl, and the five- to seven-membered heterocyclic group is optionally substituted by one or more groups selected from the group consisting of halides, nitro, cyano, $C_{1-6}$ alkylamino, di-$C_{1-6}$ alkylamino, acyl, $C_{1-6}$ alkyloxy, hydroxy, $C_{1-6}$ alkyl, hydroxy-$C_{1-6}$ alkyl, di-$C_{1-6}$ alkylamino-$C_{1-6}$ alkyl, acylamino-$C_{1-6}$ alkyl, amino, oxo, thioxo, carbamoyl, di-$C_{1-6}$ alkylaminocarbonyl, $C_{1-6}$ alkyloxy-$C_{1-6}$ alkyl, and N-oxide, and $R_3$ represents
$C_{1-6}$ alkyl; or
$C_{3-6}$ cycloalkyl $C_{1-4}$ alkyl.

6. The compound according to claim 5 or its pharmacologically acceptable salt, wherein $R_2$ represents
a hydrogen atom;
$C_{1-6}$ alkyl optionally substituted by hydroxy;
acyl;
$C_{1-4}$ alkylcarbonylaminomethyl;
$C_{1-4}$ alkylcarbonyloxymethylcarbonyl;
(5-methyl-1,3-dioxol-2-oxo-4-yl)methyl;
(5-methyl-1,3-dioxol-2-oxo-4-yl)methyloxycarbonyl;
$C_{1-6}$ alkyloxycarbonyl; or
aryloxycarbonyl, $R_4$, $R_5$, and $R_6$ simultaneously represent a hydrogen atom, and
$R_7$ represents $C_{1-4}$ alkyl.

7. The compound according to claim 1 or its pharmacologically acceptable salt, wherein A represents optionally substituted aryl while $R_1$ represents an optionally substituted five- or six-membered monocyclic heterocyclic group, or A represents an optionally substituted four- to six-membered monocyclic heterocyclic group while $R_1$ represents an optionally substituted aryl or an optionally substituted five- or six-membered monocyclic heterocyclic group.

8. The compound according to claim 1 or its pharmacologically acceptable salt, wherein $R_1$-A- represents 5-pyrimidinyl-phenyl- or 3-tetrahydropyridyl-phenyl- wherein $R_1$ and A in the $R_1$-A- group each are optionally substituted as defined in claim 1.

9. The compound according to claim 1 or its pharmacologically acceptable salt, wherein $R_3$ represents optionally substituted $C_{3-6}$ cycloalkyl-$C_{1-4}$ alkyl.

10. A pharmaceutical composition comprising a compound according to claim 1 or its pharmacologically acceptable salt and a pharmaceutically acceptable carrier.

11. The pharmaceutical composition according to claim 10, which further comprises an additive for a pharmaceutical preparation.

12. A method for a treating bacterial infectious disease, comprising administering a therapeutically effective amount of a compound according to claim 1 or its pharmacologically acceptable salt together with a pharmaceutically acceptable carrier to a mammal or a domestic fowl having a bacterial infectious disease.

13. The method according to claim 12, wherein the bacterial infectious disease is in a respiratory organ.

* * * * *